United States Patent
Ohana

(10) Patent No.: US 11,332,510 B2
(45) Date of Patent: May 17, 2022

(54) SUCCINATE-BINDING POLYPEPTIDES AND USE THEREOF

(71) Applicant: B. G. NEGEV TECHNOLOGIES AND APPLICATIONS LTD., AT BEN-GURION UNIVERSITY, Beer Sheva (IL)

(72) Inventor: Ehud Ohana, Meitar (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 0 days.

(21) Appl. No.: 16/647,945

(22) PCT Filed: Sep. 18, 2018

(86) PCT No.: PCT/IL2018/051060
§ 371 (c)(1),
(2) Date: Mar. 17, 2020

(87) PCT Pub. No.: WO2019/053731
PCT Pub. Date: Mar. 21, 2019

(65) Prior Publication Data
US 2020/0262889 A1 Aug. 20, 2020

Related U.S. Application Data

(60) Provisional application No. 62/623,864, filed on Jan. 30, 2018, provisional application No. 62/623,825, filed on Jan. 30, 2018, provisional application No. 62/559,694, filed on Sep. 18, 2017.

(51) Int. Cl.
| | |
|---|---|
| C07K 14/705 | (2006.01) |
| A61K 38/00 | (2006.01) |
| A61P 9/12 | (2006.01) |
| A61P 1/00 | (2006.01) |
| C07K 14/47 | (2006.01) |

(52) U.S. Cl.
CPC .............. *C07K 14/705* (2013.01); *A61P 1/00* (2018.01); *A61P 9/12* (2018.01); *C07K 14/47* (2013.01); *A61K 38/00* (2013.01); *C07K 2319/00* (2013.01)

(58) Field of Classification Search
CPC .......... C07K 14/705; A61K 38/00; A61P 9/12
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,019,369 A | 5/1991 | Presant et al. |
| 5,871,963 A | 2/1999 | Conley et al. |
| 2003/0054487 A1 | 3/2003 | Li |
| 2009/0298188 A1 | 12/2009 | Peti-Peterdi |

FOREIGN PATENT DOCUMENTS

EP     2014297 A1     1/2009

OTHER PUBLICATIONS

Alper et al., 2013, The SLC26 gene family of anion transporters and channels, Molecular Aspects of Medicine, 34: 494-515.*
Yamazaki et al., 2011, Functional characterization of the P1059L mutation in the inositol 1,4,5-triphosphate receptor type 1 identified in a Japanese SCA15 family, Biochemical and Biophysical Research Communications, 410: 754-758.*
Gilissen et al., 2016, Insight into SUCNR1 (GPR91) structure and function, Pharmacology & Therapeutics, 159: 56-65.*
Sadagopan et al., 2007, Circulating Succinate is Elevated in Rodent Models of Hypertension and Metabolic Disease, AJH, 20: 1209-1215.*
Deen et al., 2011, Succinate Receptors in the Kidney, JASN, 22: 1416-1422.*
Kinoshita et al., 2014, Cyclic Stretch and Hypertension Increase Retinal Succinate: Potential Mechanisms for Exacerbation of Ocular Neovascularization by Mechanical Stress, Invest Ophthalmol Vis Sci, 55: 4320-4326.*
Cordes et al., 2016, Immunoresponsive Gene 1 and Itaconate Inhibit Succinate Dehydrogenase to Modulate Intracellular Succinate Levels, The Journal of Biological Chemistry, 291(27): 14274-14284.*
Lampropoulou et al., 2016, Itaconate Links Inhibition of Succinate Dehydrogenase with Macrophage Metabolic Remodeling and Regulation of Inflammation, Cell Metab, 24(1): 158-166.*
Mills et al., 2014, Succinate: a metabolic signal in inflammation, Trends in Cell Biology, 24(5): 313-320.*
Yang et al., 2016, The Succinate Receptor GPR91 Is Involved in Pressure Overload-Induced Ventricular Hypertrophy, PLoS One, 11(1): e0147597 (17 pages).*
Littlewood-Evans et al., 2016, GPR91 senses extracellular succinate released from inflammatory macrophages and exacerbates rheumatoid arthritis, J Exp. Med., 213(9): 1655-1662.*

(Continued)

*Primary Examiner* — Amber D Steele
(74) *Attorney, Agent, or Firm* — The Roy Gross Law Firm, LLC; Roy Gross

(57) ABSTRACT

Polypeptides comprising an amino acid sequence of Slc26a6 or IRBIT comprising a mutation that increases NaDC-1 binding, stability of the polypeptide, stability of NaDC-1 complex or a combination thereof are provided. Polypeptides comprising an amino acid sequence of a mutant succinate receptor 1 (mutSUCNR1), comprising a mutation that increases succinate binding, stability of the polypeptide, stability of the mutSUCNR1-succinate complex or combinations thereof are also provided. Compositions comprising the polypeptides, nucleic acid molecules and vectors encoding the polypeptides, and methods of use of the polypeptides or compositions, specifically for treating succinate-associate diseases and conditions are also provided.

11 Claims, 31 Drawing Sheets

Specification includes a Sequence Listing.

(56) References Cited

OTHER PUBLICATIONS

Aguiar et al., 2014, Succinate causes pathological cardiomyocyte hypertrophy through GPR91 activation, Cell Communication and Signaling, 12: 78 (17 pages).*
Ohana et al., 2013, SLC26A6 and NaDC-1 Transporters Interact to Regulate oxalate and Citrate Homeostasis, J Am Soc Nephrol, 24: 1617-1626.*
Ariza et al., 2012, The succinate receptor as a novel therapeutic target for oxidative and metabolic stress-related conditions, Frontiers in Endocrinology, 3(22): 1-8.*
Jiang et al., 2006, Calcium oxalate urolithiasis in mice lacking anion transporter Slc26a6, Nature Genetics, 38(4): 474-478.*
Ando et al., 2014, IRBIT: A regulator of ion channels and ion transporters, Biochimica et Biophysica Acta, 1843: 2195-2204.*
Hadar Eini Rider et al., "Regulation of succinate transport and homeostasis", Proceedings of the 2016 ISPP meeting, p. 12, Feb. 18, 2016.
Ehud Ohana et al., "Physiological Implications of Transepithelial Carboxylic Acid Absorption and Regulation by Slc26a6", Biophysical Journal, vol. 108 Issue 2 p. 461a, 2015.
Nalini Sadagopan et al., "Circulating succinate is elevated in rodent models of hypertension and metabolic disease", American Journal of Hypertension, vol. 20 Issue 11 pp. 1209-1215, 2007.
Julie Gilissen et al., "Insight into SUCNR1 (GPR91) structure and function. Pharmacology & therapeutics", vol. 159 pp. 56-65, 2016.
Ahlam Khamaysi et al., "Systemic Succinate Homeostasis and Local Succinate Signaling Affect Blood Pressure and Modify Risks for Calcium Oxalate Lithogenesis", Journal of the American Society of Nephrology, vol. 30 Issue 3 pp. 381-392, 2019.
G. M. Tannahill et al., "Succinate is an inflammatory signal that induces IL-1β through HIF-1α", Nature, vol. 496 pp. 238-242, 2013.
Edward T. Chouchani et al., "Ischaemic accumulation of succinate controls reperfusion injury through mitochondrial ROS", Nature, vol. 515 pp. 431-435, 2014.
Idikó Toma et al., "Succinate receptor GPR91 provides a direct link between high glucose levels and renin release in murine and rabbit kidney", The Journal of clinical investigation, vol. 118 Issue 7 pp. 2526-2534, 2008.
Ehud Zigmond et al., "Intestinal macrophages: well educated exceptions from the rule", Trends Immunol., vol. 34 Issue 4 pp. 162-168, 2013.
Evanna Mills et al., "Succinate: a metabolic signal in inflammation", Trends Cell Biol, vol. 24 Issue 5 pp. 313-320, 2013.
Ehud Ohana et al., "SLC26A6 and NaDC-1 Transporters Interact to Regulate Oxalate and Citrate Homeostasis", Journal of the American Society of Nephrology, vol. 24 Issue 10 pp. 1617-1626, 2013.
Claire Colas et al., "Structure based identification of inhibitors for the SLC13 family of Na+/dicarboxylate cotransporters", Biochemistry, vol. 54 Issue 31 pp. 4900-4908, 2015.
Amanda Littlewood-Evans et al., "GPR91 senses extracellular succinate released from inflammatory macrophages and exacerbates rheumatoid arthritis", J Exp Med, vol. 213 Issue 9 pp. 1655-1662, 2016.
Nalini Sadagopan et al., "Circulating succinate is elevated in rodent models of hypertension and metabolic disease", Am J Hypertens, vol. 20 Issue 11 pp. 1209-1215, 2007.
Weihai He et al., "Citric acid cycle intermediates as ligands for orphan G-protein-coupled receptors", Nature, vol. 429 Issue 6988 pp. 188-193, 2004.
Carla J Aguiar et al., "Succinate modulates Ca(2+) transient and cardiomyocyte viability through PKA-dependent pathway", Cell Calcium, vol. 47 Issue 1 pp. 37-46, 2010.
Jeong Hee Hong et al, "Convergence of IRBIT, phosphatidylinositol (4,5) bisphosphate, and WNK/SPAK kinases in regulation of the Na+—HCO3-cotransporters family", Proc Natl Acad Sci U S A. Mar. 5, 2013;110(10):4105-10.
International Search Report of PCT/IL2018/051060 Completed Dec. 26, 2018; dated Dec. 31, 2018 2 pages.
Written Opinion of PCT/IL2018/051060 Completed Dec. 26, 2018; dated Dec. 31, 2018 7 pages.

* cited by examiner

Figure 1A continued_1
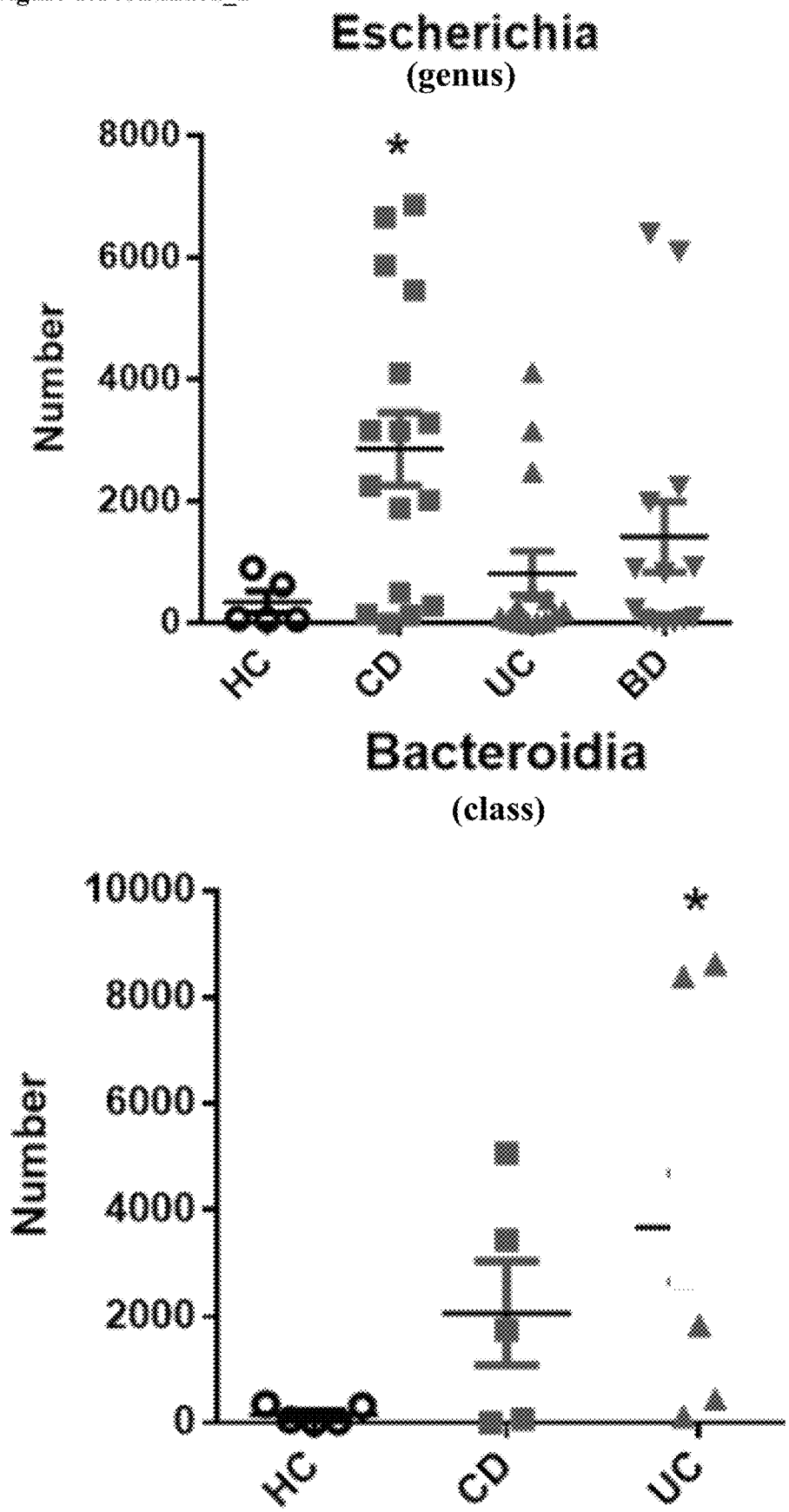

Figure 1A continued_2
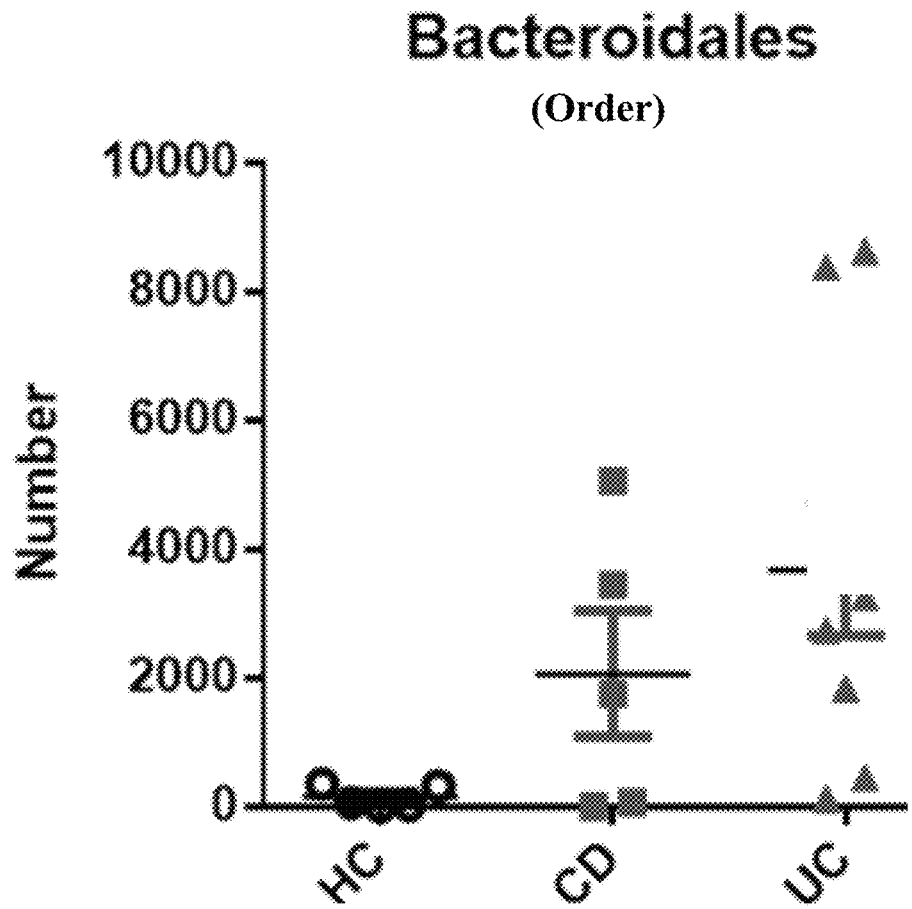
Figure 1B
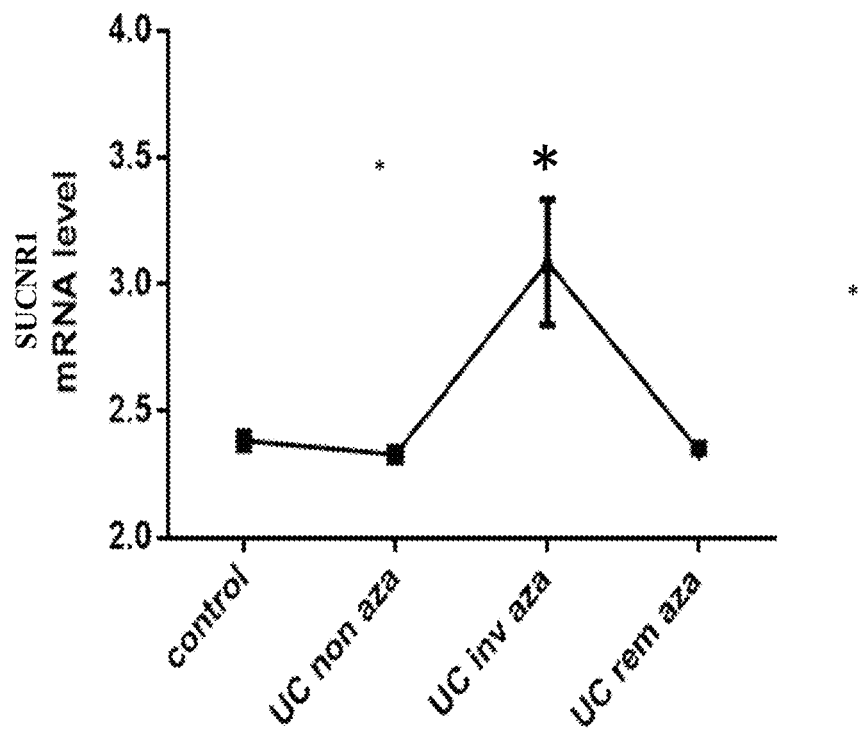

Figure 2C 5 mM succinate

......Initial rates
wildtype 3.83 mmHg/min
slc26a6$^{-/-}$ 7.01 mmHg/min

SUCCINATE-BINDING POLYPEPTIDES AND USE THEREOF

CROSS REFERENCE

This application claims the benefit of priority of U.S. Provisional Patent Application Nos. 62/559,694 filed on Sep. 18, 2017, titled "SUCCINATE-BINDING POLYPEPTIDES AND USE THEREOF", 62/623,825 filed on Jan. 30, 2018, titled "SUCCINATE BASED INFLAMMATORY BOWEL DISEASE DIAGNOSTICS" and 62/623,864 filed on Jan. 30, 2018, titled "NADC-1 INHIBITING POLYPEPTIDES AND USE THEREOF". The contents of which are incorporated herein by reference in their entirety.

FIELD OF INVENTION

The present invention is directed to polypeptides that regulate succinate and their use in treating succinate-related diseases.

BACKGROUND OF THE INVENTION

As originally demonstrated by Krebs, succinate, an intermediate of the tricarboxylic acid (TCA) cycle, rises during hypoxia, while the concentrations of other TCA cycle intermediates drop. More recently, succinate was shown to serve as a universal metabolic marker of ischemia and as a metabolic signaling molecule. Succinate is present in the human circulatory system and urine, with mean plasma succinate concentrations of 1-20 µM. Intriguingly, a succinate-specific G-coupled receptor, designated SUCNR1 or GPR91, was identified in blood vessels, cardiomyocytes and kidney epithelia, suggesting that succinate may function as an essential signaling molecule. When expressed in cell lines, stimulation of the Gq and Gi-coupled SUCNR1 receptor with succinate activates PLCβ to increase the levels of inositol triphosphate (IP3) and the release of Ca2+ from intracellular stores. In contrast, stimulation of SUCNR1 in cardiomyocytes activates PKA to modulate the global Ca2+ transients. Therefore, an important question that arises is how does succinate signaling modulate transepithelial succinate transport to maintain succinate homeostasis? One intracellular multifunctional protein, which regulates ion transporters and may be potentially involved in succinate transport regulation via signaling is IRBIT (IP3 receptor-binding protein released with IP3), that plays a role in diverse physiological functions. IRBIT competes with IP3 in the binding to IP3 receptors and reduces their activity. Furthermore, IRBIT coordinates transepithelial fluid and HCO3− secretion by activating the basolateral sodium bicarbonate cotransporters (NBCs) and the luminal HCO3− transporters CFTR and slc26a6. It is not yet known whether IRBIT regulates succinate transport following stimulation of SUCNR1. To date how succinate's systemic level is modulated, what are the key transporters determining its clearance and how they are regulated are all poorly understood.

It was previously reported that the succinate transporter NaDC-1 forms a complex with Slc26a6, a member of the slc26 family of transporters, which acts as a Cl−-dependent oxalate/HCO3−/OH− exchanger. It was found that slc26a6 strongly inhibits NaDC-1 activity through interaction. slc26a6/NaDC-1 controls citrate absorption which chelates free Ca2+ thus protecting against Ca2+-oxalate stone formation. Moreover, succinate reabsorption by the proximal tubule stimulates SUCNR1 at the juxtaglomerular apparatus and leads to increased renin secretion and hypertension. It is not known if the slc26a6/NaDC-1 complex protects against kidney stone formation and controls blood pressure through metabolic signaling.

In humans, the major apical succinate transporters are members of the slc13 family, which is part of the divalent anion:sodium symporter super-family. The physiological importance of slc13 member 2, NaDC-1, is underscored by the observation that NaDC-1 deletion in mice leads to increased urinary concentrations of carboxylic acids, including succinate, due to failure of reabsorption by the proximal tubules. NaDC-1 functions as an electrogenic Na+-dependent citrate/succinate transporter. In the basolateral membrane of proximal tubule epithelia, NaDC-3 mediates Na+-dependent succinate influx from the interstitium into the cells. The basolateral transporters that mediate succinate extrusion in the proximal tubule are the organic anion transporters (OAT) 1, 2 and 3. The OATs function as exchangers that mediate the inward transport of organic anions in exchange for the extrusion of succinate and other metabolic products into the blood. It is not known what regulates and orchestrates succinate transport via NaDC-1, NaDC-3 and OAT transporters.

SUMMARY OF THE INVENTION

The present invention provides polypeptides comprising an amino acid sequence of Slc26a6 or IRBIT comprising a mutation that increases NaDC-1 binding, stability of the polypeptide, stability of NaDC-1 complex or a combination thereof are provided. Polypeptides comprising an amino acid sequence of a mutant succinate receptor 1 (mutSUCNR1), the mutSUCNR1 comprises a mutation that increases succinate binding, stability of the polypeptide, stability of the mutSUCNR1-succinate complex as compared to non-mutant SUCNR1 or combinations thereof are also provided. Compositions comprising the polypeptides, nucleic acid molecules and vectors encoding the polypeptides, and methods of use of the polypeptides or compositions, specifically for treating succinate-associate diseases and/or conditions, are also provided.

According to a first aspect, there is provided a method of treating or preventing a succinate-associated disease or condition in a subject in need thereof, the method comprising decreasing serum succinate levels in the subject, thereby treating or preventing a succinate-associated disease or condition.

According to another aspect, there is provided a method of diagnosing increased levels of serum succinate in a subject, the method comprising obtaining a urine sample from the subject and measuring succinate levels in the urine sample, wherein a decrease in urine succinate levels as compared to a healthy control indicates an increase in serum succinate levels in the subject.

According to another aspect, there is provided polypeptide comprising a. an amino acid sequence of a mutant Slc26a6 (mutSlc26a6) or mutant IP(3)R binding protein released with IP(3) (mutIRBIT), the mutSlc26a6 or mutIRBIT comprising at least one mutation which:

i. increases binding of the polypeptide to NaDC-1 as compared to a non-mutant Slc26a6 or IRBIT, ii. increases stability of the polypeptide as compared to a non-mutant Slc26a6 or IRBIT, iii. increases stability of a mutSlc26a6-NaDC-1 complex or a mutIRBIT-NaDC-1 complex as compared to a non-mutant Slc26a6-NaDC-1 complex or a non-mutant IRBIT-NaDC-1 complex, or
iv. any combination thereof;
b. an amino acid sequence of a mutant succinate receptor 1 (mutSUCNR1), the mutSUCNR1 comprising at least one mutation which:
i. increases binding of the polypeptide to succinate as compared to a non-mutant SUCNR1,
ii. increases stability of the polypeptide as compared to a non-mutant SUCNR1,
iii. increases stability of a mutSUCNR1-succinate complex as compared to a non-mutant SUCNR1-succinate complex, or
iv. any combination thereof.

According to another aspect, there is provided a nucleic acid molecule coding for a polypeptide of the invention.

According to another aspect, there is provided a vector comprising a nucleic acid molecule of the invention.

According to another aspect, there is provided a pharmaceutical composition comprising a pharmaceutically acceptable carrier, excipient or adjuvant and the polypeptide of the invention.

According to another aspect, there is provided a method of increasing succinate reabsorption from urine in a subject in need thereof, the method comprising at least one of:
a. inhibiting interaction between NaDC-1 and IRBIT in the subject; and
b. inhibiting electrostatic interaction between the STAS domain of Slc26a6 and the H4c domain of NaDC-1,
thereby increasing succinate reabsorption in a subject in need thereof.

According to some embodiments, the succinate-associated disease or condition is selected from inflammatory bowel disease (IBD), urolithiasis, rheumatoid arthritis, cardiac hypertrophy, inflammation, kidney stones and hypertension. According to some embodiments, the succinate-associated disease or condition is selected from IBD, kidney stones and hypertension. According to some embodiments, the IBD is selected from any one of: colitis, ulcerative colitis, Crohn's disease, and Bechet's disease. According to some embodiments, the inflammatory bowel disease further comprises at least one of: kidney stones, hypertension, arthritis, non-alcoholic fatty liver diseases (NAFLD), non-alcoholic steatohepatitis (NASH) and primary sclerosing cholangitis and cholestasis. According to some embodiments, the hypertension is dependent on sodium intake.

According to some embodiments, the decreasing serum succinate levels comprises administering succinate receptor 1 (SUCNR1) or a fragment, derivative, analog or mutant thereof, capable of binding succinate. According to some embodiments, the decreasing serum succinate levels comprises decreasing solute carrier family 13 member 2 (NaDC-1) transport of succinate.

According to some embodiments, decreasing NaDC-1 transport of succinate comprises increasing binding of NaDC-1 to solute carrier family 26 member 6 (Slc26a6), IP3 receptor-binding protein released with IP3 (IRBIT) or both. According to some embodiments, increasing binding to Slc26a6 comprises increasing electrostatic interaction between a STAS domain of Slc26a6 and a H4c domain of NaDC-1. According to some embodiments, the increasing electrostatic interaction comprises increasing negative charge in the Slc26a6-STAS domain.

According to some embodiments, the increasing binding of NaDC-1 to Slc26a6, IRBIT or both comprises administering to the subject a polypeptide comprising an amino acid sequence of:
a. a Slc26a6 STAS domain, or a fragment, derivative or analog thereof, capable of binding NaDC-1, and comprising glutamic acid 613 or aspartic acid 637; or
b. IRBIT or a fragment, derivative or analog thereof capable of binding NaDC-1.

According to some embodiments, the polypeptide comprises an amino acid sequence of a mutant Slc26a6 (mutSlc26a6) or mutant IRBIT (mutIRBIT), the mutSlc26a6 or mutIRBIT comprising at least one mutation which increases binding of the polypeptide to NaDC-1 as compared to a non-mutant Slc26a6 or IRBIT, increases stability of the polypeptide as compared to a non-mutant Slc26a6 or IRBIT, increases stability of a mutSlc26a6-NaDC-1 complex or a mutIRBIT-NaDC-1 complex as compared to a non-mutant Slc26a6-NaDC-1 complex or a non-mutant IRBIT-NaDC-1 complex, or any combination thereof.

According to some embodiments, the amino acid sequence of Slc26a6 is SEQ ID NO: 1 or SEQ ID NO: 2. According to some embodiments, the amino acid sequence of IRBIT is SEQ ID NO: 3 or SEQ ID NO: 4. According to some embodiments, the NaDC-1 comprises the amino acid sequence provided in SEQ ID NO: 5 or SEQ ID NO: 6 and the at least one mutation increases binding to lysine 107, arginine 108, or both of SEQ ID NO: 5 or lysine 156, arginine 157, or both of SEQ ID NO: 6.

According to some embodiments, the method of the invention is for diagnosing an increased risk of a succinate-associated disease or condition in the subject.

According to some embodiments, the at least one mutation increases negative charge in the Slc26a6-STAS domain. According to some embodiments, the at least one mutation increases electrostatic interaction between Slc26a6 and NaDC-1. According to some embodiments, the at least one mutation of Slc26a6 is mutation of glutamic acid 613 of SEQ ID NO: 1 or aspartic acid 637 of SEQ ID NO: 2. According to some embodiments, the at least one mutation is within the IRBIT PEST domain or PDZ-binding domain.

According to some embodiments, the NaDC-1 comprises the amino acid sequence provided in SEQ ID NO: 5 or SEQ ID NO: 6 and the at least one mutation increases binding to lysine 107 and/or arginine 108 of SEQ ID NO: 5 or lysine 156 and/or arginine 157 of SEQ ID NO: 6.

According to some embodiments, an amino acid sequence of SUCNR1 is SEQ ID NO: 7, and wherein the at least one mutation is selected from the group consisting of: Leucine 191, Threonine 192, Glycine 195, Isoleucine 110, Phenylalanine 241, Methionine 203, Valine 238, Tyrosine 207, Arginine 120, Arginine 281, Phenylalanine 285, Asparagine 287, Tyrosine 295, or any combination thereof.

According to some embodiments, the increase is at least a 10% increase.

According to some embodiments, increased stability comprises increased stability in a solution. According to some embodiments, the solution is selected from at least one of: blood, serum, gastric fluid, intestinal fluid, saliva, bile, urine and stool.

According to some embodiments, the pharmaceutical compositions of the invention are for use
a. in treating a succinate-associated disease or condition in a subject;
b. decreasing serum succinate levels in a subject; or
c. decreasing NaDC-1 mediated transport or succinate.

According to some embodiments, the inhibiting electrostatic interaction comprises blocking interaction of E613 or D637 of Slc26a6 with the H4c domain of NaDC-1. According to some embodiments, inhibiting electrostatic interaction comprises blocking interaction of K107, R108, K156 and/or R157 of NaDC-1 with the STAS domain of Slc26a6. According to some embodiments, blocking interaction comprises mutation of at least one of amino acids E613 and D637 of Slc26a6, and K107, R108, K156 and R157 of NaDC-1. According to some embodiments, the mutation is to alanine. According to some embodiments, inhibiting interaction comprises contacting with a blocking antibody or antibody fragment.

According to some embodiments, the methods of the invention are for treating or preventing hypotension.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description together with the drawings makes apparent to those skilled in the art how embodiments of the invention may be practiced.

FIGS. 1A-J: (1A) Dot plots of the numbers of various types of microbiota found in the stool from healthy, Crohn's disease (CD), ulcerative colitis (UC) and Bechet's disease (BD) patients. (1B) Line graph showing the mRNA levels of SUCNR1 are elevated in damaged mucosa (involved=inv) of UC patients treated with aza compared to non-involved tissue (non), patients in remission (rem) or healthy volunteers (control). (1C-D) Line graphs showing the mRNA levels of (1C) the succinate transporter NaDC-1 (SLC13A2) were lower in damaged mucosa compared to all others, while the mRNA levels of (1D) another succinate transporter (slc13a3) were not changed, suggesting that NaDC-1 may be the dominant transporter. (1E) Bar chart showing a significant increase in succinate uptake by mouse M1 macrophages compared to M1 and M2 macrophages. (1F-G) Bar chart showing that in the human system, levels of SUCNR1 mRNA is increased in (1F) anti-inflammatory M2 macrophages, and (1G) mononuclear cells treated with anti-inflammatory IL-10. *P<0.05, P<0.005, *P<0.001. (1H-I) Dot plots showing succinate levels in stool from (1H) control and DSS-treated mice and (1I) healthy, Crohn's disease (CD) and ulcerative colitis (UC) patient. (1J) Bar chart showing the average succinate levels from FIG. 1I.

FIGS. 2A-C: Model of NaDC-1 and slc26a6/STAS interaction sites. (2A and B) Cartoon representation of NaDC-1 (cyan, above) and a surface representation of slc26a6-STAS (Red/blue, bellow. (2A) Cartoon showing an electrostatics analysis (blue: positive, red: negative) and (2B) showing slc26a6(E613) (red) and NaDC-1 (K107, R108) (blue). (2C) Multiple sequence alignment of slc13 and slc26 transporters. Specific charged amino acids that may mediate the NaDC-1-slc26a6 interaction are indicated by arrows.

DETAILED DESCRIPTION OF THE INVENTION

Figure 1A:
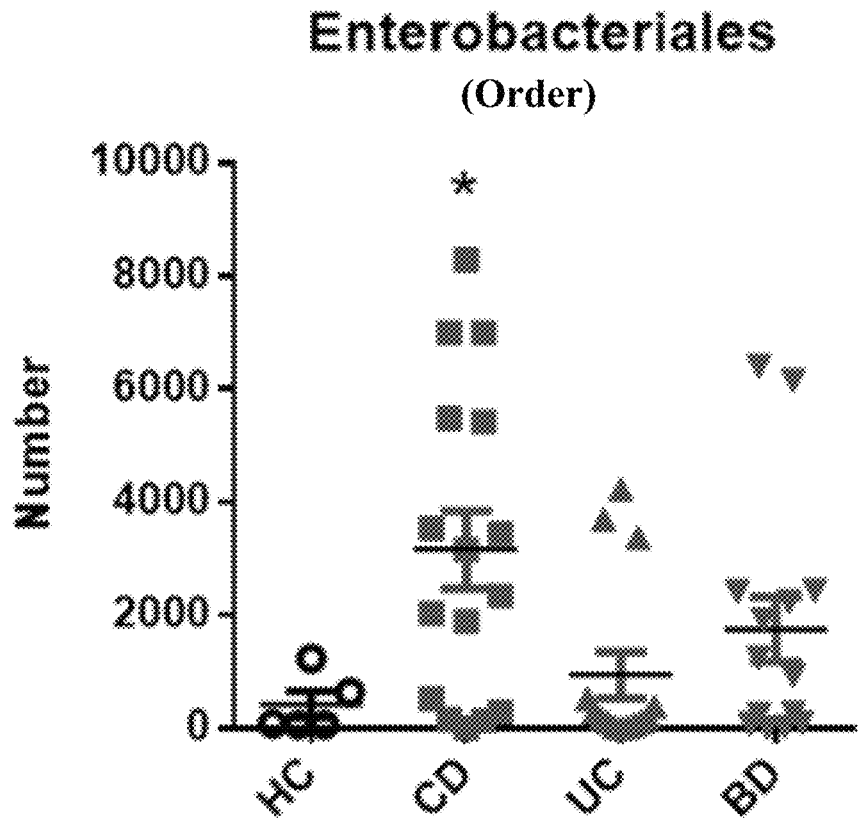
Figure 1A:
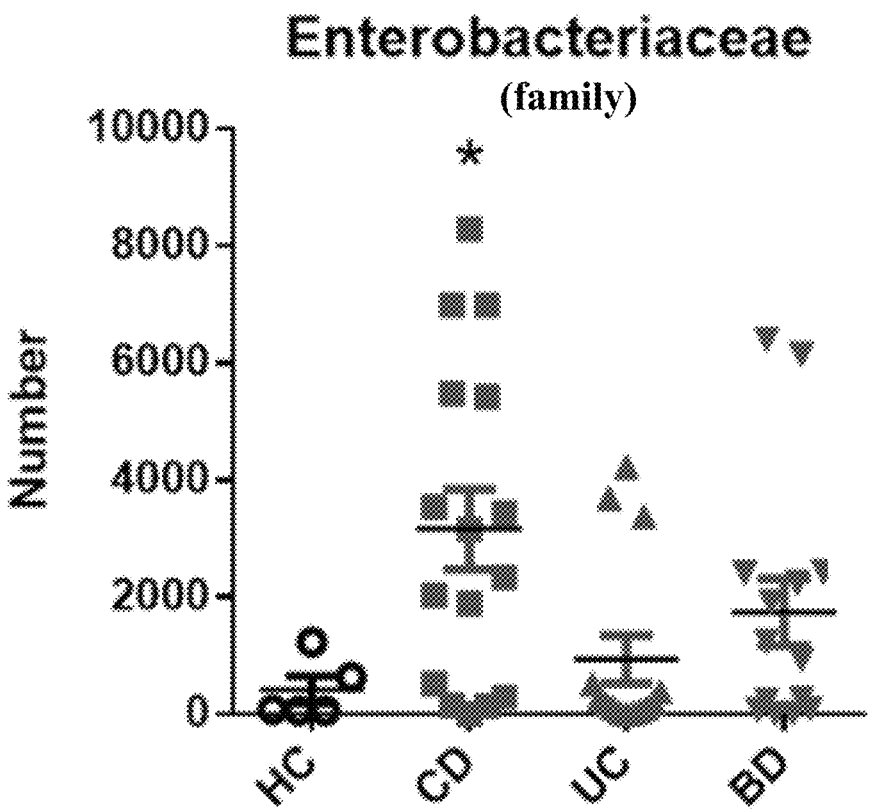

The present invention, in some embodiments, provides polypeptides comprising an amino acid sequence of Slc26a6 or IRBIT comprising a mutation that increases NaDC-1 binding, stability of the polypeptide, stability of NaDC-1 complex or a combination thereof are provided. Polypeptides comprising an amino acid sequence of a mutant succinate receptor 1 (mutSUCNR1), the mutSUCNR1 comprises a mutation that increases succinate binding, stability of the polypeptide, stability of the mutSUCNR1-succinate complex as compared to non-mutant SUCNR1 or combinations thereof are also provided. Compositions comprising the polypeptides, nucleic acid molecules and vectors encoding the polypeptides, and methods of use of the polypeptides or compositions, specifically for treating succinate-associate diseases and conditions are also provided.

By one aspect, the present invention provides a polypeptide comprising an amino acid sequence of a mutant solute carrier family 26 member 6 (mutSlc26a6), the mutSlc26a6 comprises at least one mutation which increases binding of the polypeptide to NaDC-1 as compared to a non-mutant Slc26a6, increases stability of the polypeptide as compared to a non-mutant Slc26a6, increases stability of a mutSlc26a6-NaDC-1 complex as compared to a non-mutant Slc26a6-NaDC-1 complex, or any combination thereof.

By another aspect, the present invention provides a NaDC-1 inhibitory polypeptide comprising an amino acid sequence of a mouse Slc26a6 STAS domain, or a fragment, derivative or analog thereof, capable of binding NaDC-1, and comprising glutamic acid 613.

By another aspect, the present invention provides a NaDC-1 inhibitory polypeptide comprising an amino acid sequence of a human Slc26a6 STAS domain, or a fragment, derivative or analog thereof, capable of binding NaDC-1, and comprising aspartic acid 637.

By another aspect, the present invention provides a NaDC-1 inhibitory polypeptide comprising an amino acid sequence of IRBIT or a fragment, derivative or analog thereof capable of binding NaDC-1.

By another aspect, the present invention provides a polypeptide comprising an amino acid sequence of a mutant S-adenosylhomocysteine hydrolase-like protein (mutIRBIT), the mutIRBIT comprises at least one mutation which increases binding of the polypeptide to NaDC-1 as compared to a non-mutant IRBIT, increases stability of the polypeptide as compared to a non-mutant IRBIT, increases stability of a mutIRBIT-NaDC-1 complex as compared to a non-mutant IRBIT-NaDC-1 complex, or any combination thereof.

By another aspect, the present invention provides a polypeptide comprising an amino acid sequence of a mutant succinate receptor 1 (mutSUCNR1), said mutSUCNR1 comprises at least one mutation which increases binding of said polypeptide to succinate as compared to a non-mutant SUCNR1, increases stability of said polypeptide as compared to a non-mutant SUCNR1, increases stability of a mutSUCNR1-succinate complex as compared to a non-mutant SUCNR1-succinate complex, or any combination thereof.

By another aspect, the present invention provides a polypeptide comprising an amino acid sequence of succinate receptor 1 (SUCNR1), or a fragment, derivative or analog thereof, capable of binding succinate, and at least one mutation of the sequence which increases binding of the polypeptide to succinate, increases the stability of the polypeptide in solution, increases stability of the receptor-succinate complex or any combination thereof.

In some embodiments, the polypeptide comprises an amino acid sequence of a mutant solute carrier family 26 member 6 (mutSlc26a6), the mutSlc26a6 comprises at least one mutation which increases binding of the polypeptide to NaDC-1 as compared to a non-mutant Slc26a6, increases stability of a mutSlc26a6-NaDC-1 complex as compared to a non-mutant Slc26a6-NaDC-1 complex, or any combination thereof.

In some embodiments, the polypeptide comprises an amino acid sequence of a mutant S-adenosylhomocysteine hydrolase-like protein (mutIRBIT), the mutIRBIT comprises at least one mutation which increases binding of the polypeptide to NaDC-1 as compared to a non-mutant IRBIT, increases stability of a mutIRBIT-NaDC-1 complex as compared to a non-mutant IRBIT-NaDC-1 complex, or any combination thereof.

As used herein, the terms "peptide", "polypeptide" and "protein" are used interchangeably to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides, polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

In some embodiments, the polypeptides of the invention are isolated polypeptides. As used herein, the term "isolated polypeptide" refers to a peptide that is essentially free from contaminating cellular components, such as carbohydrate, lipid, or other proteinaceous impurities associated with the peptide in nature. Typically, a preparation of isolated peptide contains the peptide in a highly-purified form, i.e., at least about 80% pure, at least about 90% pure, at least about 95% pure, greater than 95% pure, or greater than 99% pure. Each possibility represents a separate embodiment of the invention.

In some embodiments, the polypeptides of the invention are recombinant proteins. As used herein, the term "recombinant protein" refers to protein, which is coded for by a recombinant DNA, and is thus not naturally occurring. In some embodiments, the isolated polypeptide is a recombinant protein. In some embodiments, the isolated polypeptide is mutSUCNR1. The term "recombinant DNA" refers to DNA molecules formed by laboratory methods of genetic recombination. Generally, this recombinant DNA is in the form of a vector used to express the recombinant protein in a cell.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Common expression vectors of utility in recombinant DNA techniques are often in the form of plasmids.

Recombinant expression vectors can comprise a nucleic acid coding for the protein of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), heat shock, infection by viral vectors, high velocity ballistic penetration by small particles with the nucleic acid either within the matrix of small beads or particles, or on the surface (Klein et al., Nature 327. 70-73 (1987)), and/or the like.

General methods in molecular and cellular biochemistry, such as may be useful for carrying out DNA and protein recombination, as well as other techniques described herein, can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

It should be well understood to a person of skill in the art that a recombinant protein is produced by expressing the recombinant DNA in a cell and then purifying the protein. The cells expressing the DNA are cultured under effective conditions, which allow for the expression of high amounts of recombinant polypeptide. Such effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

Purification of a recombinant protein involves standard laboratory techniques for extracting a recombinant protein that is essentially free from contaminating cellular components, such as carbohydrate, lipid, or other proteinaceous impurities associated with the peptide in nature. Purification can be carried out using a tag that is part of the recombinant protein or thought immuno-purification with antibodies directed to the recombinant protein. In some embodiments, the polypeptides of the invention comprise a Flag tag for purification. Kits are commercially available for such purifications and will be familiar to one skilled in the art. Typically, a preparation of purified peptide contains the peptide in a highly-purified form, i.e., at least about 80% pure, at least about 90% pure, at least about 95% pure, greater than 95% pure, or greater than 99% pure. Each possibility represents a separate embodiment of the invention.

Mutations and deletions in a protein are created by introducing the mutation or deletion into the coding DNA. Methods of site-directed mutagenesis, and routine DNA recombination can be found in such standard textbooks as are enumerated above. Mutagenesis of one amino acid to another may require mutation of 1, 2, or 3 of the bases that make up the codon corresponding to the amino acid to be changed.

By another aspect, the invention provides in some embodiments, a nucleic acid molecule coding for any one of the polypeptides of the invention.

By another aspect, the invention provides a vector comprising a nucleic acid molecule of the invention.

In some embodiments, non-mutated Slc26a6 is mammalian Slc26a6. In some embodiments, Slc26a6 is mouse Slc26a6. In some embodiments, non-mutated mouse Slc26a6 has the amino acid sequence provided in NCBI Reference Sequence: NP_599252.2. In some embodiments, mouse Slc26a6 has the following amino acid sequence:

(SEQ ID NO: 1)
MELQRRDYHVERPLLNQEQLEDLGHWGPAAKTHQWRTWFRCSRARAHSLLL

QHVPVLGWLPRYPVREWLLGDLLSGLSVAIMQLPQGLAYALLAGLPPMFGL

YSSFYPVFIYFLFGTSRHISVGTFAVMSVMVGSVTESLTADKAFVQGLNAT

ADDARVQVAYTLSFLVGLFQVGLGLVHFGFVVTYLSEPLVRSYTTAASVQV

LVSQLKYVFGIKLSSHSGPLSVIYTVLEVCAQLPETVPGTVVTAIVAGVAL

VLVKLLNEKLHRRLPLPIPGELLTLIGATGISYGVKLNDRFKVDVVGNITT

GLIPPVAPKTELFATLVGNAFAIAVVGFAIAISLGKIFALRHGYRVDSNQE

LVALGLSNLIGGFFQCFPVSCSMSRSLVQESTGGNTQVAGAVSSLFILLII

VKLGELFRDLPKAVLAAVIIVNLKGMMKQFSDICSLWKANRVDLLIWLVTF

VATILLNLDIGLAVSIVFSLLLVVVRMQLPHYSVLGQVPDTDIYRDVAEYS

GAKEVPGVKVFRSSATLYFANAELYSDSLKEKCGVDVDRLITQKKKRIKKQ

EMKLKRMKKAKKSQKQDASSKISSVSVNVNTNLEDVKSNDVEGSEAKVHQG

EELQDVVSSNQEDAKAPTMTSLKSLGLPQPGFHSLILDLSTLSFVDTVCIK

SLKNIFRDFREIEVEVYIAACYSPVVAQLEAGHFFDESITKQHVFASVHDA

VTFALSHRKSVPKSPVLATKL.

In some embodiments, an amino acid sequence of non-mutated Slc26a6 is SEQ ID NO: 1.

In some embodiments, Slc26a6 is human Slc26a6. In some embodiments, non-mutated human Slc26a6 is any one of Slc26a6 splice isoforms 1 to 6. In some embodiments, non-mutated human Slc26a6 has the amino acid sequence provided in any one of NCBI Reference Sequences: AAK19153.1, NP_075062.2, NP_599025.2, NP_602298.2, NP_001035544.1, NP_001268661.1, and NP_001268662.1.

In some embodiments, non-mutated human Slc26a6 has the amino acid sequence provided in NCBI Reference Sequence: NP_075062.2. In some embodiments, human Slc26a6 has the following amino acid sequence:

(SEQ ID NO: 2)
MGLADASGPRDTQALLSATQAMDLRRRDYHMERPLLNQEHLEELGRWGSAP

RTHQWRTWLQCSRARAYALLLQHLPVLVWLPRYPVRDWLLGDLLSGLSVAI

MQLPQGLAYALLAGLPPVFGLYSSFYPVFIYFLFGTSRHISVGTFAVMSVM

VGSVTESLAPQALNDSMINETARDAARVQVASTLSVLVGLFQVGLGLIHFG

FVVTYLSEPLVRGYTTAAAVQVFVSQLKYVFGLHLSSHSGPLSLIYTVLEV

CWKLPQSKVGTVVTAAVAGVVLVVVKLLNDKLQQQLPMPIPGELLTLIGAT

GISYGMGLKHRFEVDVVGNIPAGLVPPVAPNTQLFSKLVGSAFTIAVVGFA

IAISLGKIFALRHGYRVDSNQELVALGLSNLIGGIFQCFPVSCSMSRSLVQ

ESTGGNSQVAGAISSLFILLIIVKLGELFHDLPKAVLAAIIIVNLKGMLRQ

LSDMRSLWKANRADLLIWLVTFTATILLNLDLGLVVAVIFSLLLVVVRTQM

PHYSVLGQVPDTDIYRDVAEYSEAKEVRGVKVFRSSATVYFANAEFYSDAL

KQRCGVDVDFLISQKKKLLKKQEQLKLKQLQKEEKLRKQAASPKGASVSIN

VNTSLEDMRSNNVEDCKMMQVSSGDKMEDATANGQEDSKAPDGSTLKALGL

PQPDFHSLILDLGALSFVDTVCLKSLKNIFHDFREIEVEVYMAACHSPVVS

QLEAGHFFDASITKKHLFASVHDAVTFALQHPRPVPDSPVSVTRL.

In some embodiments, an amino acid sequence of non-mutated Slc26a6 is SEQ ID NO: 2. In some embodiments, Slc26a6 does not comprise a signal peptide. In some embodiments, Slc26a6 is membranal Slc26a6. In some embodiments, Slc26a6 is a soluble Slc26a6.

As used herein, "S-adenosylhomocysteine hydrolase-like protein" is also known as Inositol 1,4,5-triphosphate (IP3) receptor-binding protein released with IP3, and also as IRBIT. The three names are synonymous and used interchangeably herein. In some embodiments, non-mutated IRBIT is mammalian IRBIT. In some embodiments, IRBIT is mouse IRBIT. In some embodiments, mouse IRBIT is any one of mouse IRBIT splice isoforms 1-4. In some embodiments, non-mutated mouse IRBIT has the amino acid sequence provided in anyone of NCBI Reference Sequences: NP_663517.2, NP_001344039.1, NP_001344041.1, and NP_001244042.1. In some embodiments, non-mutated mouse IRBIT has the amino acid sequence provided in NCBI Reference Sequence: NP_663517.2. In some embodiments, mouse Slc26a6 has the following amino acid sequence:

(SEQ ID NO: 3)
MSMPDAMPLPGVGEELKQAKEIEDAEKYSFMATVTKAPKKQIQFADDMQEF

TKFPTKTGRRSLSRSISQSSTDSYSSAASYTDSSDDEVSPREKQQTNSKGS

SNFCVKNIKQAEFGRREIEIAEQDMSALISLRKRAQGEKPLAGAKIVGCTH

ITAQTAVLIETLCALGAQCRWSACNIYSTQNEVAAALAEAGVAVFAWKGES

EDDFWWCIDRCVNMDGWQANMILDDGGDLTHWVYKKYPNVFKKIRGIVEES

VTGVHRLYQLSKAGKLCVPAMNVNDSVTKQKFDNLYCCRESILDGLKRTTD

VMFGGKQVVVCGYGEVGKGCCAALKALGAIVYITEIDPICALQACMDGFRV

-continued

```
VKLNEVIRQVDVVITCTGNKNVVTREHLDRMKNSCIVCNMGHSNTEIDVTS

LRTPELTWERVRSQVDHVIWPDGKRVVLLAEGRLLNLSCSTVPTFVLSITA

TTQALALIELYNAPEGRYKQDVYLLPKKMDEYVASLHLPSFDAHLTELTDD

QAKYLGLNKNGPFKPNYYRY.
```

In some embodiments, an amino acid sequence of non-mutated IRBIT is SEQ ID NO: 3.

In some embodiments, IRBIT is human IRBIT. In some embodiments, non-mutated human IRBIT is any one of IRBIT isoforms a orb. In some embodiments, non-mutated human IRBIT has the amino acid sequence provided in any one of NCBI Reference Sequences: NP_006612.2, and NP_001229602.1. In some embodiments, non-mutated human IRBIT has the amino acid sequence provided in NCBI Reference Sequence: NP_006612.2. In some embodiments, human IRBIT has the following amino acid sequence:

```
                                       (SEQ ID NO: 4)
MSMPDAMPLPGVGEELKQAKEIEDAEKYSFMATVTKAPKKQIQFADDMQEF

TKFPTKTGRRSLSRSISQSSTDSYSSAASYTDSSDDEVSPREKQQTNSKGS

SNFCVKNIKQAEFGRREIEIAEQDMSALISLRKRAQGEKPLAGAKIVGCTH

ITAQTAVLIETLCALGAQCRWSACNIYSTQNEVAAALAEAGVAVFAWKGES

EDDFWWCIDRCVNMDGWQANMILDDGGDLTHWVYKKYPNVFKKIRGIVEES

VTGVHRLYQLSKAGKLCVPAMNVNDSVTKQKFDNLYCCRESILDGLKRTTD

VMFGGKQVVVCGYGEVGKGCCAALKALGAIVYITEIDPICALQACMDGFRV

VKLNEVIRQVDVVITCTGNKNVVTREHLDRMKNSCIVCNMGHSNTEIDVTS

LRTPELTWERVRSQVDHVIWPDGKRVVLLAEGRLLNLSCSTVPTFVLSITA

TTQALALIELYNAPEGRYKQDVYLLPKKMDEYVASLHLPSFDAHLTELTDD

QAKYLGLNKNGPFKPNYYRY.
```

In some embodiments, an amino acid sequence of non-mutated IRBIT is SEQ ID NO: 4.

The term "fragment" as used herein, refers to a portion of the polypeptide, but a portion that still is capable of binding succinate or still comprises the succinate binding pocket. Such a fragment will still be recognizable as being from the polypeptide of the invention, and as such will be at least 10 amino acids in length. As such, any fragment of the isolated polypeptide of the invention will still comprise at least 10, at least 20, at least 30, at least 40, at least 50, at least 80, or at least 100 amino acids surrounding position 232. Each possibility represents a separate embodiment of the present invention.

The term "derivative" as used herein, refers to any polypeptide that is based off the polypeptide of the invention and still is capable of binding succinate or still comprises the succinate binding pocket. A derivative is not merely a fragment of the polypeptide, nor does it have amino acids replaced or removed (an analog), rather it may have additional modification made to the polypeptide, such as post-translational modification. Further, a derivative may be a derivative of a fragment of the polypeptide of the invention, however, in such a case the fragment must comprise at least 50 consecutive amino acids of the polypeptide of the invention.

The term "analog" as used herein, refers to a polypeptide that is similar, but not identical, to the polypeptide of the invention that still is capable of binding succinate or still comprises the succinate binding pocket. An analog, may have deletions or mutations that result in an amino acids sequence that is different than the amino acid sequence of the polypeptide of the invention. In some embodiments, an analog comprises one or more residues that have been conservatively substituted with a functionally similar residue. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

It should be understood that all analogs of the polypeptide of the invention would still be capable of binding NaDC-1 or succinate or still comprise the NaDC-1 binding surface or the succinate binding pocket. Further, an analog may be analogous to a fragment of the polypeptide of the invention, however, in such a case the fragment must comprise at least 50 consecutive amino acids of the polypeptide of the invention.

In some embodiments, the fragment, derivative, or analog of Slc26a6 comprises the STAS domain. In some embodiments, the fragment, derivative, or analog of Slc26a6 STAS domain comprises a positive charge. In some embodiments, the Slc26a6 STAS is mouse Slc26a6 STAS. In some embodiments, mouse Slc26a6 STAS domain comprises the C-terminal 211 amino acids. In some embodiments, the Slc26a6 STAS domain comprises amino acids 531-741 of SEQ ID NO: 2. In some embodiments, Slc26a6 STAS is human Slc26a6 STAS. In some embodiments, the human Slc26a6 STAS domain comprises the C-terminal 213 amino acids. In some embodiments, the human Slc26a6 STAS domain comprises amino acids 530-742 of SEQ ID NO: 4. In some embodiments, the fragment, derivative, or analog of Slc26a6 is capable of binding NaDC-1 and comprises aspartic acid 637 of a human Slc26a6 STAS domain or glutamic acid 613 of a mouse Slc26a6 STAS domain. In some embodiments, the above described negatively charged amino acid is a glutamic acid or an aspartic acid. In some embodiments, amino acid 613 or 637 are any negatively charged amino acid.

In some embodiments, an analog to the polypeptide of the invention comprises an amino acid sequence with at least 60%, at least 65%, at least 70%, at least 75%, at least 80%, at least 85%, at least 90%, at least 95%, or at least 99% homology to the amino acid sequence presented in any one of SEQ ID NOs: 1-4. Each possibility represents a separate embodiment of the invention.

In some embodiments, a fragment of Slc26a6 comprises substantially the STAS domain. In some embodiments, a fragment of Slc26a6 comprises a transmembrane domain and the STAS domain. In some embodiments, a fragment of Slc26a6 comprises a fragment of the STAS domain comprising a negative charge. In some embodiments, a fragment of Slc26a6 comprises a fragment of the STAS domain comprising amino acids 550-700, 600-700, 550-650 or 600-650. Each possibility represents a separate embodiment of the invention. In some embodiments, a fragment of mouse Slc26a6 comprises a fragment of the STAS domain comprising glutamic acid 613. In some embodiments, a fragment of human Slc26a6 comprises a fragment of the STAS domain comprising aspartic acid 637.

In some embodiments, the polypeptide comprises a mutated STAS domain of Slc26a6. In some embodiments, the polypeptide comprises a mutated transmembrane domain (TM) of Slc26a6. In some embodiments, the polypeptide comprises a mutated PEST domain of IRBIT. In some embodiments, the polypeptide comprises a mutated PDZ-binding domain of IRBIT. In some embodiments, the polypeptide comprises a mutated NAD-binding domain of IRBIT.

In some embodiments, the at least one mutation increases negative charge in the Slc26a6 STAS domain. In some embodiments, the at least one mutation increases electrostatic interaction between SLC26a6 and NaDC-1. Amino acid charge is well known in the art and polypeptide charge can be calculated by summing the charges of all amino acids present in the polypeptide. Models for electrostatic interaction are well known in the art, and such interactions can be calculated for instance with HADDOCK software. In some embodiments, the at least one mutation is mutation of glutamic acid 613 of SEQ ID NO: 1 or aspartic acid 637 of SEQ ID NO: 2. In some embodiments, the at least one mutation is mutation of glutamic acid 613 of SEQ ID NO: 1 to aspartic acid. In some embodiments, the at least one mutation is mutation of amino acids proximal to glutamic acid 613 or aspartic acid 637 that increases the negative charge of the polypeptide or increases electrostatic interaction of the polypeptide with NaDC-1. In some embodiments, proximal amino acids are amino acids at most 1, 3, 5, 10, 15, 20, 25, 30, 35, 40, 45 or 50 amino acids upstream or downstream. Each possibility represents a separate embodiment of the invention.

As used herein, "NaDC-1" refers to Solute carrier family 13 member 2 (Slc13a2). In some embodiments, NaDC-1 is mammalian NaDC-1. In some embodiments, NaDC-1 is mouse NaDC-1. In some embodiments, mouse NaDC-1 has the amino acid sequence provided in NCBI Reference Sequence: NP_071856.1. In some embodiments, mouse NaDC-1 has the following amino acid sequence:

(SEQ ID NO: 5)
MATCWQALWAYRSYLIVLCLPIFLLPLPLIVQTKEAYCAYSIILMALLWCT

EALPLAVTALFPIILFPLMGIMEASKVCLEYFKDTNILFVGGLMVAIAVEH

WNLHKRIALGVLLIIGVRPALLLLGFMLVTAFLSMWISNTATTAMMLPIGY

AVLEQLQGSQKDVEEGNSNPSFELQEASPQKEETKLDNGQAVSVSSEPRAQ

KTKEHHRFSQGLSLCICYSASIGGIATLTGTTPNLVLQGQVNSIFPENSNV

VNFASWFGFAFPTMVILLLLAWLWLQVLFLGVNFRKNFGFGEGEEERKQAA

FQVIKTQHRLLGPMSFAEKAVTFLFVLLVVLWFTREPGFFPGWGDTAFANK

GQSMVSDGTVAIFISLIMFIIPSKIPGLTEDPKKPGKLKAPPAILTWKTVN

DKMPWNILILLGGGFALAKGSEESGLSKWLGDKLTPLQHVPPSATVLILSL

LVAIFTECTSNVATTTLFLPILASMAQAICLHPLYVMLPCTLAASLAFMLP

VATPPNAIVFSFGGLKVSDMARAGFLLNIIGVLTITLSINSWSIPIFKLDT

FPTWAYSNTSQCLLNPPNSTVPGH.

In some embodiments, NaDC-1 is human NaDC-1. In some embodiments, human NaDC-1 is any one of isoforms a, b, d or e. In some embodiments, human NaDC-1 has the amino acid sequence provided in any one of NCBI Reference Sequences: NP_001139447.1, NP_003975.1, NP_001333612.1, and NP_001333613.1. In some embodiments, human NaDC-1 has the amino acid sequence provided in NCBI Reference Sequence: NP_001139447.1. In some embodiments, human NaDC-1 has the following amino acid sequence:

(SEQ ID NO: 6)
MATCWQALWAYRSYLIVFFVPILLLPLPILVPSKEAYCAYAIILMALFWCT

EALPLAVTALFPLILFPMMGIVDASEIIQRPFPSSFESPGECQSVGMSVTA

SHNLGGTVGDSRVFPPLSHVSTCQVAVEYLKDSNLLFFGGLLVAIAVEHWN

LHKRIALRVLLIVGVRPAPLILGFMLVTAFLSMWISNTATSAMMVPIAHAV

LDQLHSSQASSNVEEGSNNPTFELQEPSPQKEVTKLDNGQALPVTSASSEG

RAHLSQKHLHLTQCMSLCVCYSASIGGIATLTGTAPNLVLQGQINSLFPQN

GNVVNFASWFSFAFPTMVILLLLAWLWLQILFLGFNFRKNFGIGEKMQEQQ

QAAYCVIQTEHRLLGPMTFAEKAISILFVILVLLWFTREPGFFLGWGNLAF

PNAKGESMVSDGTVAIFIGIIMFIIPSKFPGLTQDPENPGKLKAPLGLLDW

KTVNQKMPWNIVLLLGGGYALAKGSERSGLSEWLGNKLTPLQSVPAPAIAI

ILSLLVATFTECTSNVATTTIFLPILASMAQAICLHPLYVMLPCTLATSLA

FMLPVATPPNAIVFSFGDLKVLDMARAGFLLNIIGVLIIALAINSWGIPLF

SLHSFPSWAQSNTTAQCLPSLANTTTPSP.

In some embodiments, the at least one mutation increases binding to the H4c domain of NaDC-1. In some embodiments, the at least one mutation is a mutation that increases binding to lysine 107 and/or arginine 108 of SEQ ID NO: 5. In some embodiments, the at least one mutation is a mutation that increases binding to lysine 156 and/or arginine 157 of SEQ ID NO: 6.

In some embodiments, the inhibitory polypeptide comprises non-mutated IRBIT or a fragment, derivative, or analog thereof capable of binding NaDC-1. In some embodiments, the inhibitory polypeptide comprises a mutation that increases binding of the polypeptide to NaDC-1 as compared to a non-mutant IRBIT, increases stability of the polypeptide as compared to a non-mutant IRBIT, increases stability of a mutIRBIT-NaDC-1 complex as compared to a non-mutant IRBIT-NaDC-1 complex, or any combination thereof. In some embodiments, the inhibitory polypeptide comprises a mutation that decreases binding of the polypeptide to SUCNR1.

In some embodiments, a polypeptide, fragment, derivative or analog capable of binding NaDC-1, is capable of binding NaDC-1 in solution. In some embodiments, a polypeptide, fragment, derivative or analog capable of binding NaDC-1, is capable of binding NaDC-1 in an organism. In some embodiments, a polypeptide, fragment, derivative or analog capable of binding NaDC-1, is capable of binding NaDC-1 in a tissue. In some embodiments, a polypeptide, fragment, derivative or analog capable of binding NaDC-1, is capable of binding NaDC-1 in a body fluid. In some embodiments, a polypeptide, fragment, derivative or analog capable of binding NaDC-1, is capable of isolating NaDC-1 from a solution. In some embodiments, a polypeptide, fragment, derivative or analog capable of binding NaDC-1, is capable of chelating NaDC-1 from a solution. Methods of testing protein binding are well known in the art and include, but are not limited to pulldown assays, disassociation (Kd) assays such as an Alpha assay, and competition assays with ligand mimics.

In some embodiments, non-mutated SUCNR1 is mammalian SUCNR1. In some embodiments, SUCNR1 is human SUCNR1. In some embodiments, non-mutated SUCNR1 has the amino acid sequence provided in NCBI Reference Sequence: NP_149039.2. In some embodiments, SUCNR1 has the following amino acid sequence:

(SEQ ID NO: 7)
MLGIMAWNATCKNWLAAEAALEKYYLSIFYGIEFVVGVLGNTIVVYGYIFS

LKNWNSSNIYLFNLSVSDLAFLCTLPMLIRSYANGNWIYGDVLCISNRYVL

HANLYTSILFLTFISIDRYLIIKYPFREHLLQKKEFAILISLAIWVLVTLE

LLPILPLINPVITDNGTTCNDFASSGDPNYNLIYSMCLTLLGFLIPLFVMC

FFYYKIALFLKQRNRQVATALPLEKPLNVIMAVVIFSVLLFTPYHVMRNVR

IASRLGSWKQYQCTQVVINSFYIVTRPLAFLNSVINPVFYFLLGDHFRDML

MNQLRHNFKSLTSFSRWAHELLLSFREK.

In some embodiments, an amino acid sequence of non-mutated SUCNR1 is SEQ ID NO: 7.

In some embodiments, an analog to the polypeptide of the invention comprises an amino acid sequence with at least 60%, at least 65%, at least 70%, at least 75%, at least 80%, at least 85%, at least 90%, at least 95%, or at least 99% homology to the amino acid sequence presented in SEQ ID NO: 1.

In some embodiments, an analog to the polypeptide of the invention comprises an amino acid sequence with at least 60%, at least 65%, at least 70%, at least 75%, at least 80%, at least 85%, at least 90%, at least 95%, or at least 99% identity to the amino acid sequence presented in SEQ ID NO: 1.

In some embodiments, the polypeptide comprises a mutated extracellular domain (ED) of SUCNR1. In some embodiments, the polypeptide comprises a mutated trans-membrane domains (TMs) of SUCNR1. In some embodiments, the polypeptide comprises mutated ED and TMs of SUCNR1. In some embodiments, the polypeptide comprises mutated TM1, TM2, TM3, TM4, TM5, TM6, TM7 of SUCNR1 or a combination thereof. Each possibility represents a separate embodiment of the invention. In some embodiments, the polypeptide comprises mutated TM3, TM6 and TM7 of SUCNR1. In some embodiments, the polypeptide does not comprise the mutated intracellular domain of SUCNR1.

In some embodiments, the polypeptide comprises a mutated succinate binding pocket of SUCNR1. In some embodiments, the polypeptide comprises arginine 99 (R99), arginine 281 (R281), arginine 252 (R252) and histidine 103 (H103) of SEQ ID NO: 7. In some embodiments, at least one of these amino acids is mutated. In some embodiments, the polypeptide comprises arginine 99 (R99), arginine 281 (R281), arginine 252 (R252) or histidine 103 (H103) of SEQ ID NO: 7, or a combination thereof. In some embodiments, at least one of these amino acids is mutated.

In some embodiments, a polypeptide, fragment, derivative or analog capable of binding succinate, is capable of binding succinate in solution. In some embodiments, a polypeptide, fragment, derivative or analog capable of binding succinate, is capable of binding succinate in an organism. In some embodiments, a polypeptide, fragment, derivative or analog capable of binding succinate, is capable of binding succinate in a tissue. In some embodiments, a polypeptide, fragment, derivative or analog capable of binding succinate, is capable of binding succinate in a body fluid. In some embodiments, a polypeptide, fragment, derivative or analog capable of binding succinate, is capable of isolating succinate from a solution. In some embodiments, a polypeptide, fragment, derivative or analog capable of binding succinate, is capable of chelating succinate from a solution. Methods of testing protein binding are well known in the art and include, but are not limited to pulldown assays, disassociation (Kd) assays such as an Alpha assay, and competition assays with ligand mimics.

The term "fragment" as used herein, refers to a portion of the polypeptide, but a portion that still is capable of binding succinate or still comprises the succinate binding pocket. Such a fragment will still be recognizable as being from the polypeptide of the invention, and as such will be at least 10 amino acids in length. As such, any fragment of the isolated polypeptide of the invention will still comprise at least 10, at least 20, at least 30, at least 40, at least 50, at least 80, or at least 100 amino acids surrounding position 232. Each possibility represents a separate embodiment of the present invention.

In some embodiments, the solution is a buffer. In some embodiments, the solution is a storage buffer. In some embodiments, the solution is a pharmaceutically acceptable buffer, such as for administration to a subject. In some embodiments, the solution is a bodily fluid. In some embodiments, the bodily fluid is selected from at least one of: blood, serum, gastric fluid, intestinal fluid, saliva, bile and stool.

In some embodiments, the polypeptides of the invention are for use in decreasing NaDC-1 mediated transport of succinate. In some embodiments the polypeptides of the invention are for use in decreasing NaDC-1's transport of succinate. In some embodiments the polypeptides of the invention are for use in decreasing NaDC-1 mediated influx and/or efflux of succinate. In some embodiments the polypeptides of the invention are for use in decreasing NaDC-1 mediated influx but not efflux of succinate. In some embodiments the polypeptides of the invention are for use in decreasing NaDC-1 mediated transport of succinate into apical and/or basolateral membranes. In some embodiments the polypeptides of the invention are for use in decreasing NaDC-1 mediated transport of succinate into epithelial cells. In some embodiments the polypeptides of the invention are for use in decreasing NaDC-1 mediated trans-epithelial succinate transport. In some embodiments, the transport is succinate and citrate transport. In some embodiments the polypeptides of the invention are for use in decreasing NaDC-1 mediated succinate and/or citrate absorption.

In some embodiments the polypeptides of the invention are for use in decreasing serum succinate. In some embodiments, the polypeptides of the invention are for use in increasing urinary succinate. In some embodiments, the polypeptides of the invention are for use in treating a succinate-related disorder or condition. In some embodiments the polypeptides of the invention are for use in decreasing a level of succinate in a subject in need thereof. In some embodiments, the level of succinate in a subject is any one of serum succinate levels, renal succinate levels and intestinal succinate levels. In some embodiments, the level of succinate in a subject is any one of serum succinate levels, cardiac succinate levels, renal succinate levels and intestinal succinate levels. In some embodiments, the levels are succinate and/or citrate levels.

Mutations

Mutagenesis is well known to persons of skill in the art. Targeted mutation of proteins can be carried out by mutating the nucleic acid sequence which codes for the protein. By another aspect, there is provided a nucleic acid molecule which codes for a polypeptide of the invention.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The terms "nucleic acid molecule" include but not limited to single-stranded RNA (ssRNA), double-stranded RNA (dsRNA), single-stranded DNA (ssDNA), double-stranded DNA (dsDNA), small RNA such as miRNA, siRNA and other short interfering nucleic acids, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, nucleic acids of infectios origin, amplification products, modified nucleic acids, plasmidical or organellar nucleic acids and artificial nucleic acids such as oligonucleotides.

"Coding sequence" refers to a nucleic acid sequence that when translated results in an expressed protein. In some embodiments, the coding sequence is to be used as a basis for making codon alterations. In some embodiments, the coding sequence is used as a basis for making protein alterations. In some embodiments, the coding sequence is used as a basis for making mutations. In some embodiments, the coding sequence comprises a mammalian gene. In some embodiments, the coding sequence comprises a mouse gene. In some embodiments, the coding sequence comprises a human gene.

In some embodiments, mouse Slc26a6 has the nucleic acid sequence provided in NCBI Reference Sequence: NM_134420.4. In some embodiments, human Slc26a6 has the nucleic acid sequence provided in any one of NCBI Reference Sequences: AF288410.1, NM_022911.2, NM_134263.2, NM_134426.2, NM_001040454.1, NM_001281732.1, and NM_001281733.1. In some embodiments, human Slc26a6 has the nucleic acid sequence provided in any one of NCBI Reference Sequences: AF288410.1, and NM_022911.2. In some embodiments, human Slc26a6 has the nucleic acid sequence provided in NCBI Reference Sequence: NM_022911.2.

In some embodiments, mouse IRBIT has the nucleic acid sequence provided in any one of NCBI Reference Sequences: NM_145542.4, NM_1001357110.1, NM_001357111.1, NM_001357112.1, and NM_001357113.1. In some embodiments, mouse IRBIT has the nucleic acid sequence provided in NCBI Reference Sequence: NM_145542.4. In some embodiments, human IRBIT has the nucleic acid sequence provided in any one of NCBI Reference Sequences: NM_006621.5, NM_001242673.1, NM_001242674.1, NM_001242675.1, and NM_001242676.1. In some embodiments, human IRBIT has the nucleic acid sequence provided in NCBI Reference Sequence: NM_006621.5.

In some embodiments, a nucleic acid molecule has at least 60%, 70%, 80%, 90%, 95%, 97% or 99% identity to any one of mouse Slc26a6, mouse IRBIT, human Slc26a6 and human IRBIT. Each possibility represents a separate embodiment of the invention.

In some embodiments, the coding sequence of non-mutated SUNCR1 comprises the following sequence:

(SEQ ID NO: 8)
atgctggggatcatggcatggaatgcaacttgcaaaaactggctggcagca gaggctgccctggaaaagtactacctttccatttttatgggattgagttc gttgtgggagtccttggaaataccattgttgtttacggctacatcttctct ctgaagaactggaacagcagtaatatttatctctttaacctctctgtctct gacttagcttttctgtgcaccctccccatgctgataaggagttatgccaat ggaaactggatatatggagacgtgctctgcataagcaaccgatatgtgctt catgccaacctctataccagcattctctttctcacttttatcagcatagat cgatacttgataattaagtatcctttccgagaacaccttctgcaaaagaaa gagtttgctattttaatctccttggccatttgggttttagtaaccttagag attactacccatacttcccctataatcctgttataactgacaatggcacc acctgtaatgattttgcaagttctggagaccccaactacaacctcatttac agcatgtgtctaacactgttggggttccttattcctcttttgtgatgtgt ttcttttattacaagattgctctcttcctaaagcagaggaataggcaggtt gctactgctctgccccttgaaaagcctctcaacttggtcatcatggcagtg gtaatcttctctgtgcttttacaccctatcacgtcatgcggaatgtgagg atcgcttcacgcctggggagttggaagcagtatcagtgcactcaggtcgtc atcaactccttttacattgtgacacggcctttggcctttctgaacagtgtc atcaaccctgtcttctatttttttgggagatcacttcagggacatgctg atgaatcaactgagacacaacttcaaatcccttacatcctttagcagatgg gctcatgaactcctactttcattcagagaaaagtga.

In some embodiments, the coding sequence comprises the coding sequence provided in NCBI Reference Sequence: NM_033050.5.

In some embodiments, a nucleic acid molecule which codes for a non-mutated SUCNR1 comprises SEQ ID NO: 8. In some embodiments, a nucleic acid molecule which codes for a non-mutated polypeptide comprises a fragment, derivative or analog of SEQ ID NO:8.

In some embodiments, a nucleic acid molecule has at least 60% identity to SEQ ID NO: 8. In some embodiments, a nucleic acid molecule has at least 70% identity to SEQ ID NO: 8. In some embodiments, a nucleic acid molecule has at least 80% identity to SEQ ID NO: 8. In some embodiments, a nucleic acid molecule has at least 85% identity to SEQ ID NO: 8. In some embodiments, a nucleic acid molecule has at least 90% identity to SEQ ID NO: 8. In some embodiments, a nucleic acid molecule has at least 95% identity to SEQ ID NO: 8.

Site-directed nucleic acid mutagenesis is well known in the art, and can be performed, for example, with commercially available kits such as the Q5 kit from New England Biolabs, the QuikChange kits from Agilent Technologies, and the Phusion kit from Thermo Fisher Scientific to name but a few. In some embodiments, mutation of 1, 2 or 3 nucleotides of a codon will be sufficient to mutate an amino acid as required by the invention. Each possibility represents a separate embodiment of the invention. In some embodiments, the mutation is a deletion of at least one amino acid.

As used herein, "increases binding efficacy", and "increases binding" are used interchangeably and refer to a specific binding to a target (succinate) that is greater than the binding of a non-mutated control. In some embodiments, increased binding efficacy comprises a decreased dissociation constant (Kd) of the protein and succinate. In some embodiments, increased binding efficacy comprises decreased EC50 of the protein. In some embodiments, increased binding is an increase of at least 10, 20, 30, 40, 50, 60, 70, 80, 90, 100, 200, 300, 400, 500, 600, 700, 800, 900, or 1000% of binding as compared to binding of a non-mutated polypeptide. Each possibility represents a separate embodiment of the invention. Protein-protein binding is well known to a person of skill in the art. Protein-protein binding can be assayed in any way known to one skilled in the art, including but not limited to: x-ray crystallography, immunoprecipitation, immunoblotting, competition assays, and kinetic exclusion assays.

In some embodiments, the mutation that increases binding is a mutation within a NaDC-1 binding pocket. In some embodiments, the mutation that increases binding is a mutation within a NaDC-1 binding surface. In some embodiments, the mutation that increases binding is a mutation outside of the NaDC-1 binding pocket or surface. In some embodiments, the mutation that decreases binding is a mutation within a SUCNR1 binding pocket. In some embodiments, the mutation that decreases binding is a mutation within a SUCNR1 binding surface. In some embodiments, the mutation that decreases binding is a mutation outside of the SUCNR1 binding pocket or surface.

In some embodiments, the mutation that increases binding is mutation of a charged amino acid. In some embodiments, the mutation that increases binding is mutation of a positively charged amino acid. In some embodiments, the mutation that increases binding is mutation of a non-charged amino acid to a charged amino acid. In some embodiments, the mutation that increases binding is mutation of a negatively charged amino acid to a non-charged amino acid. In some embodiments, the mutation that increases binding is mutation of a non-charged or negatively charged amino acid to a positively charged amino acid. In some embodiments, the mutation that increases binding is mutation of a positively charged amino acid to a more strongly positively charged amino acid. The charges of amino acids are well known in the art, and can be measured, among other ways, by determining the isoelectric point of the amino acid.

In some embodiments, the mutation that increases binding is a mutation within the succinate binding pocket. In some embodiments, the mutation that increases binding is a mutation outside of the succinate binding pocket. In some embodiments, the mutation that increases binding is mutation of a charged amino acid. In some embodiments, the mutation that increases binding is mutation of a positively charged amino acid. In some embodiments, the mutation that increases binding is mutation of a non-charged amino acid to a charged amino acid. In some embodiments, the mutation that increases binding is mutation of a negatively charged amino acid to a non-charged amino acid. In some embodiments, the mutation that increases binding is mutation of a non-charged or negatively charged amino acid to a positively charged amino acid. In some embodiments, the mutation that increases binding is mutation of a positively charged amino acid to a more strongly positively charged amino acid. The charges of amino acids are well known in the art, and can be measured, among other ways, by determining the isoelectric point of the amino acid.

In some embodiments, the at least one mutation is a mutation that increases binding to succinate. In some embodiments, the mutation is mutation of at least one of the following amino acids of SEQ ID NO: 7: Arginine 99, Histidine 103, Arginine 252, and Arginine 281 (R99, H103, R252 and R281). In some embodiments, the mutation that increases binding is mutation of a at least one of R99, H103, R252 and R281 of SEQ ID NO: 7 to a more positively charged amino acid. For example, such a mutation could be mutating R99 to a histidine (R99H).

As used herein, "increases stability" refers to survival of a protein or complex in an intact or functional state that is longer than survival of a non-mutated control. In some embodiments, increased stability comprises decreased degradation. In some embodiments, increased stability comprises decreased proteolytic degradation. In some embodiments, increased stability comprises increased half-life of the protein. In some embodiments, increased stability comprises decreased EC50 of the protein. In some embodiments, increased stability is an increase of at least 10, 20, 30, 40, 50, 60, 70, 80, 90, 100, 200, 300, 400, 500, 600, 700, 800, 900, or 1000% in stability as compared to a non-mutated protein or complex containing a non-mutated protein. Each possibility represents a separate embodiment of the invention. Measuring stability of a protein will be well known to a person skilled in the art and can be achieved through any known mean or assay in the art, including, but not limited to a thermal shift assay, a cycloheximide assay, or a half-life assay.

In some embodiments, the at least one mutation is a mutation that increases stability of the polypeptide. In some embodiments, the at least one mutation is a mutation that increases stability of a NaDC-1 containing complex. In some embodiments, the mutation that increases stability of the polypeptide is a mutation within the extracellular domain. In some embodiments, the mutation that increases stability of the polypeptide is a mutation within a TM domain.

In some embodiments, increased stability is increased stability in a solution. In some embodiments, the solution is a buffer. In some embodiments, the solution is a storage buffer. In some embodiments, the solution is a pharmaceutically acceptable buffer, such as a pharmaceutical composition. In some embodiments, the solution is a bodily fluid. In some embodiments, the bodily fluid is selected from at least one of: blood, serum, gastric fluid, intestinal fluid, saliva, bile and stool.

In some embodiments, the at least one mutation is a mutation that increases stability of the polypeptide. In some embodiments, the at least one mutation is a mutation that increases stability of a receptor-succinate complex. In some embodiments, the mutation that increases stability of the polypeptide is a mutation within the extracellular domain. In some embodiments, the mutation that increases stability of the polypeptide is a mutation within a TM domain. In some embodiments, the mutation is a mutation of at least one of the following amino acids: Leucine 191, Threonine 192, Glycine 195, Isoleucine 110, Phenylalanine 241, Methionine 203, Valine 238, Tyrosine 207, Arginine 120, Arginine 281, Phenylalanine 285, Asparagine 287, and Tyrosine 295 (L191, T192, G195, I110, F241, M203, V238, T207, R120, R281, F285, N287 and T295) of SEQ ID NO: 7.

Pharmaceutical Compositions

By another aspect; there is provided a pharmaceutical composition comprising any of the isolated polypeptides of the invention and a pharmaceutically acceptable carrier, excipient, or adjuvant.

As used herein, the term "carrier," "adjuvant" or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

Methods of Use

By another aspect, there is provided a method of treating or preventing a succinate-associated disease or condition in a subject in need thereof, the method comprising administering to the subject any of the pharmaceutical compositions of the invention.

By another aspect, there is provided a method of treating or preventing a succinate-associated disease or condition in a subject in need thereof, the method comprising decreasing serum succinate levels in the subject, thereby treating or preventing a succinate-associated disease or condition.

In some embodiments, the succinate-associated disease or condition is selected from IBD, kidney stones and hypertension. In some embodiments, the succinate-associated disease or condition is IBD. In some embodiments, the succinate-associated disease or condition is kidney stones. In some embodiments, the succinate-associated disease or condition is hypertension. In some embodiments, the succinate-associated disease or condition is selected from IBD, urolithiasis, rheumatoid arthritis, cardiac hypertrophy, inflammation, kidney stones and hypertension. In some embodiments, IBD is anyone of colitis, ulcerative colitis, Crohn's disease and Bechet's disease. In some embodiments, IBD is colitis. In some embodiments, IBD is Crohn's disease. In some embodiments, IBD is Bechet's disease. In some embodiments, the subject suffering from IBD further suffers from kidney stones and/or hypertension. In some embodiments, IBD further comprises at least one of: kidney stones, hypertension, arthritis, non-alcoholic fatty liver diseases (NAFLD), non-alcoholic steatohepatitis (NASH) and primary sclerosing cholangitis and cholestasis. In some embodiments, the hypertension is not dependent on sodium intake. In some embodiments, the hypertension is dependent on sodium intake. In some embodiments, the hypertension is not dependent on exercise. In some embodiments, the hypertension is dependent on exercise.

In some embodiments, decreasing serum succinate levels comprises administering SUCNR1 or a fragment, derivative, analog or mutant thereof, that binds succinate. In some embodiments, the SUCNR1 or a fragment, derivative, analog or mutant thereof sweeps succinate from the blood. In some embodiments, the SUCNR1 or a fragment, derivative, analog or mutant thereof binds free succinate. In some embodiments, the SUCNR1 or a fragment, derivative, analog or mutant thereof blocks binding of serum succinate to a receptor on a cell. In some embodiments, the administered SUCNR1 is recombinant SUCNR1.

In some embodiments, decreasing serum succinate levels comprises decreasing NaDC-1 transport of succinate. In some embodiments, decreasing serum succinate levels comprises decreasing NaDC-1 transport of succinate out of urine. In some embodiments, decreasing NaDC-1 transport of succinate comprises increasing binding of NaDC-1 to solute carrier family 26 member 6 (Slc26a6), IP3 receptor-binding protein released with IP3 (IRBIT) or both. In some embodiments, decreasing NaDC-1 transport of succinate comprises increasing binding of NaDC-1 to slc26a6. In some embodiments, decreasing NaDC-1 transport of succinate comprises increasing binding of NaDC-1 to IRBIT. In some embodiments, decreasing NaDC-1 transport of succinate comprises increasing binding of NaDC-1 to Slc26a6 and/or IRBIT.

In some embodiments, increasing binding to Slc26a6 comprises increasing electrostatic interaction between a STAS domain of Slc26a6 and a H4c domain of NaDC-1. In some embodiments, increasing electrostatic interaction comprises increasing negative charge in the Slc26a6-STAS domain. In some embodiments, embodiments the electrostatic interactions of glutamic acid 613 and/or aspartic acid 637 of Slc26a6 is increased. In some embodiments, the electrostatic interactions of lysine 107 and/or arginine 108 of SEQ ID NO: 5 are increased. In some embodiments, the electrostatic interactions of lysine 156 and/or arginine 157 of SEQ ID NO: 6 are increased.

In some embodiments, increasing binding of NaDC-1 to Slc26a6, IRBIT or both comprises administering to the subject a polypeptide of the invention. some embodiments, increasing binding of NaDC-1 to Slc26a6, IRBIT or both comprises administering to the subject a polypeptide comprising an amino acid sequence of: a Slc26a6 STAS domain, or a fragment, derivative or analog thereof, capable of binding NaDC-1, and comprising glutamic acid 613 or aspartic acid 637; or IRBIT or a fragment, derivative or analog thereof capable of binding NaDC-1. In some embodiments, increasing binding of NaDC-1 to Slc26a6 comprises administering to the subject a polypeptide comprising an amino acid sequence of a Slc26a6 STAS domain, or a fragment, derivative or analog thereof, capable of binding NaDC-1, and comprising glutamic acid 613 or aspartic acid 637. In some embodiments, increasing binding of NaDC-1 to IRBIT comprises administering to the subject a polypeptide comprising an amino acid sequence of IRBIT or a fragment, derivative or analog thereof capable of binding NaDC-1.

In some embodiments, the polypeptide comprises an amino acid sequence of a mutant Slc26a6 (mutSlc26a6) or mutant IRBIT (mutIRBIT), said mutSlc26a6 or mutIRBIT comprising at least one mutation which
 a. increases binding of said polypeptide to NaDC-1 as compared to a non-mutant Slc26a6 or IRBIT,
 b. increases stability of said polypeptide as compared to a non-mutant Slc26a6 or IRBIT,
 c. increases stability of a mutSlc26a6-NaDC-1 complex or a mutIRBIT-NaDC-1 complex as compared to a non-mutant Slc26a6-NaDC-1 complex or a non-mutant IRBIT-NaDC-1 complex, or
 d. any combination thereof.

In some embodiments, NaDC-1 comprises the amino acid sequence of SEQ ID NO:5 or 6 and the at least one mutation increases binding of lysine 107, arginine 108, or both of SEQ ID NO: 5 or lysine 156, arginine 157, or both of SEQ ID NO: 6.

In some embodiments, the pharmaceutical compositions of the invention are for use in decreasing NaDC-1's transport of succinate. In some embodiments, the pharmaceutical compositions of the invention are for use in decreasing NaDC-1 mediated transport of succinate. In some embodiments the pharmaceutical compositions of the invention are for use in decreasing NaDC-1 mediated influx and/or efflux of succinate. In some embodiments the pharmaceutical compositions of the invention are for use in decreasing NaDC-1 mediated influx but not efflux of succinate. In some embodiments the pharmaceutical compositions of the invention are for use in decreasing NaDC-1 mediated transport of succinate into apical and/or basolateral membranes. In some embodiments the pharmaceutical compositions of the invention are for use in decreasing NaDC-1 mediated transport of succinate into epithelial cells. In some embodiments the pharmaceutical compositions of the invention are for use in decreasing NaDC-1 mediated trans-epithelial succinate transport. In some embodiments, the transport is succinate and citrate transport. In some embodiments the pharmaceutical compositions of the invention are for use in decreasing NaDC-1 mediated succinate and/or citrate absorption.

In some embodiments, the pharmaceutical compositions of the invention are for use in decreasing a level of succinate in a subject in need thereof. In some embodiments, the level of succinate in a subject is any one of serum succinate levels, renal succinate levels and intestinal succinate levels. In some embodiments, the level of succinate in a subject is any one of serum succinate levels, cardiac succinate levels, renal succinate levels and intestinal succinate levels. In some embodiments, the levels are succinate and/or citrate levels.

In some embodiments, the pharmaceutical compositions of the invention are for use in treating or preventing a succinate-associated disease or condition. As used herein, a "succinate-associated disease or condition" refers to any disease or condition in which succinate contributes to the pathology. In some embodiments, a succinate-associated disease or condition comprises elevated succinate levels. In some embodiments, the elevated succinate levels are at least 5%, 10%, 20%, 25%, 30%, 40%, 50%, 60%, 70%, 80%, 90%, or 100% higher than succinate levels in a healthy individual. Each possibility represents a separate embodiment of the invention. In some embodiments, the elevated levels are elevated levels in blood. In some embodiments, the elevated levels are elevated circulating succinate. In some embodiments, a succinate-associated disease or condition comprises hyposuccinaturia. As used herein "hyposuccinaturia" refers to decreased levels of succinate in the urine of a subject. In some embodiments, the decreased succinate levels in urine are at least 5%, 10%, 20%, 25%, 30%, 40%, 50%, 60%, 70%, 80%, 90%, or 95% lower than succinate levels in the urine of a healthy individual. Each possibility represents a separate embodiment of the invention. In some embodiments, a succinate-associated disease or condition is selected from the group consisting of: inflammatory bowel disease, urolithiasis, rheumatoid arthritis, cardiac hypertrophy, inflammation and hypertension. In some embodiments, a succinate-associated disease or condition is selected from the group consisting of: inflammatory bowel disease, urolithiasis, and hypertension.

In some embodiments, the pharmaceutical compositions of the invention are for use in treating an inflammatory bowel disease, urolithiasis and hypertension. In some embodiments, the pharmaceutical compositions of the invention are for use in treating an inflammatory bowel disease. In some embodiments, the pharmaceutical compositions of the invention are for use in treating urolithiasis. In some embodiments, the pharmaceutical compositions of the invention are for use in treating hypertension. In some embodiments, the inflammatory bowel disease is selected from any one of: colitis, ulcerative colitis, Crohn's disease and Bechet's disease. In some embodiments, the inflammatory bowel disease further comprises at least one of: kidney stones, hypertension, arthritis, non-alcoholic fatty liver diseases (NAFLD), non-alcoholic steatohepatitis (NASH) and primary sclerosing cholangitis and cholestasis. In some embodiments, the inflammatory bowel disease comprises the symptom of kidney stones. In some embodiments, the hypertension is not affected and/or dependent on salt intake.

In some embodiments, the method of treating or preventing a succinate associated disease or condition in a subject in need thereof, comprises administering to said subject any of the pharmaceutical compositions of the invention. In some embodiments, the method of treating or preventing a succinate associated disease or condition in a subject in need thereof, comprises administering to said subject any of the polypeptides of the invention.

In some embodiments, the polypeptide is at least one of the polypeptides of the invention. In some embodiments, the polypeptide is a mix of polypeptides of the invention.

In some embodiments, treating comprises a reduction in symptoms. A person skilled in the art will be familiar with symptoms of the diseases and conditions described herein. Treating does not imply a complete cure necessarily but may refer to any improvement in the condition or the patient's wellbeing. In some embodiments, a reduction is symptoms is a reduction of at least one symptom. In some embodiments, the disease is IBD and the symptom is selected from: abdominal pain, diarrhea, fever, fatigue, cramping, bloody stool, reduced appetite, weight loss, kidney stones, inflammation of the bowel and a combination thereof.

In some embodiments, treating a succinate associated disease or condition comprises reducing the levels of free succinate in a patient. In some embodiments, treating a succinate associated disease or condition comprises reducing the levels of free succinate in a patient's bowel, intestines blood, kidneys and/or heart. Each possibility represents a separate embodiment of the invention. In some embodiments, treating a succinate associated disease or condition comprises reducing the levels of free succinate in a patient's blood. In some embodiments, treating a succinate associated disease or condition comprises reducing the levels of free succinate in a patient's stool. In some embodiments, treating inflammatory bowel disease comprises reducing the occurrence of kidney stones.

In some embodiments, treating inflammatory bowel disease comprises reducing the levels of free succinate in a patient. In some embodiments, treating inflammatory bowel disease comprises reducing the levels of free succinate in a patient's bowel. In some embodiments, treating inflammatory bowel disease comprises reducing the levels of free succinate in a patient's intestines. In some embodiments, treating inflammatory bowel disease comprises reducing the levels of free succinate in a patient's stool. In some embodiments, treating inflammatory bowel disease comprises reducing the levels of free succinate in a patient's blood. In some embodiments, treating inflammatory bowel disease comprises reducing the occurrence of kidney stones.

In some embodiments, the methods of the invention further comprise administering to the subject potassium (K) positive-citrate. In some embodiments, K+ citrate treats the symptom of kidney stones. In some embodiments, the pharmaceutical compositions of the invention and K+ citrate treat the symptom of kidney stones.

In some embodiments, the methods of the invention further comprise administering SUCNR1 or a fragment, derivative, analog or mutant thereof capable of binding succinate.

By another aspect, there is provided a method of increasing succinate reabsorption in a subject in need thereof, the method comprising inhibiting interaction between NaDC-1 and IRBIT in the subject thereby increasing succinate reabsorption in the subject.

By another aspect, there is provided a method of increasing succinate reabsorption in a subject in need thereof, the method comprising inhibiting electrostatic interaction between the STAS domain of Slc26a6 and the H4c domain of NaDC-1, thereby increasing succinate reabsorption in a subject in need thereof.

In some embodiments, the methods of the invention are for use in increasing NaDC-1's transport of succinate. In some embodiments, the methods of the invention are for use in increasing NaDC-1 mediated transport of succinate. In some embodiments the methods of the invention are for use in increasing NaDC-1 mediated influx and/or efflux of succinate. In some embodiments the methods of the invention are for use in increasing NaDC-1 mediated influx but not efflux of succinate. In some embodiments the methods of the invention are for use in increasing NaDC-1 mediated transport of succinate into apical and/or basolateral membranes. In some embodiments the methods of the invention are for use in increasing NaDC-1 mediated transport of succinate into epithelial cells. In some embodiments the methods of the invention are for use in increasing NaDC-1 mediated trans-epithelial succinate transport. In some embodiments, the transport is succinate and citrate transport. In some embodiments the methods of the invention are for use in increasing NaDC-1 mediated succinate and/or citrate absorption. In some embodiments, the methods of the invention are for use in increasing blood pressure. In some embodiments, the methods of the invention are for treating hypotension.

In some embodiments, the methods of the invention are for use in increasing a level of succinate in a subject in need thereof. In some embodiments, the level of succinate in a subject is any one of serum succinate levels, renal succinate levels and intestinal succinate levels. In some embodiments, the level of succinate in a subject is any one of serum succinate levels, cardiac succinate levels, renal succinate levels and intestinal succinate levels. In some embodiments, the levels are succinate and/or citrate levels.

In some embodiments, the methods of the invention are for use in treating or preventing hypotension.

In some embodiments, inhibiting electrostatic interaction comprises blocking interaction of E613 or D637 of Slc26a6 with the H4c domain of NaDC-1. In some embodiments, inhibiting electrostatic interaction comprises blocking interaction of K107, R108, K156 and/or R157 of NaDC-1 with the STAS domain of Slc26a6. In some embodiments, blocking interaction comprises mutation of at least one of amino acids E613 and D637 of Slc26a6, and K107, R108, K156 and R157 of NaDC-1. In some embodiments, the mutation is to a non-charged amino acid. In some embodiments, the mutation is to an amino acid with an opposite charge. In some embodiments, the mutation is to alanine.

In some embodiments, inhibiting interaction comprises contacting Slc26a6, IRBIT, and/or NaDC-1 with a blocking antibody or antibody fragment. Blocking antibodies are well known in the art, and assaying blocking of an interaction can be performed as described above for assaying protein-protein interactions.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass.

As used herein, the terms "administering," "administration," and like terms refer to any method which, in sound medical practice, delivers a composition containing an active agent to a subject in such a manner as to provide a therapeutic effect. One aspect of the present subject matter provides for oral administration of a therapeutically effective amount of a composition of the present subject matter to a patient in need thereof. Other suitable routes of administration can include parenteral, subcutaneous, intravenous, intramuscular, anal or intraperitoneal.

The dosage administered will be dependent upon the age, health, and weight of the recipient, kind of concurrent treatment, if any, frequency of treatment, and the nature of the effect desired.

Diagnostics

By another aspect, there is provided a method of diagnosing increased levels of serum succinate in a subject, the method comprising obtaining a urine sample from the subject and measuring succinate levels in the urine sample, wherein a decrease in urine succinate levels as compared to a healthy control indicates an increase in succinate levels in the subject. In some embodiments, the method is for diagnosing an increased risk of a succinate-associated disease or condition in the subject. In some embodiments, the method is for diagnosing an increased risk of developing a succinate-associated disease or condition in the subject.

In some embodiments, the method is for diagnosing an increased risk of an inflammatory bowel disease in the subject. In some embodiments, the method is for diagnosing an increased risk of developing an inflammatory bowel disease in the subject. In some embodiments, the method is for diagnosing an increased risk of IBD, hypertension and/or kidney stones.

In some embodiments, the method comprises contacting the urine with a succinate detecting molecule. In some embodiments, the succinate detecting molecule is a labeled anti-succinate antibody. In some embodiments, the succinate detecting molecule is a labeled recombinant SUCNR1 protein or succinate binding fragment thereof. In some embodiments, the detecting molecule is attached to a support. In some embodiments, the support is solid. In some embodiments, the support is artificial.

In some embodiments, the diagnostic methods of the invention are performed ex vivo. In some embodiments, the diagnostic methods of the invention are performed in vitro. In some embodiments, the detection does not comprise protein purification from the urine. A skilled artisan will appreciate that a urine test is much less invasive and easier to administer than is a blood test.

In some embodiments, the diagnostic methods of the invention further comprise treating a subject found to have decreased urine succinate levels, by one of the treatment methods of the invention.

Measuring urinary succinate can be performed by any method known in the art. Measuring metabolites in urine is a well-known clinical test and any such tests can be applied to succinate. Succinate measurements in urine can also be performed using commercially available kits such as the enzymatic succinate test kit (Sigma-Aldrich) as a non-limiting example. In some embodiments, the succinate measurement is made as part of a larger urine panel, or as part of the classical urine panel. In some embodiments, the succinate measurement is made as part of a metabolic panel.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Animal Care and Metabolic Experiments:

All the work on mice and all *Xenopus laevis* procedures were approved by the Institutional Animal Care and Use Committee of the Ben Gurion University of the Negev and of the National Institute of Craniofacial and Dental Research, National Institutes of Health (NIH). Wildtype and slc26a6$^{-/-}$ mice were individually housed in Tecniplast metabolic cages (Tecniplast, Italy). All mice were on rodent diet and tap water ad libitum during the experiments. After acclimatization to metabolic cages, 24 h urine samples were collected over the course of three consecutive days. The collected samples were analyzed for urine succinate by using an enzymatic succinate test kit (Sigma-Aldrich) and for creatinine.

Succinate Uptake Measurements:

HEK293T cells were transfected with the relevant plasmids using the calcium-phosphate method. On the day of the experiment, the cells were washed with an incubation solution (in mM): 5 KCl, 10 HEPES, 10 glucose, 140 NaCl, 3 Na$^+$-Succinate, pH 7.4. Subsequently, incubation solution supplemented with 1 mM Na$^+$-succinate and 1 µCi $^{14}$C-succinic acid (ViTrax Inc.) per 1.6 µmol cold succinate was added to the cells. The cells were then washed twice in incubation solution and 0.3 ml NaOH (1M) was immediately added to lyse the cells. The lysates were then transferred to scintillation vials containing 0.3 ml of HCl (1M). Alternatively, *Xenopus* oocytes were incubated with 3 mM Na$^+$-succinate and 1 µCi $^{14}$C-succinic acid per 1.2 µmol cold succinate (to monitor OAT-mediated uptake) or with 1 mM Na$^+$-succinate and 1 µCi $^{14}$C-succinic acid per 0.4 µmol cold succinate (to monitor Na-mediated uptake). Oocytes were then lysed using 200 µl of 2% SDS. Finally, radioactivity was determined by liquid scintillation counting using a Packard 1900CA TRI-CARB analyzer. The osmolarity of all solutions was adjusted to 300 mOsm with the major salt.

Plasmid Construction and cRNA Preparation:

The following vectors were used: human NaDC-1 clone (NCBI access. No. BC096277) in the pCMV6-AC-Myc-His vector; the human SLC26A6 clone (NCBI access. No. NM_022911) in the pCMV6-AC vector; the mouse slc26a6 (NCBI access. No. NM_134420) in the pCMV6-AC-mKate vector; IRBIT in pcDNA3.1(+); the mouse oat1 (slc22a6 NCBI access. No. NM_008766) and mouse oat3 (slc22a8 NCBI access. No. NM_001164635) clones in the pCMV6-Entry myc-DDK vector; mouse NaDC-3 (slc13a3 NCBI access. No. BC026803) clone in pCMV-SPORT6; and human SUCNR1 (NCBI access No. NM_033050) in pCMV6-XL5). All site-directed mutants were generated with QuikChange Lightning Site-Directed Mutagenesis Kit (Agilent, Santa Clara, Calif.). All constructs were verified by sequencing and immunoblot of the protein products. The genes cloned into vectors pCMV6-AC-mKate and pCMV-AC-myc-His were linearized using relevant restriction enzymes and transcribed in vitro with T7 mMessage mMachine ultra (Thermo-Fisher scientific, Waltham, Mass.) or SP6/T7 AmpliCap™ (CELLSCRIPT, Madison, Wis.).

Preparation and Injection of Oocytes:

Oocytes were obtained by a partial ovariectomy of female *Xenopus laevis* (Xenopus One, Dexter, Mich.). Briefly, the frogs were anesthetized, and follicle cells were removed in an OR-2 calcium-free medium. The defolliculated oocytes were washed with OR-2 calcium-free medium and healthy oocytes in stages V to VI were identified, collected under binoculars and maintained overnight at 18° C. in an ND96 solution. 32 nl of the different cRNA were injected into the oocytes using a Nanoliter 2010 injector (World Precision Instruments, Inc., Sarasota, Fla.). Similar volumes and concentrations (4 µg/µl) of cRNA or water were mixed to achieve similar amounts of injected cRNA per oocyte. The oocytes were incubated at 18° C. in an ND96 solution with pyruvate and antibiotics and they were tested 48-96 h after cRNA injection.

Voltage, Current abd [Cl–] in Measurement in Oocytes:

Voltage and current recordings were performed with a two-electrode voltage clamp. The current was recorded with a Warner Instrument Corporation amplifier model OC-725C (Hamden, Conn.) and digitized via an A/D converter (Digidata 1550A; Axon Instruments, Inc.). The electrode tips were filled with 0.5 µl of Cl$^-$-sensitive liquid ion exchanger 477913 (Corning) and then backfilled with a 3M KCl solution. During measurements, two channels were used for ion-sensitive measurement and another was used to record or control the membrane potential. The Cl$^-$ signals were extracted by subtracting the membrane potential signal from the ion-selective electrodes signal. Data were analyzed using the Clampex 10 system (Axon Instruments, Inc.). The following solutions were used as indicated in the figures: Standard HEPES-buffered ND96 oocyte regular medium containing (in mM): 96 NaCl, 2 KCl, 1.8 CaCl$_2$), 1 MgCl$_2$, and 5 HEPES, pH=7.5. Cl$^-$-free solutions for oocytes were prepared by replacing Cl$^-$ with gluconate and MgCl$_2$ with MgSO$_4$. Na$^+$-oxalate (in Ca2+-free solution) and Na$^+$-succinate were added to the solutions as indicated in the figures.

Western Blot and Co-Immunoprecipitation:

Cell lysates were prepared by incubating the cells in an ice-cold lysis buffer containing PBS, 10 mM $Na^+$-pyrophosphate, 50 mM NaF, 1 mM $Na^+$-orthovanadate, 1% Triton X-100, and a cocktail of protease inhibitors (Roche). Extracts were incubated overnight with the indicated antibodies and the complexes were collected with either protein A or G sepharose beads (Sigma-Aldrich) by incubation for 4 h at 4° C. Beads were collected by centrifugation, washed three times with a lysis buffer, and the proteins were recovered by heating (37° C. for 30 min) in the SDS sample buffer. The samples were subjected to SDS-PAGE and subsequently transferred to nitrocellulose membranes (GE Whatman, Pittsburgh, Pa.). Kidney lysates were prepared following excision of the two kidneys from each mouse. The capsules were removed by pinching and the corticomedullary region was cut out, washed in PBS (pH=7.4) and transferred into an ice-cold lysis buffer described above. The tissue was homogenized and centrifuged at 4° C., the supernatant was collected and sonicated. Total protein concentration was determined by the Lowry method and 60 μg of total protein were loaded from each sample, separated by SDS-PAGE and western blot analysis was performed. The nitrocellulose membranes were incubated overnight with either anti-SUCNR1 (Novusbio, Littleton, Colo.), anti-pNCC (Thr[53]) (Phosphosolutions, Aurora, Colo.), anti-IR-BIT (Santa cruz biotechnology) or anti-β actin antibodies.

3D Protein Model Prediction:

The putative structure of NaDC-1 was predicted using HHPred software with high homology to the crystal structure of a bacterial dicarboxylate/sodium symporter (PDB_ID: 4F35). Prediction parameters: E-value=7.7e-42, Score=374.69, Identities=31%, Similarity=0.510. The slc26a6 STAS domain structure was predicted based on the crystal structure of slc26a5-STAS (PDB_ID: 3LLO). The interaction between NaDC-1 and STAS-slc26a6 domain was predicted with the HADDOCK software. The results of NaDC-1 and the slc26a6 STAS interaction were provided by the software, as follows: score −106.3±5.4, cluster size 5, RMSD from overall low-energy structure 3.5±0, van der Waals energy −43.6±4, electrostatic energy −271.4±22.5. All final models were generated with PyMol software (Schrödinger Inc., New-York, N.Y.).

Plasma Renin Test:

Blood samples for plasma renin were obtained from the tail vein of slc26a6$^{-/-}$ male mice and their WT littermates' controls at 3-4 months of age. Total Renin was measured in duplicate using Mouse Renin ELISA test kit (Thermo-Fisher Scientific) according to the manufacturer's protocol.

Mass-Spectrometry:

To measure succinate levels in mice serum, 25 μl of serum were mixed with 100 μl of 50:30 (v/v) methanol:acetonitrile solution at −20° C. All metabolite extractions were stored at −80° C. overnight, followed by centrifugation, twice at 20,000 g for 20 min to obtain protein-free metabolite extracts. Chromatographic separation was achieved on a SeQuant ZIC-pHILIC column (2.1×150 mm, 5 μm bead size, Merck Millipore). Flow rate was set to 0.2 ml/min, column compartment was set to 30° C., and autosampler tray was maintained at 4° C. Mobile phase A consisted of 20 mM ammonium carbonate with 0.01% (v/v) ammonium hydroxide. Mobile Phase B was 100% acetonitrile. The mobile phase linear gradient (% B) was as follows: 0 min 80%, 15 min 20%, 15.1 min 80%, and 23 min 80%. A mobile phase was introduced to Thermo Q-Exactive mass spectrometer with an electrospray ionization source working in polarity switching mode. Metabolites were analyzed using full-scan method in the range 70-1,000 m/z and with a resolution of 70,000. Positions of metabolites in the chromatogram were identified by corresponding pure chemical standards. Data were analyzed with MAVEN (Clasquin et al, 2012).

Telemetric Blood Pressure Measurement:

The mice were prepared for surgery by general anesthesia using isoflurane 1-3%. While under general anesthesia, the carotid artery was exposed, and two silk suture ties were placed, 6-7 mm apart, under a non-branching segment of the carotid. The proximal tie was used to secure a catheter in the vessel, and the distal tie, near the bifurcation of the internal and external carotid arteries, was used to ligate the artery. The vessel was then punctured between the two ties to create an arteriotomy for placement of the catheter. The DSI PA-C10 transmitter catheter (DSI, St. Paul, Minn.) was placed in the vessel and advanced until the catheter tip was in the aortic arch. The catheter was then secured in the vessel using silk ties. Next, the transmitter was placed subcutaneously along the animal's flank between the forelimb and the hind limb. Using a blunt dissection, the skin was separated from the underlying muscle to create a subcutaneous pouch and a tunnel which began at the cervical incision and extended to the lateral chest. The transmitter was placed through the incision and moved through the tunnel to the subcutaneous pouch. Finally, Buprenex (0.05-0.1 mg/kg) was administered for pain relief and the mice remained in an oxygenated cage overnight. After 14 d of recovery, the mice were fed NIH 31 chow and housed in cages that were placed on top of the receivers to monitor 24 h blood pressure (measurements were taken at 5 min intervals). To test the effects of NaCl on blood pressure the mice were fed with high salt (4% NaCl) diet for two weeks, followed by a week of regular NIH 31 chow and another two weeks of a low-salt (0.49% NaCl) diet. For physical stress tests, the mice were trained to run on a treadmill (Model Eco-6M, Columbus Instruments, Columbus, Ohio) and then exposed, once a day, to moderate-intensity exercise (treadmill speed of 10 m/min) for 15 minutes, while their blood pressure was simultaneously recorded with the DSI telemetry system.

$Ca^{2+}$ Imaging:

The imaging system consisted of an Eclipse Ti inverted microscope (Nikon, Japan), a PE-4000 LED monochromator (CoolLEd, Andover, UK) and Hamamatsu flash 4.0LT camera (Hamamatsu Photonics, Japan). Fluorescent images were acquired and analyzed with NIS-Elements software (Nikon, Japan). $Ca^{2+}$ imaging was performed in HEK293T cells attached onto coverslips and perfused with a regular solution (containing (in mM): 140 NaCl, 5 KCl, 1 $MgCl_2$, 10 HEPES, 1 $CaCl_2$), 10 glucose, pH adjusted to 7.4). A $Ca^{2+}$-free solution was prepared without $CaCl_2$), and $Na^+$-succinate was added to the solutions as indicated. In HEK293T cells, $[Ca^{2+}]_i$ was monitored by transiently expressing the $Ca^{2+}$ sensor protein GCaMP (a kind gift from Dr. Loren Looger's lab) in the presence or absence of SUCNR1.

Statistics:

Significance was analyzed by using student's T-test. All results are presented as mean±S.E.M. *P<0.05, P<0.005, *P<0.0005. N is indicated in the figures.

Example 1: Metabolite Targets that Modulate Inflammation

Figure 1C:
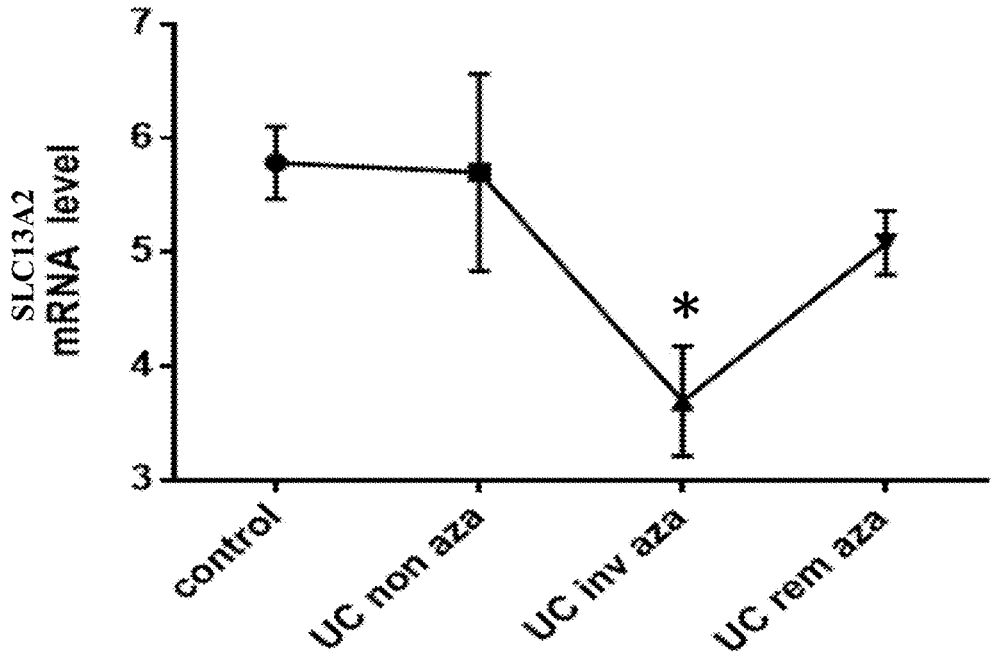
Figure 1D:
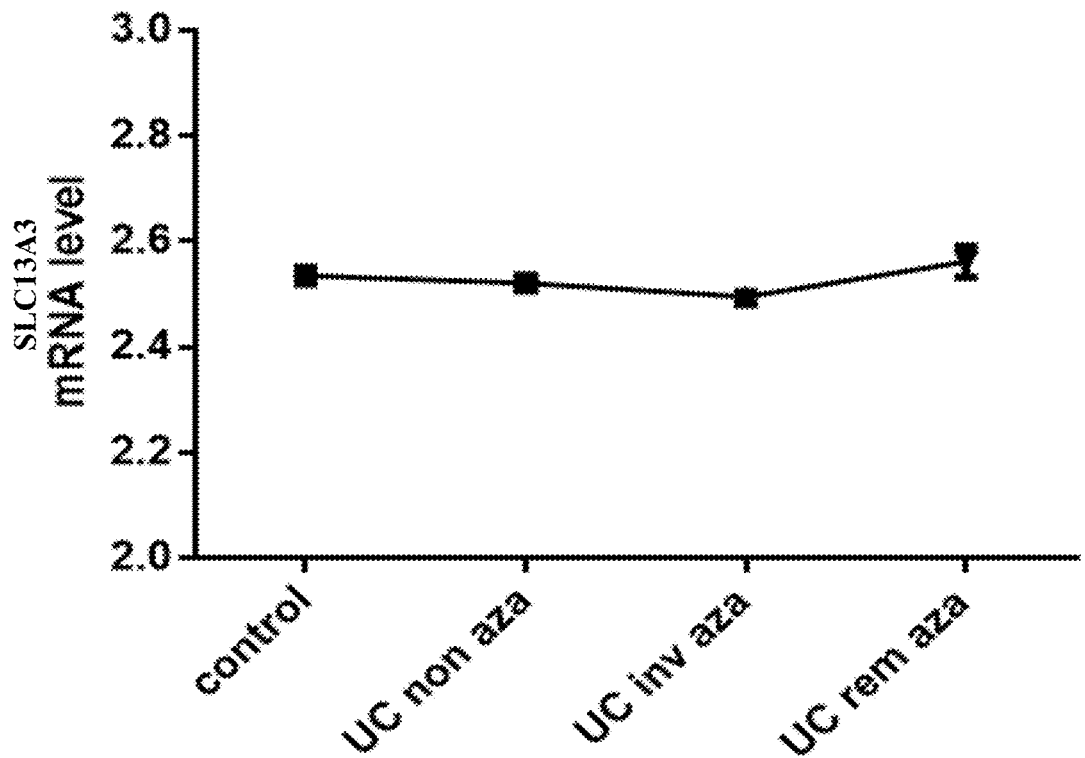

Much research has been done on the dysbiosis that exists in the gut of a patient with inflammatory bowel disease. Unfortunately, the results are often contradictory, and exactly which microbiota and which metabolites from those microbiota are upregulated is not always clear. It was determined that several succinate-producing strains of gut microbiota are more abundant during IBD (FIG. 1A). These microbiotas were elevated in patients with Crohn's disease (CD), ulcerative colitis (UC) and Behcet's disease, although to varying degrees. Further, it was found that succinate, and to an extent citrate, were capable of shifting macrophages toward a proinflammatory phenotype; further succinate given in an enema at the concentration produced by these microbiotas caused colonic ulcerations in mice. Analysis of published gene expression databases indicates that mucosal tissues of azathioprine (aza)-treated patients have elevated SUCNR1 (FIG. 1B) and reduced succinate transporter slc12a2 (NaDC-1) (FIG. 1C) expression compared to healthy subjects. Another succinate transporter, slc13a3 was not modified (FIG. 1D).

Figure 1E:
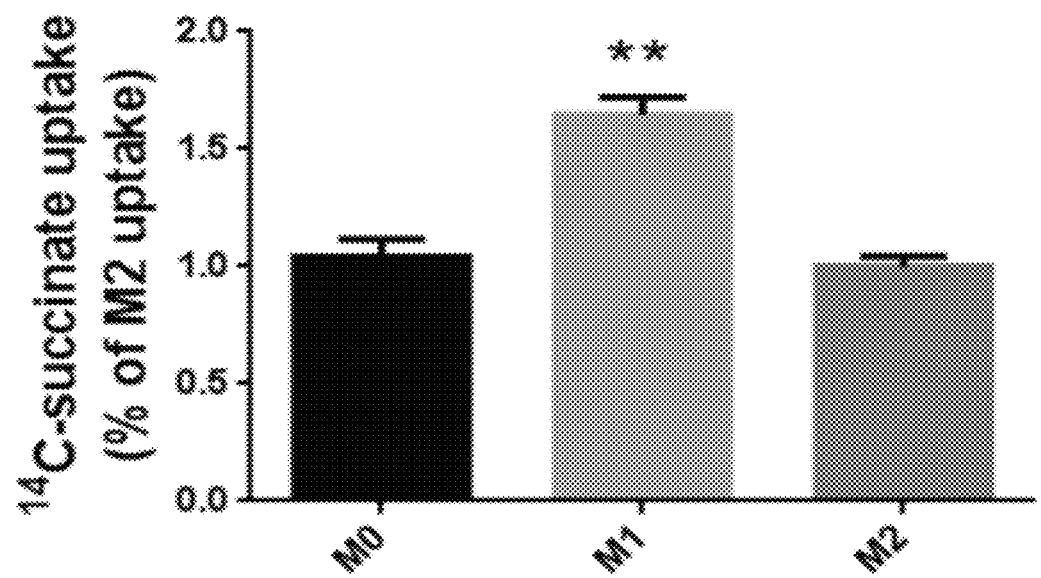
Figure 1F:
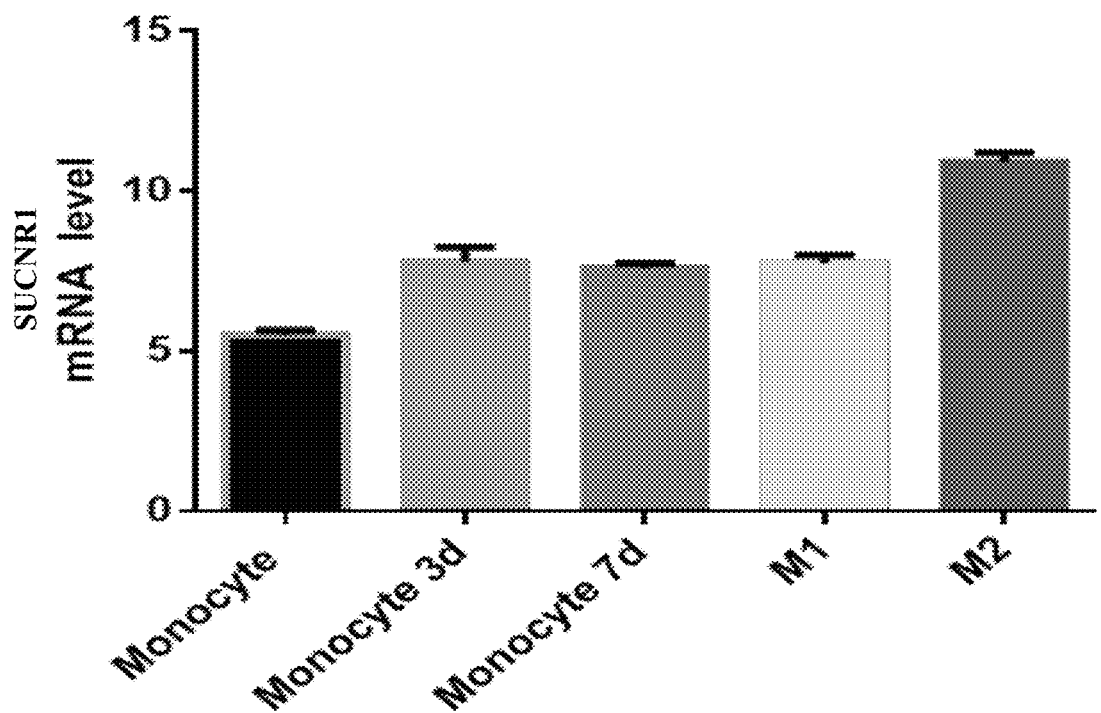
Figure 1G:
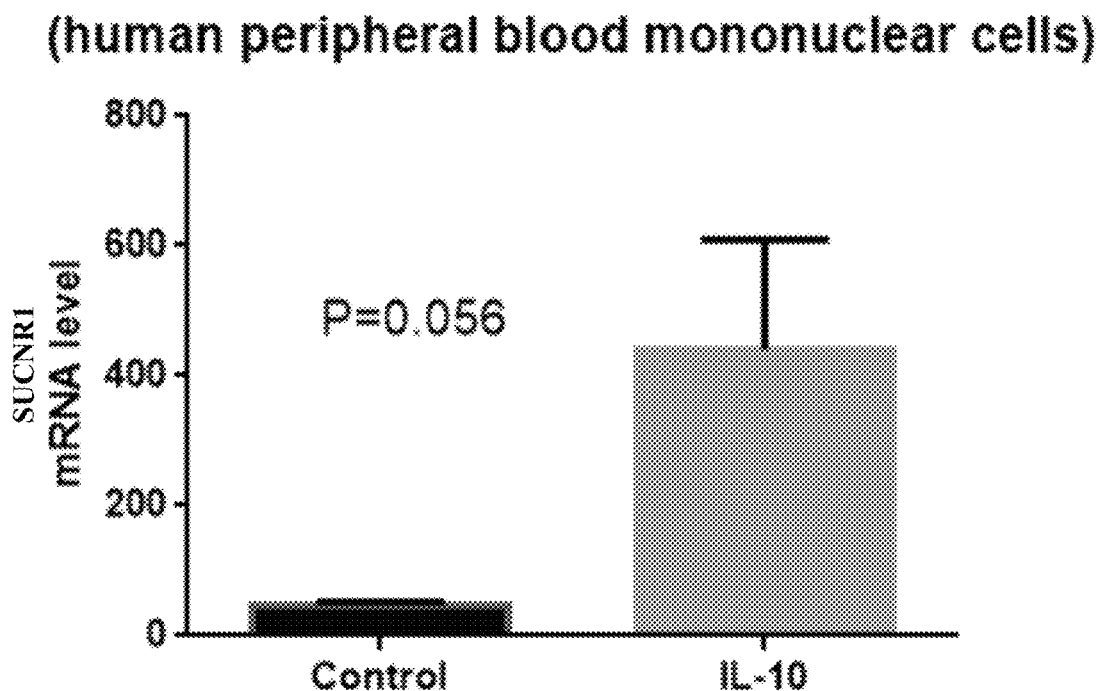

Not only does elevated intracellular succinate and citrate induce macrophages to a proinflammatory state but by examining mouse M0, M1 and M2 macrophages it was determined that there was increased succinate uptake in M1 macrophages as compared to M0 and M2 (FIG. 1E). Analysis of published human gene expression data indicates that SUCNR1 mRNA is increased in anti-inflammatory M2 macrophages (FIG. 1F), and anti-inflammatory IL-10 elevates SUCNR1 expression in mononuclear cells (FIG. 1G). As such succinate and citrate are not only metabolic intermediates of the Krebs cycle, they also function as pivotal inflammatory mediators. Further, when excessively absorbed, succinate becomes a metabolic poison, while urinary citrate concentrations drop leading to IBD, nephrolithiasis and related hypertension. As such, removal of excess succinate and/or addition of a SUCNR1 mimic or analog is a viable strategy for treating bowel inflammation.

Example 2: Succinate Levels in Inflammatory Bowel Disease

Figure 1H:
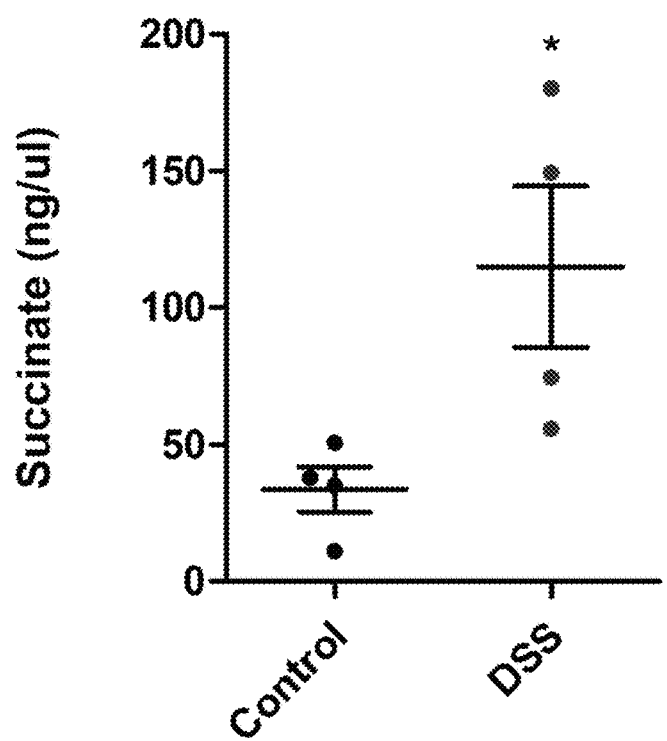

Knowing that gut microbiota that produce succinate are more abundant in subjects suffering from IBD, the levels of succinate found in IBD stool was measured in a mouse model. C57BL/6 mice were induced of acute colitis by dextran sulfate sodium (DSS) treatment. Specifically, induction of colitis was carried out in 4 male mice by supplementing the drinking water (2.5% wt/v) with DSS (mol. wt. 36,000-50,000). Succinate in stool from the mice was measured using the succinate colorimetric assay kit from Sigma-Aldrich (cat #: MAK184). 10 mg of sample were treated with 100 ul of succinate assay buffer; and a stand curve was made to calibrate the assay. The assay provided succinate concentration in nanomoles, and as the molecular weight of succinate is 118.09 g/mole the concentration could be provided as ng/ul. All future samples were diluted in order to fit within the linear range of the calibration curve. All 4 DSS treated mice were found to have increased succinate levels in their stool as compared to 4 control mice (FIG. 1H). Indeed, every DSS treated mouse had greater succinate stool levels than every control mouse, and two of the four DSS treated mice showed a ~3× increase. The difference in stool succinate was found to be significant at a p-value of 0.0385.

Figure 1I:
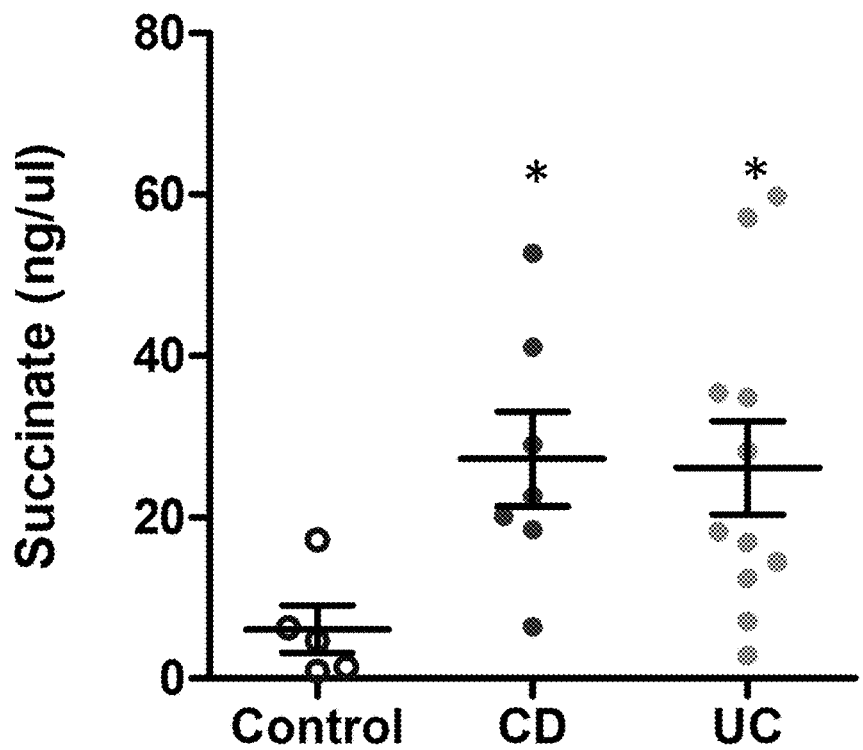
Figure 1J:
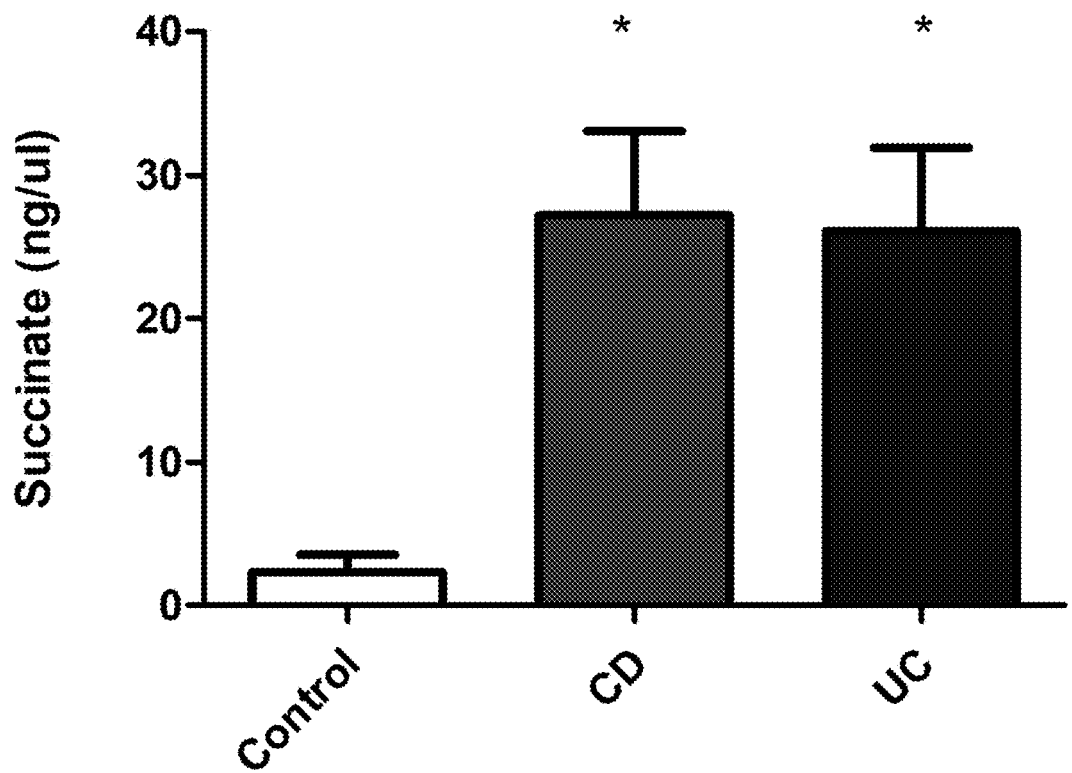

11 patients stuffing from Crohn's disease (CD) and 22 suffering from ulcerative colitis (UC) provided stool samples that were assayed. These samples were assayed either by the same colorimetric assay kit as the mice (Sigma-Aldrich) or by the succinic acid colorimetric assay kit from Abcam (cat #ab204718). Both patients suffering from CD and those suffering from UC had significantly increased levels of succinate in their stool (FIG. 1I), with the average succinate levels in CD and UC being about equal and ~6× higher than the average of the 13 healthy control subjects assayed (FIG. 1J).

Figure 2A:
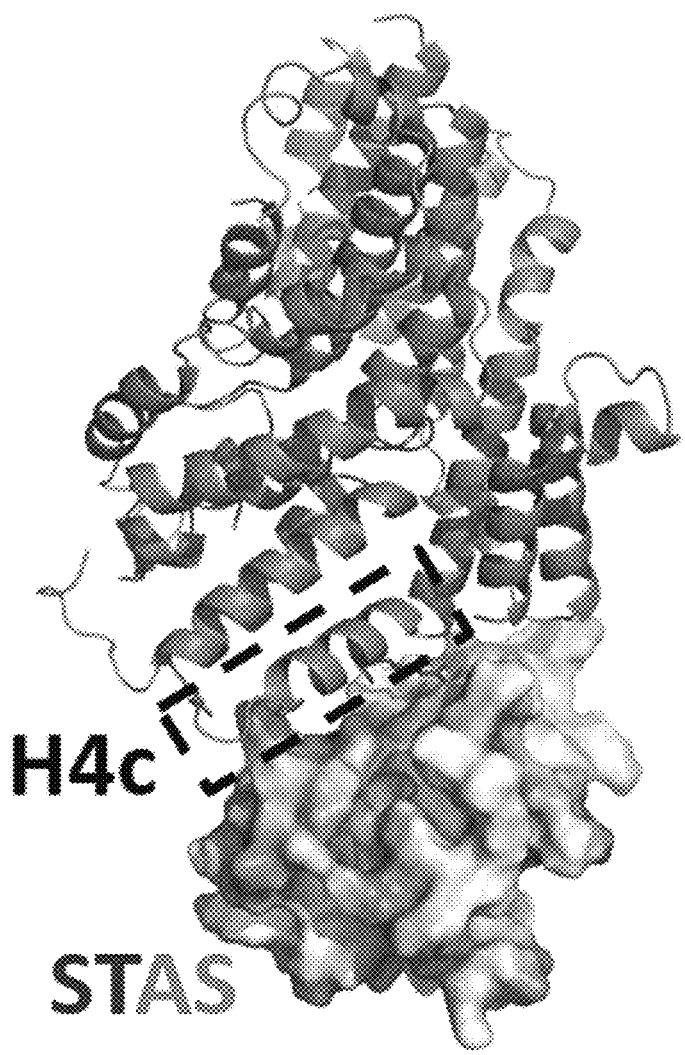
Figure 2B:
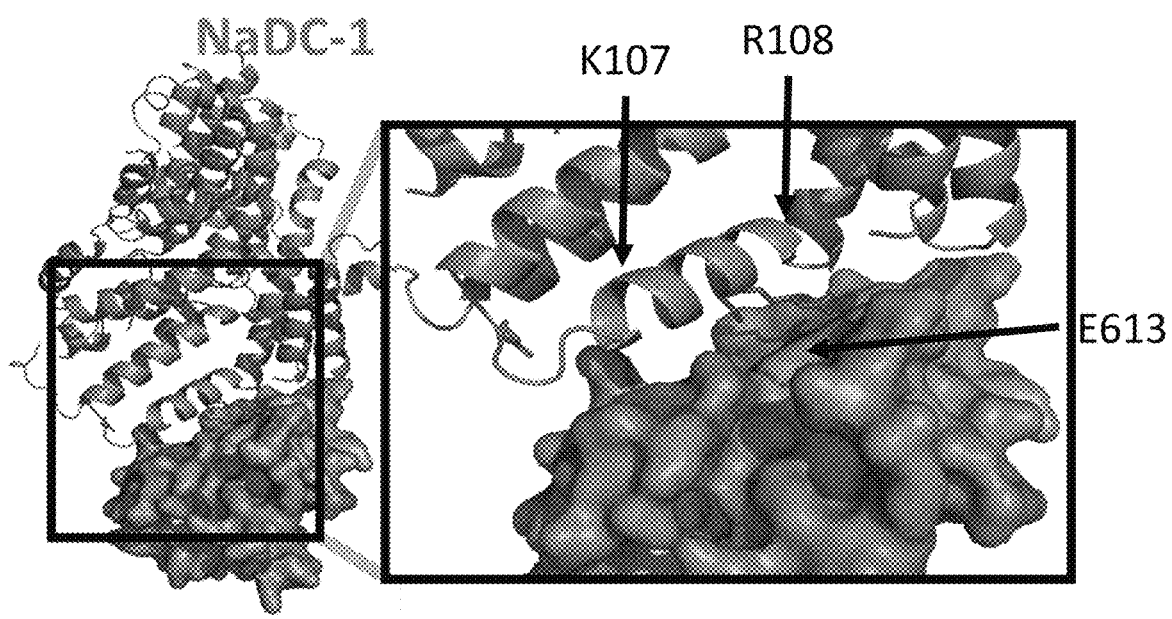
Figure 2C:
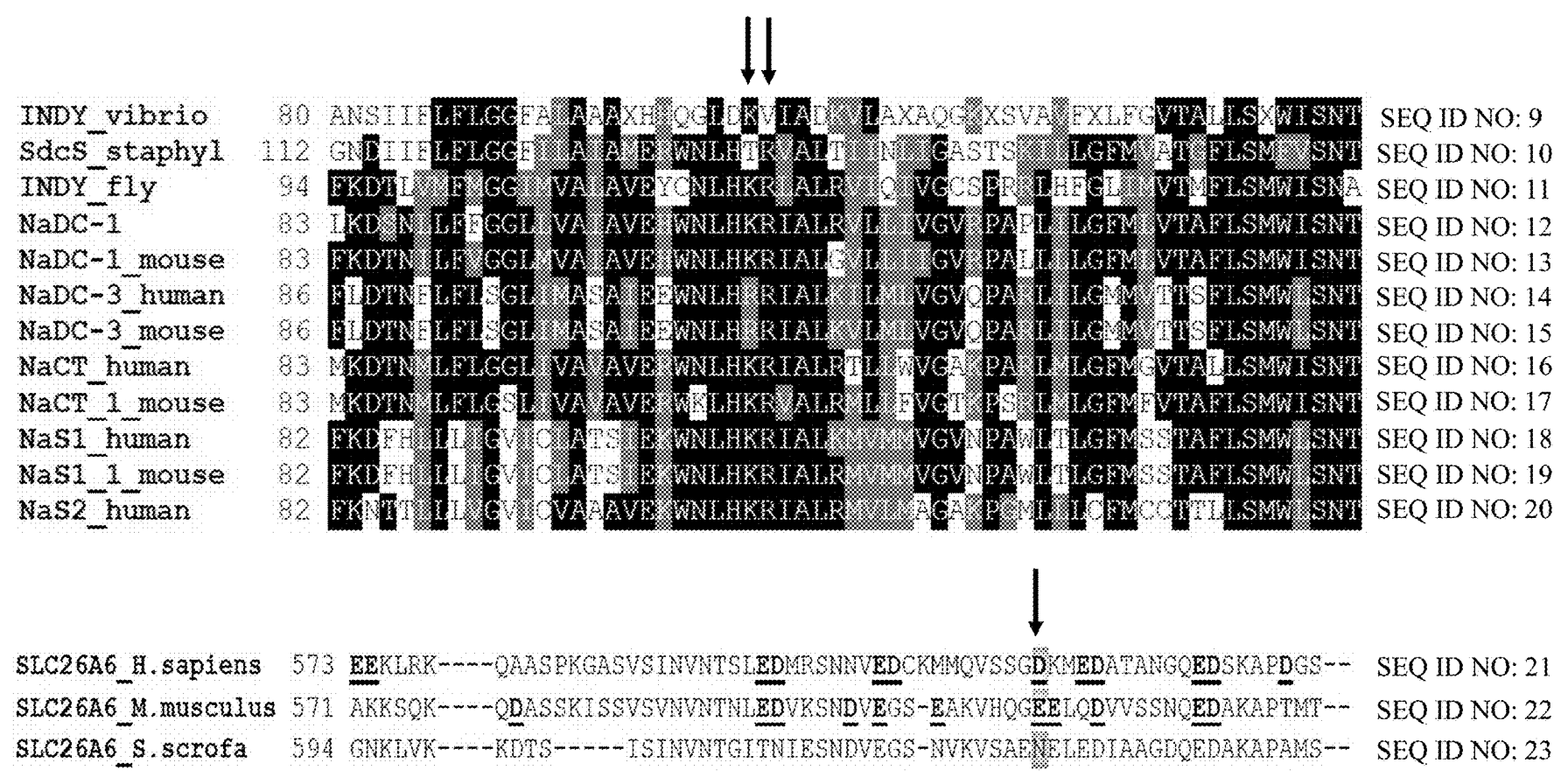

Example 3: Charged Residues in NaDC-1 and slc26a6-STAS Binding Regions are Crucial for Protein-Protein Interaction and Regulation To further understand the molecular mechanism of NaDC-1 inhibition by slc26a6 which controls succinate and citrate homeostasis, in silico analysis was initially used to predict the putative NaDC-1 and slc26a6-STAS structures based on published crystal structures of vcINDY and slc26a5-STAS, respectively. In addition, the interaction between the two putative structures was predicted using the HADDOCK software. Based on the putative model of interaction between NaDC-1 and the slc26a6-STAS, there was identified a negatively charged surface region on slc26a6-STAS that includes E613 that is spatially oriented to potentially interact with a positively charged area of NaDC-1 that includes K107 and R108 (FIGS. 2A and 2B). Since the NaDC-1 H4c region faces the intracellular milieu, it could interact with the slc26a6-STAS which is also intracellular. Importantly, the positively charged residues K107 and R108 on H4c are conserved among the slc13 family members (FIG. 2C). Based on these findings it was hypothesized that the interaction between slc26a6-STAS and NaDC-1 is electrostatic and mediated by NaDC-1(K107 and R108) and slc26a6(E613).

Figure 3A:
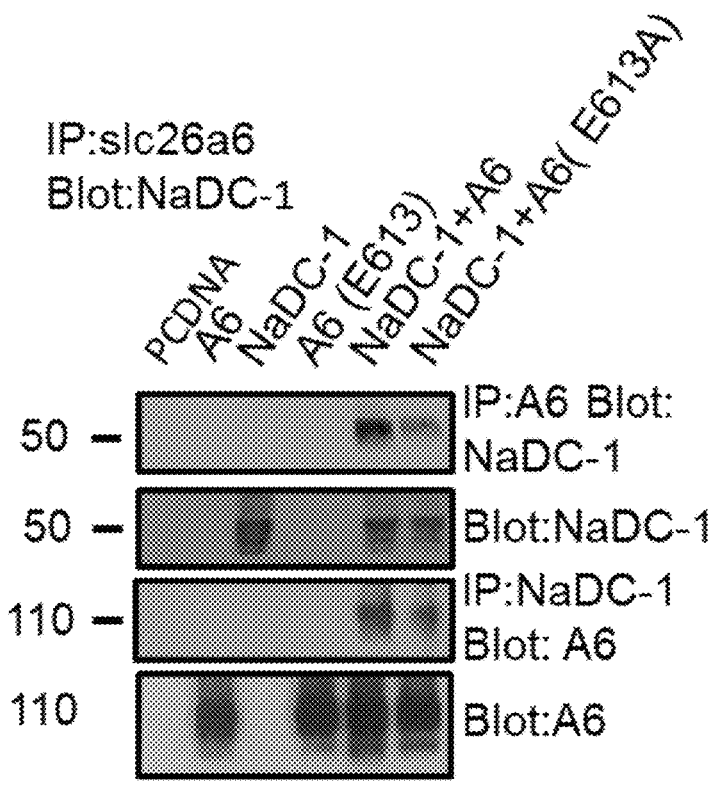
FIGS. 3A-D: The slc26a6(E613A) mutation affects slc26a6-mediated oxalate transport, interaction with NaDC-1 and regulation of succinate transport. (3A) Photographic blots of co-immunoprecipitation (CoIP) of WT NaDC-1, WT slc26a6, and slc26a6(E613A). (3B) Dot plot summary and representative tracings of NaDC-1-dependent $Na^+$-succinate current in $Xenopus$ oocytes expressing NaDC-1, either alone (black), with WT slc26a6 (light gray), or with slc26a6(E613A) (dark gray). Dot plot summaries and representative traces of the current (3C) and changes in intracellular $Cl^-$ (3D) mediated by slc26a6 and the indicated mutants in $Xenopus$ oocytes.
Figure 3B:
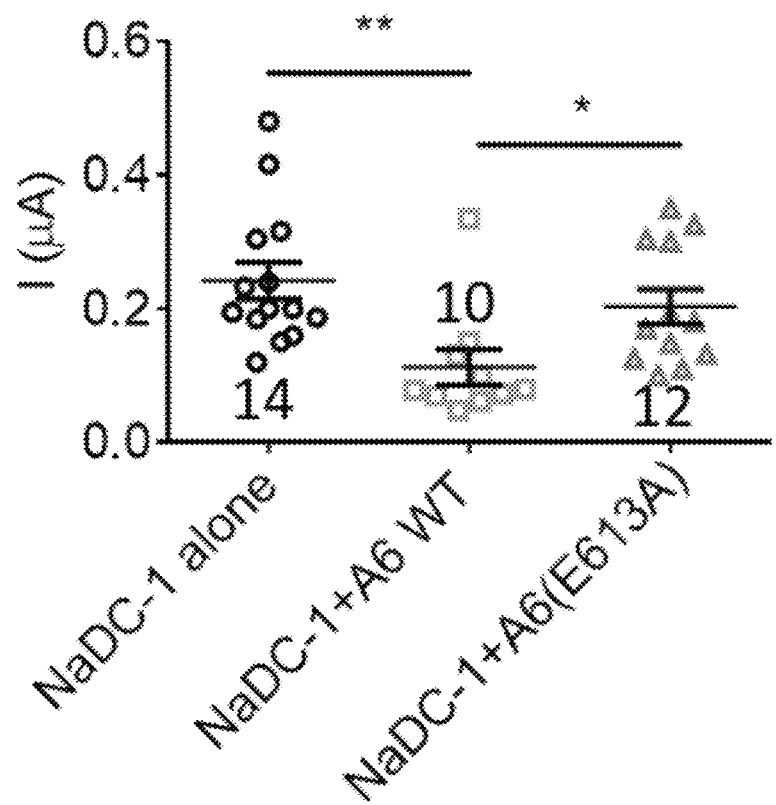
Figure 3B:
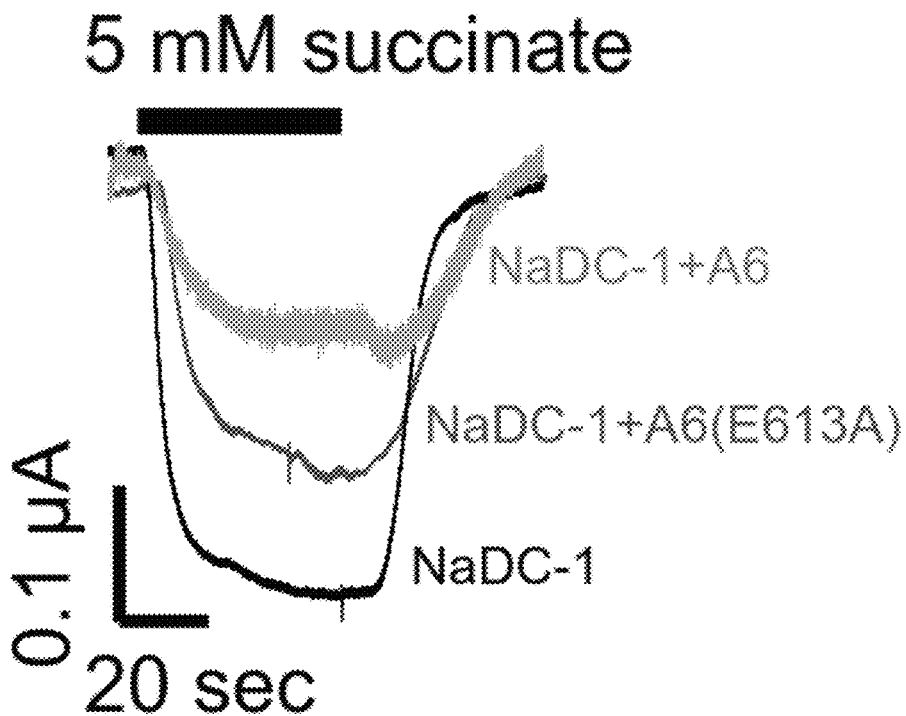
Figure 3C:
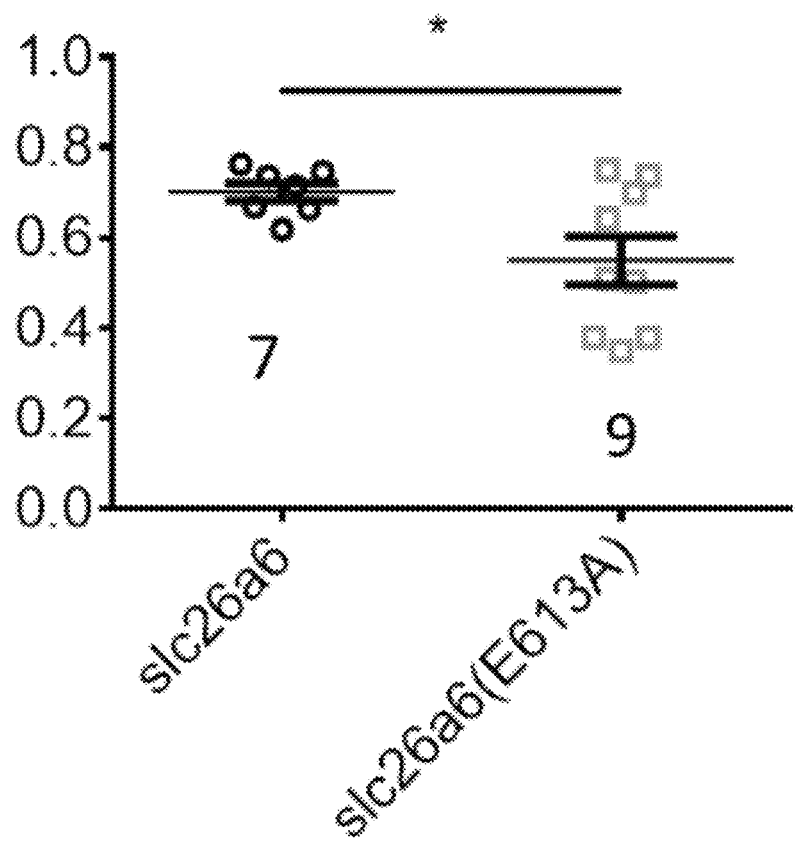
Figure 3C:
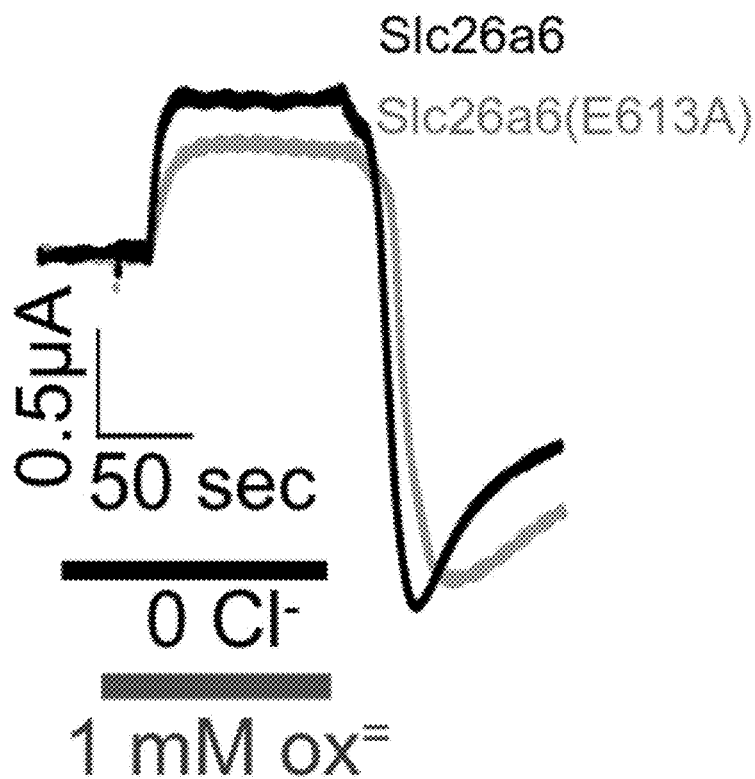
Figure 3D:
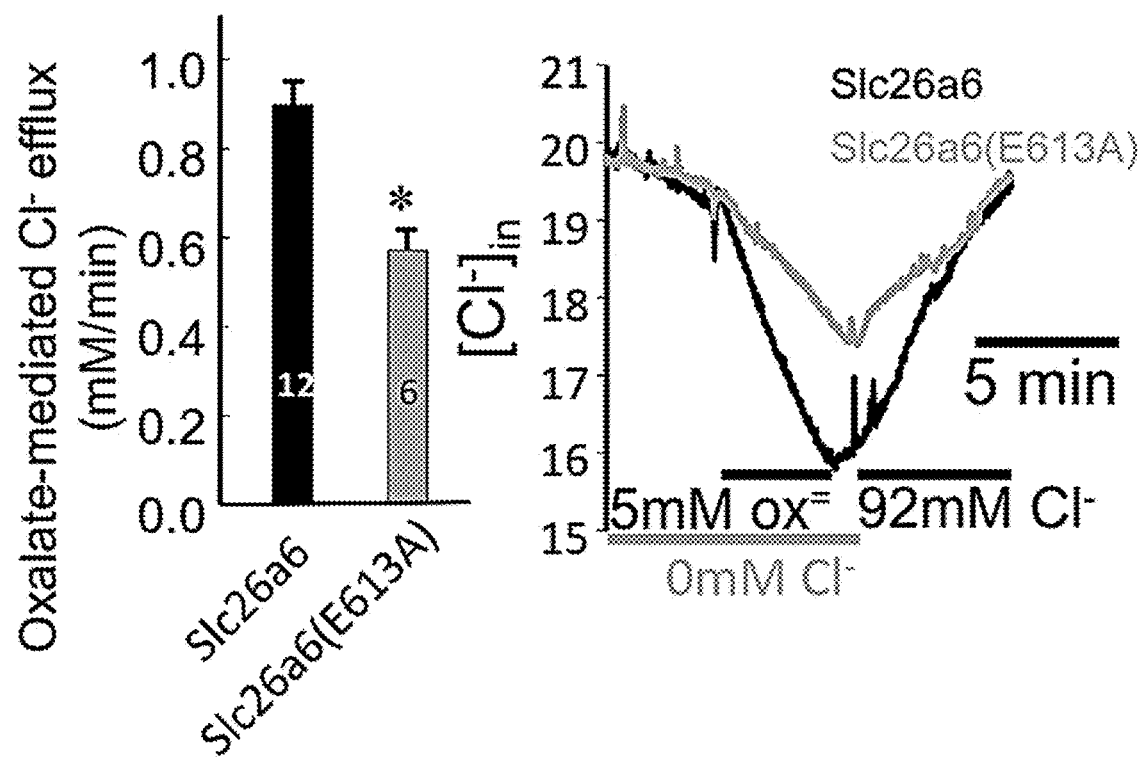

To test this model and study the role of distinct residues in the NaDC-1-slc26a6 interaction, several mutations on both NaDC-1 and slc26a6 were generated that neutralize the charges at the predicted interaction site, namely, slc26a6 (E613A) and NaDC-1(K107A, R108A), and monitored the effect of the mutations on the NaDC-1-slc26a6 interaction using co-immunoprecipitation (coIP). The slc26a6(E613A) mutant showed a reduced interaction with NaDC-1 (FIG. 3A). To determine the functional implications of this reduced interaction, succinate transport activity was monitored by using electrophysiological measurements in *Xenopus* oocytes expressing NaDC-1 alone, with slc26a6 or slc26a6(E613A). As shown in FIG. 3B, NaDC-1 inhibition by slc26a6 was abolished in cells expressing the slc26a6 (E613A) mutant. Notably, the oxalate transport activity mediated by slc26a6(E613A) was also reduced, namely, by ~30%, as compared with WT (FIGS. 3C and 3D). Based on these results it was reasoned that a reduced oxalate transport by slc26a6(E613A) in the intestine together with an attenuated regulation of NaDC-1 in the proximal tubule of the kidney, may cause hyperoxaluria and hypocitraturia.

Figure 4A:
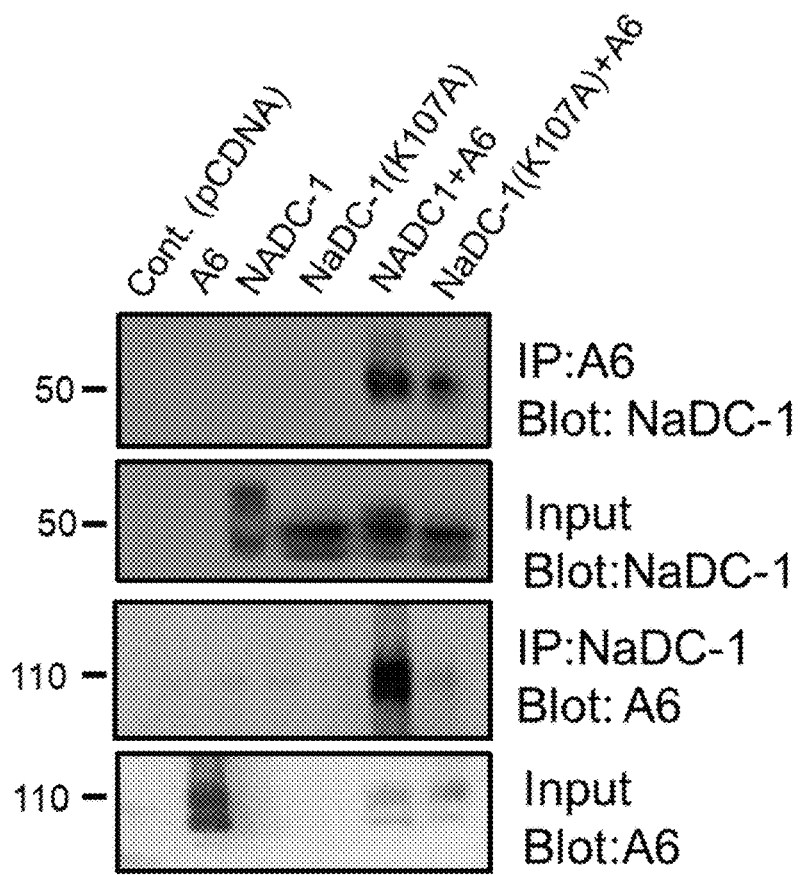
FIGS. 4A-E: The NaDC-1(K107A) mutation affects the interaction with slc26a6 and succinate transport. (4A) Photographic blots of coIP of WT NaDC-1, WT slc26a6 and NaDC-1(K107A). (4B) Dot plot summary and representative traces of the current mediated by NaDC-1-dependent $Na^+$-succinate co-transport in $Xenopus$ oocytes expressing NaDC-1 alone, and NaDC-1(K107A) either alone or in the presence of slc26a6, as indicated. (4C) Photograph of CoIP of WT hNaDC-1 and WT hSLC26a6 (hA6). (4D) Bar chart summary and representative traces of the current mediated by hNaDC-1-dependent Na-succinate co-transport in $Xenopus$ oocytes expressing hNaDC-1 alone and in the presence of hSlc26a6 (hA6), as indicated. (4E) Bar chart showing 14C-succinate uptake, measured in $Xenopus$ oocytes injected with either water (control) hNaDC-1 alone or with hSlc26a6 (hA6). (2 oocyte batches were used for both electrophysiology measurements and 14C-succinate uptake).
Figure 4B:
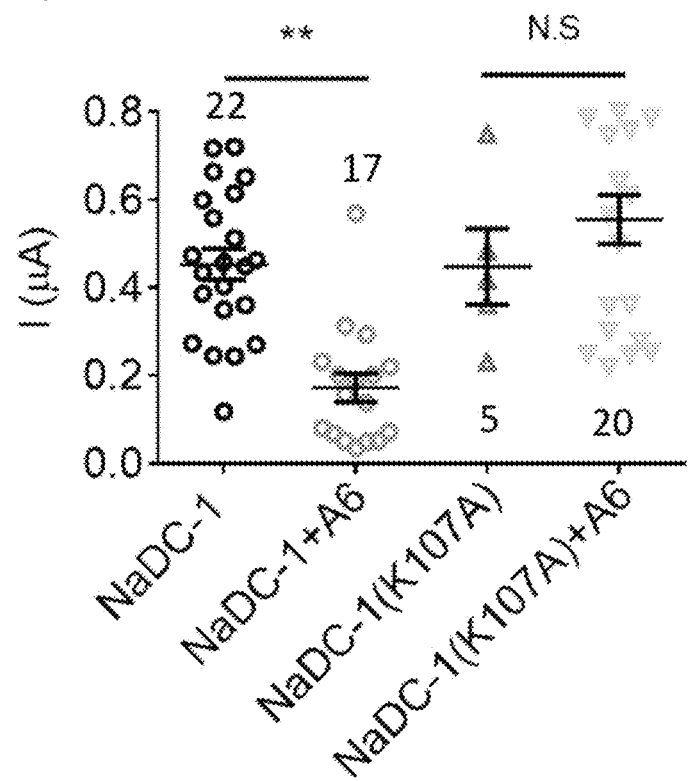
Figure 4B:
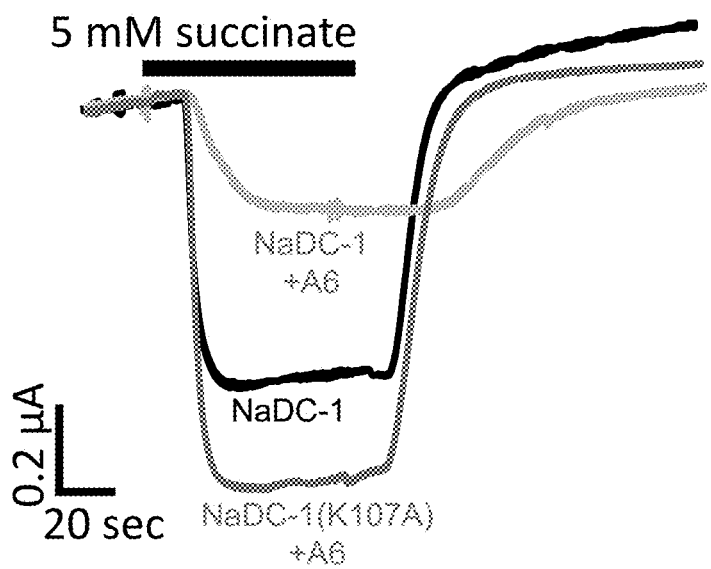
Figure 4C:
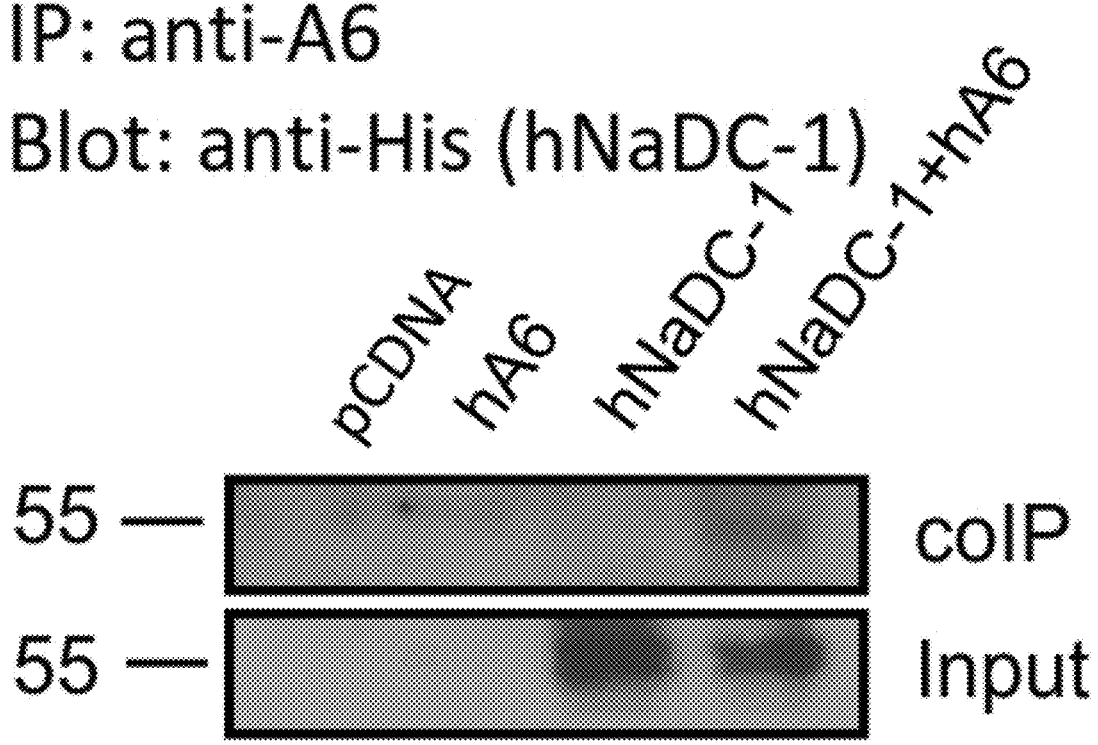
Figure 4D:
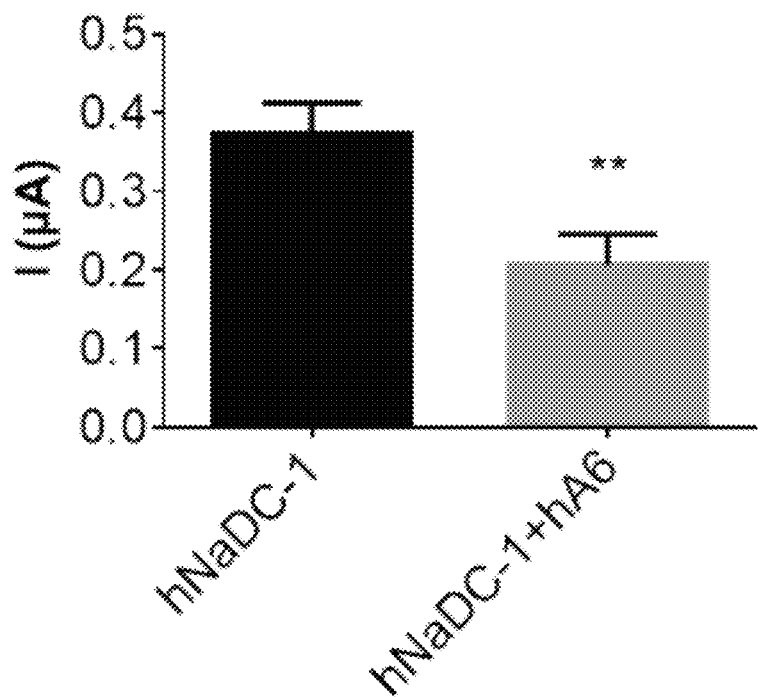
Figure 4D:
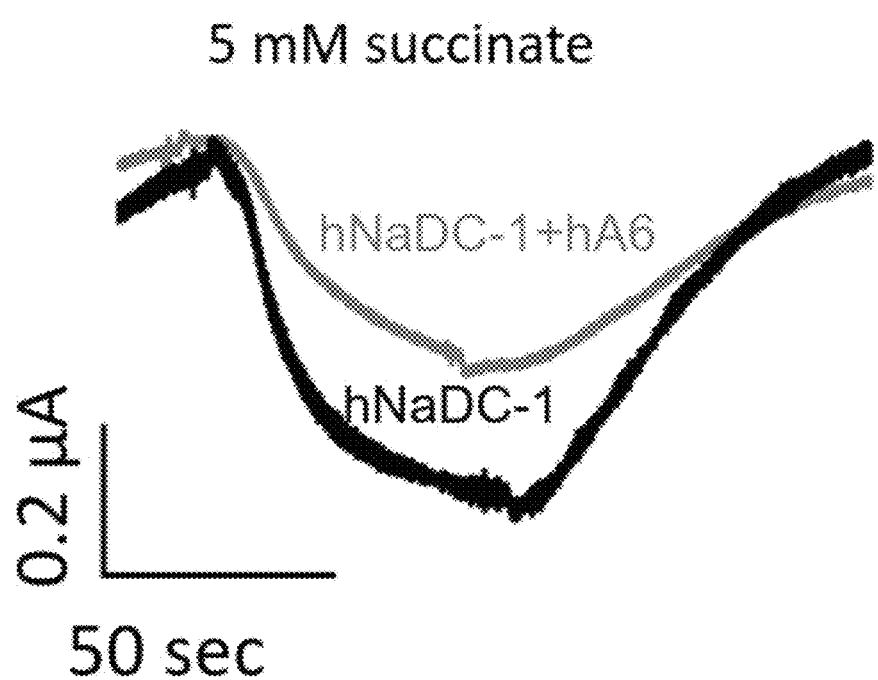
Figure 4E:
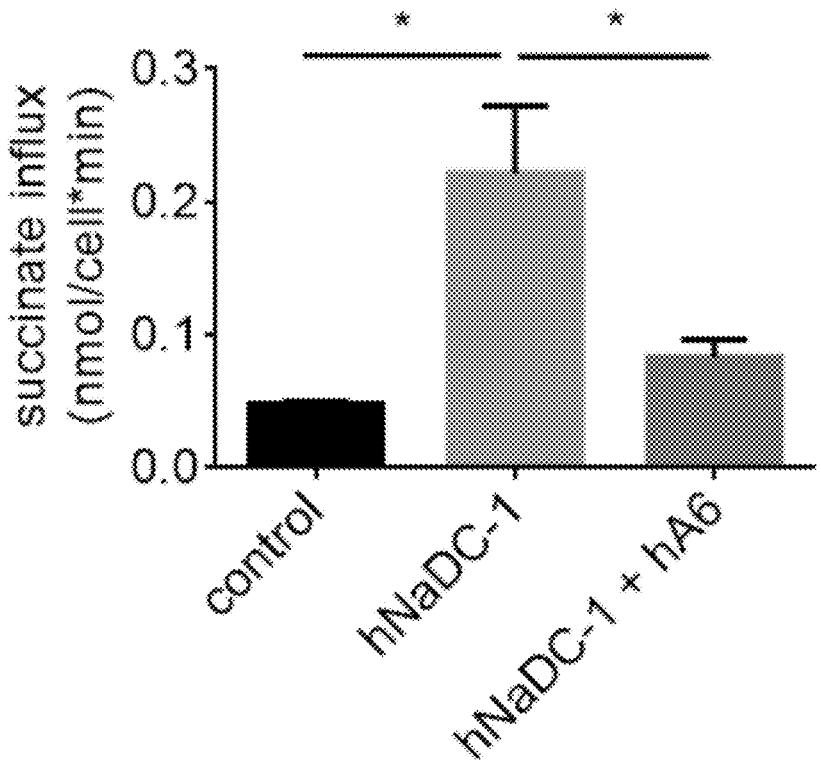

To determine whether NaDC-1(K107) and NaDC-1 (R108) play a role in the NaDC-1-slc26a6 interaction, the effect of slc26a6 on the functioning of NaDC-1(K107A) and NaDC-1(R108A) was tested. It was found that, while NaDC-1(R108A) was inactive, the activity of NaDC-1 (K107A) was retained. Importantly, however, the interaction between NaDC-1(K107A) and slc26a6 was reduced, as compared with the WT NaDC-1 (FIG. 4A). Moreover, NaDC-1(K107A) was not inhibited by slc26a6, which strongly inhibits the WT NaDC-1 (FIG. 4B). These results suggest that NaDC-1-mediated succinate transport and slc26a6-mediated oxalate transport are controlled by the physical interaction between the two transport proteins, and that their interaction is mediated by residue E613 located at the slc26a6-STAS domain and K107 at the NaDC-1 H4c region. Differences between human and mouse slc26a6 have been previously reported. Monitoring interaction (FIG. 4C), and inhibition of human NaDC-1-mediated succinate transport by human SLC26a6 using both electrophysiological measurements (FIG. 4D) and $^{14}$C-succinate flux assay (FIG. 4E) in *Xenopus* oocytes showed that mslc26a6 and hSLC26A6 had similar effects on NaDC-1.

Example 4: Succinate Signaling 'Fine Tunes' Succinate Transport by Controlling the Interaction of IRBIT and NaDC-1

Figure 5A:
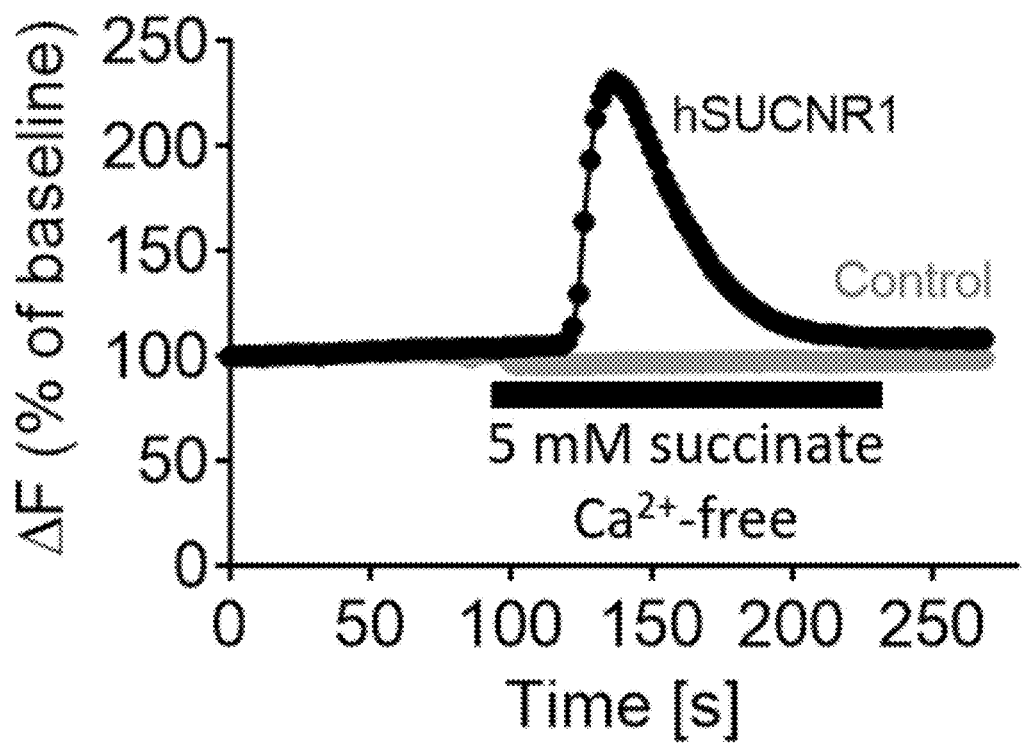
FIGS. 5A-C: Succinate signaling pathway regulates the interaction between NaDC-1 and IRBIT and the NaDC-1-mediated succinate influx. (5A) Line graphs of changes in $[Ca^{2+}]_i$ monitored in HEK293T cells transfected with SUCNR1 (black) or an empty vector (gray control) and stimulated with 5 mM succinate in a $Ca^{2+}$-free solution. (5B) Photographic blots of coIP analysis of HEK293T cells transfected with NaDC-1, IRBIT and/or SUCNR1 and treated with 1 mM succinate for 10 min before lysis. (5C) Dot plot of currents mediated by NaDC-1-dependent $Na^+$-succinate co-transport in $Xenopus$ oocytes expressing NaDC-1, IRBIT and slc26a6, as indicated.
Figure 5B:
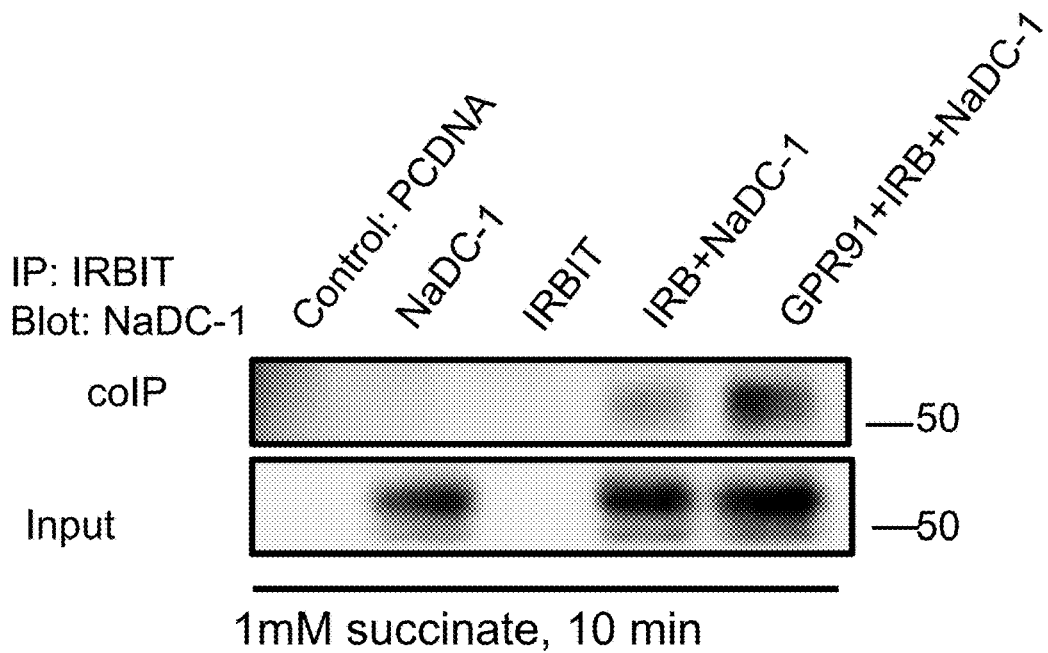
Figure 5C:
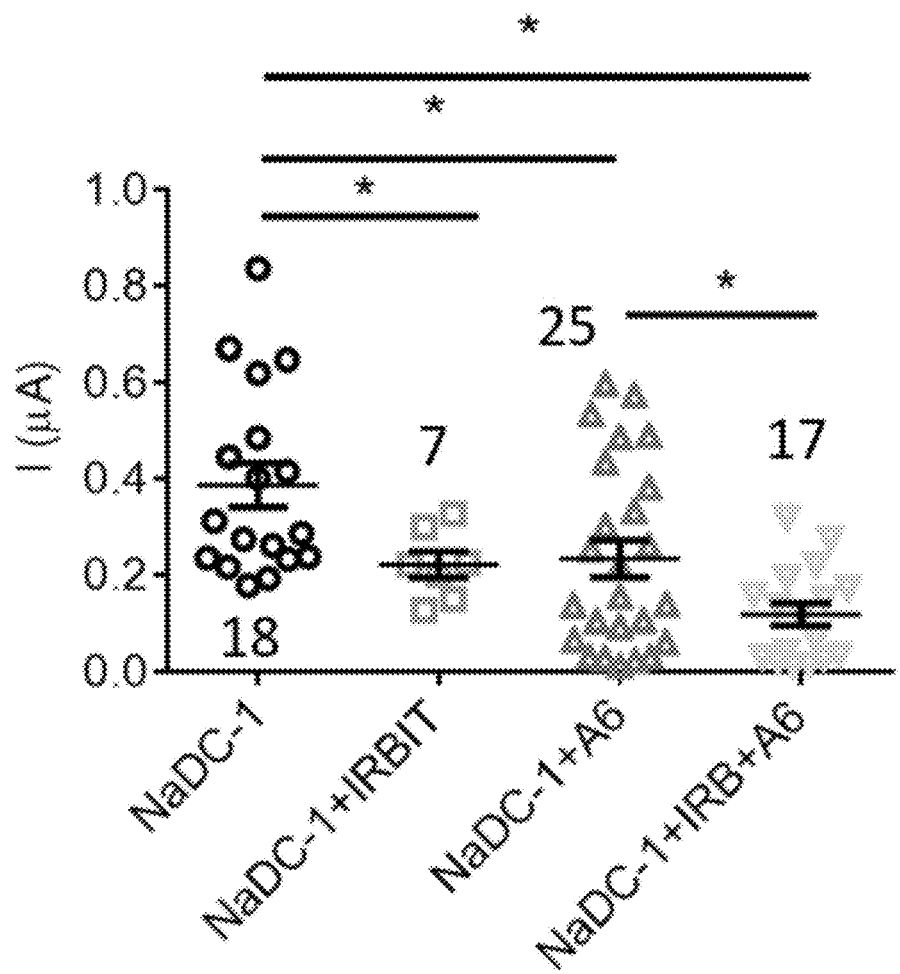
Figure 5C:
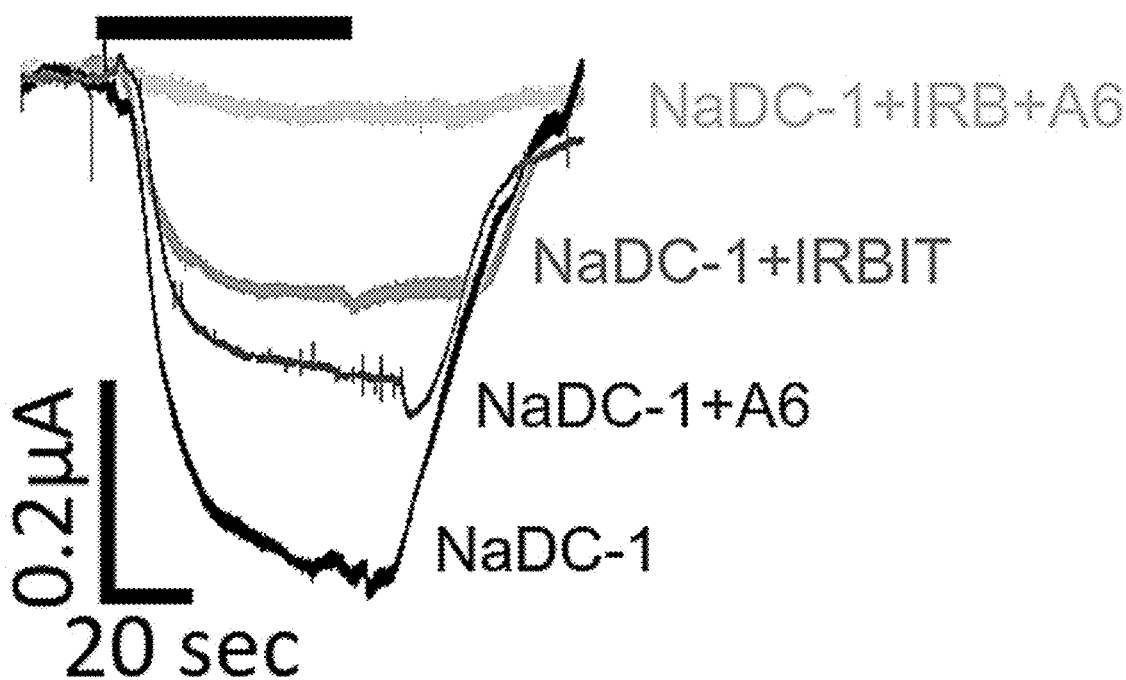

Next it was investigated whether succinate signaling is linked to succinate transport. The succinate receptor, SUCNR1, is a G-coupled receptor expressed on the apical membrane of epithelial cells in the kidney, intestine and other tissues, which acts as either a $G_q$- or a $G_i$- coupled receptor. Cytosolic $Ca^{2+}$ changes were monitored in HEK293T cells transfected with SUCNR1 and it was found that SUCNR1 stimulation by extracellular succinate leads to $Ca^{2+}$ release (FIG. 5A). IRBIT is released from $IP_3R$ upon binding of IP3. It was therefore hypothesized that SUCNR1-stimulated IRBIT release may control the interaction between IRBIT and NaDC-1. HEK293T cells were transfected with NaDC-1, IRBIT and SUCNR1, and their interaction was measured by coIP following activation of signaling with succinate, as indicated in FIG. 5B. The cells were then stimulated with 1 mM succinate for 10 min before lysis and the IRBIT-NaDC-1 interaction was monitored by coIP. It was found that the interaction between IRBIT and NaDC-1 was increased in the presence of the SUCNR1 receptor (FIG. 5B). As an additional strategy to probe the effect of IRBIT on NaDC-1-mediated succinate transport, *Xenopus* oocytes were injected with NaDC-1, slc26a6 and IRBIT and the currents generated by the NaDC-1-mediated Na$^+$-succinate co-transport were measured (FIG. 5C). Both slc26a6 and IRBIT inhibited NaDC-1-mediated succinate transport by ~50%. Significantly, this inhibition was even more pronounced when both IRBIT and slc26a6 were co-expressed with NaDC-1, namely, by ~70% compared with NaDC-1 alone (FIG. 5C). Together, these findings indicate that a functional crosstalk between the SUCNR1 and the succinate transport complex, NaDC-1-slc26a6, occurs via interaction with IRBIT, and that this crosstalk leads to a further downregulation of succinate transport in addition to slc26a6 inhibition. This may act as a metabolic senso-regulatory mechanism which fine tunes transepithelial succinate absorption.

Figure 6A:
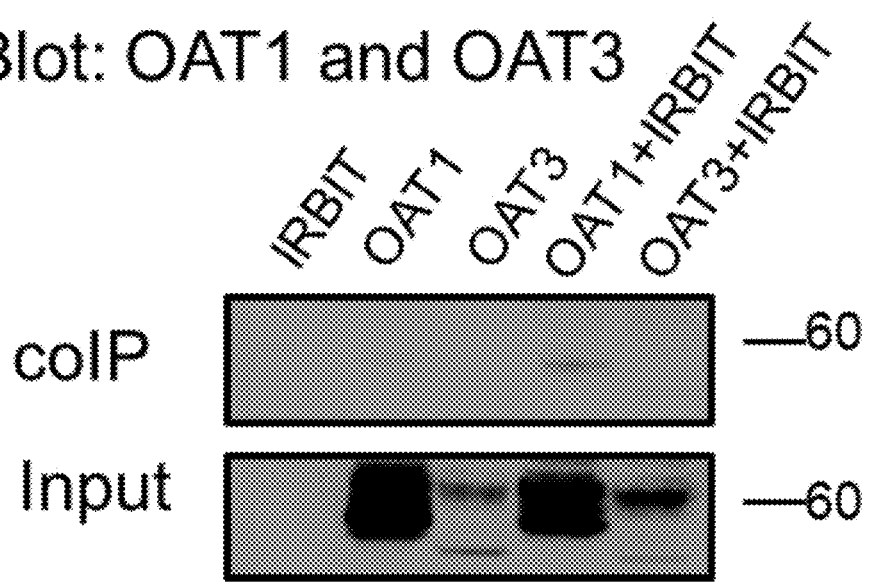
FIGS. 6A-D: IRBIT regulates NaDC-3, but not OAT-mediated succinate transport. (6A) Photographic blots showing lack of coIP of OAT-1 and OAT-3 with IRBIT. (6B-C) Dot plot of $^{14}C$-succinate uptake, measured in (6B) $Xenopus$ oocytes or (6C) HEK293T cells expressing different combinations of OAT-1, SUCNR1, and IRBIT or treated with the PLC inhibitor U73122 or the OAT inhibitor probenecid. Either water injected oocytes or pCDNA transfected cells were used as controls. (6D) Dot plot summary and representative traces of NaDC-3-dependent $Na^+$-succinate co-transport in $Xenopus$ oocytes expressing NaDC-3, either alone (black) or with IRBIT (gray).
Figure 6B:
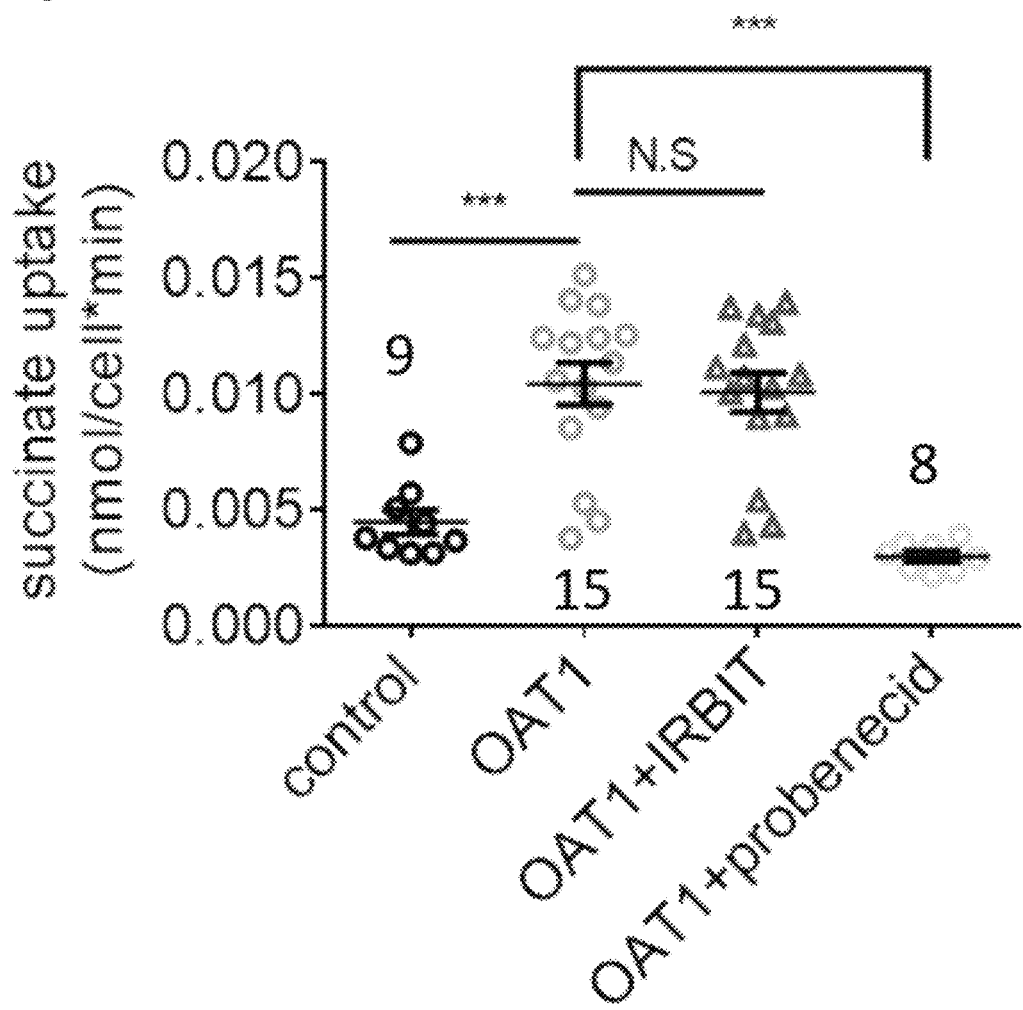
Figure 6C:
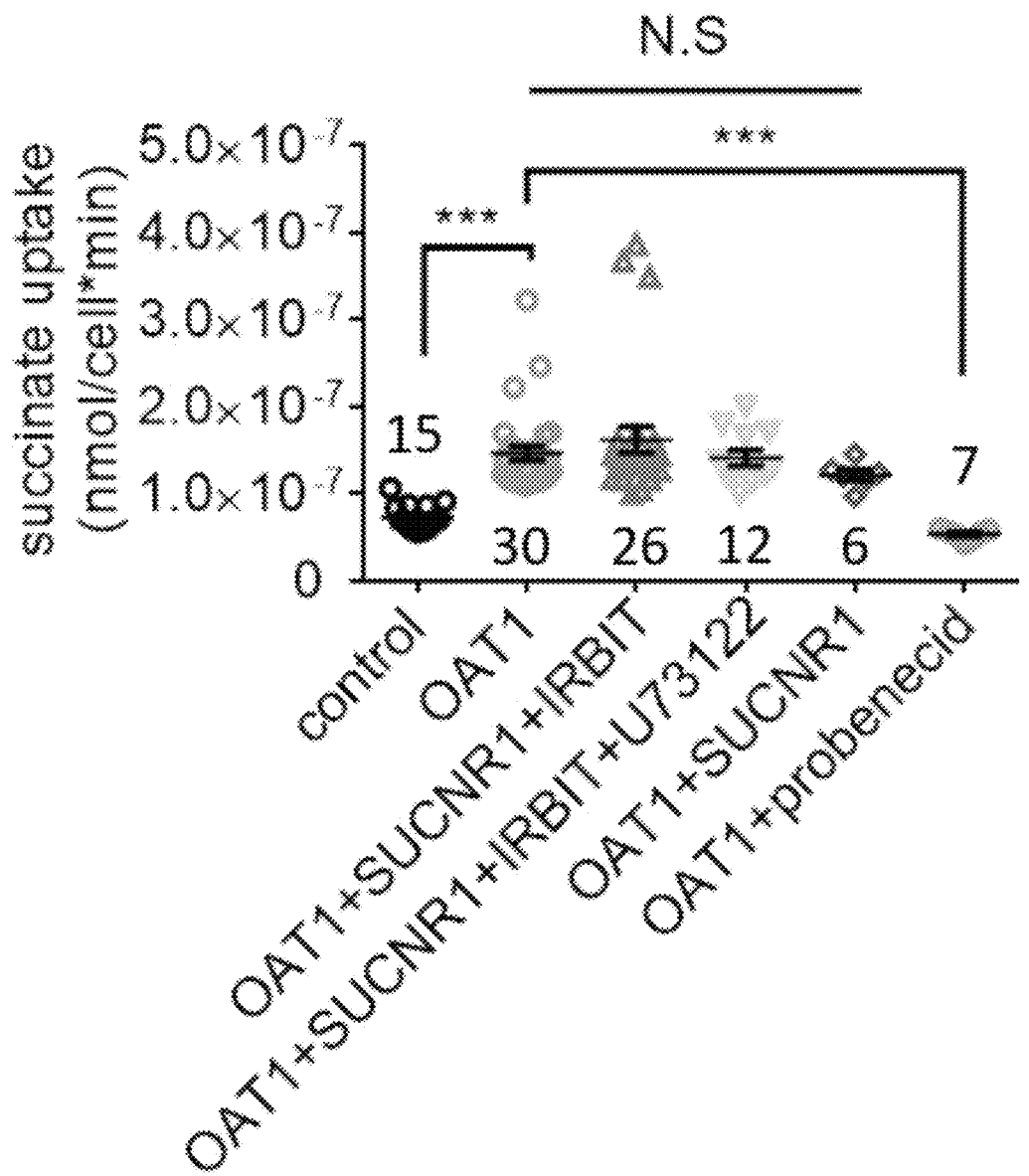

Example 5: Basolateral Succinate Transport by NaDC3, but not by OATs, is Regulated by IRBIT The major basolateral succinate extruders are members of the OAT family and include, most notably, OAT-1, OAT-2 and OAT-3. To determine whether IRBIT regulates succinate efflux via interaction with OATs, the interaction of OAT-1 and/or OAT-3 with IRBIT was monitored by coIP. HEK293T cells were co-transfected with either OAT-1 or OAT-3 in the presence or absence of IRBIT and it was found that the binding of IRBIT to OAT-1 is very low, while its binding to OAT-3 is not detectable (FIG. 6A). Hence, it was tested whether IRBIT regulates the OAT-1 function by monitoring radiolabeled $^{14}$C-succinate uptake into either *Xenopus* oocytes (FIG. 6B) or HEK293T cells expressing OAT-1, IRBIT or both (FIG. 6C). Succinate uptake was elevated by expression of OAT-1 alone, that was abolished by the OAT inhibitor probenecid (FIG. 6B-C). Neither IRBIT, SUCNR1 stimulation, nor inhibition of PLC by U73122 affected the OAT-mediated succinate uptake. These findings indicate that OAT-1 activity is IRBIT-independent.

Figure 6D:
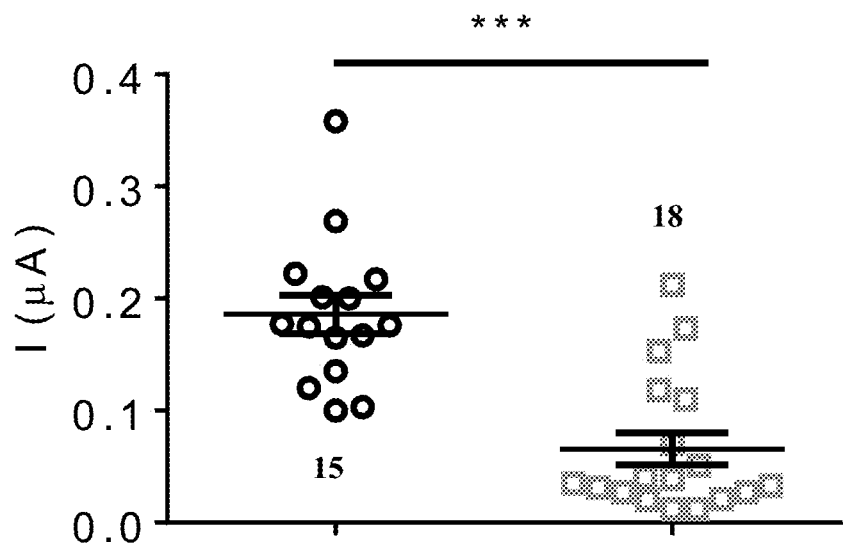
Figure 6D:
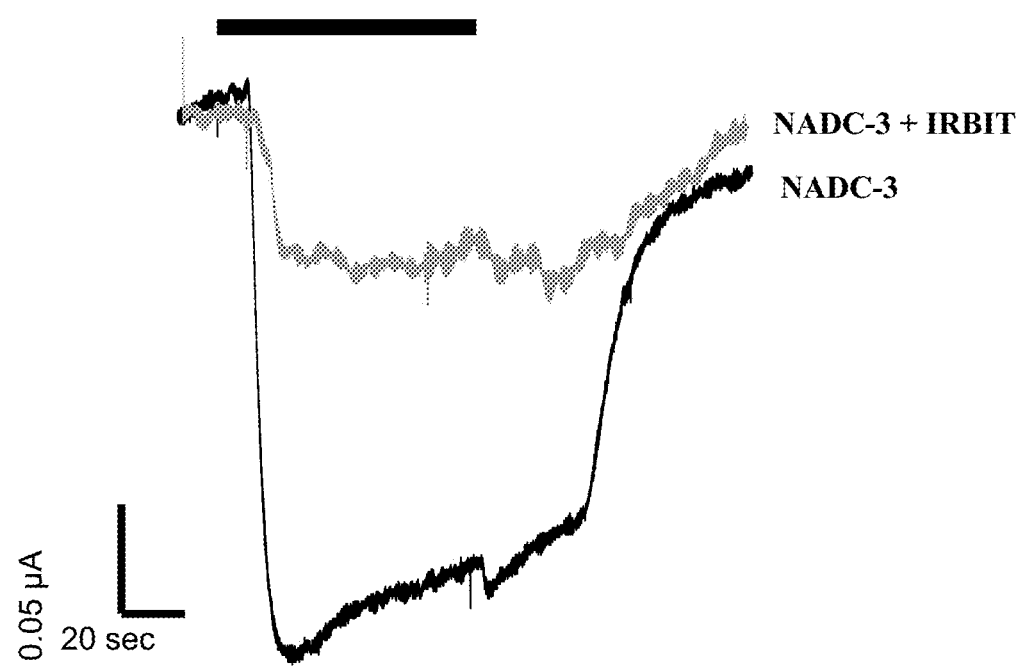

To further investigate the role of succinate signaling via the IRBIT pathway in regulating basolateral succinate transport the effect of IRBIT on the regulation of the basolateral succinate transporter NaDC-3 were monitored. It was found that succinate currents in *Xenopus* oocytes, injected with both NaDC-3 and IRBIT, are dramatically inhibited, as compared with those in oocytes expressing NaDC-3 alone (FIG. 6D). This finding indicates that signaling via the IRBIT pathway orchestrates succinate influx—but not efflux—in both the apical and basolateral membranes by transporters that import succinate in both membranes to control transepithelial succinate/citrate absorption and metabolism.

Figure 7A:
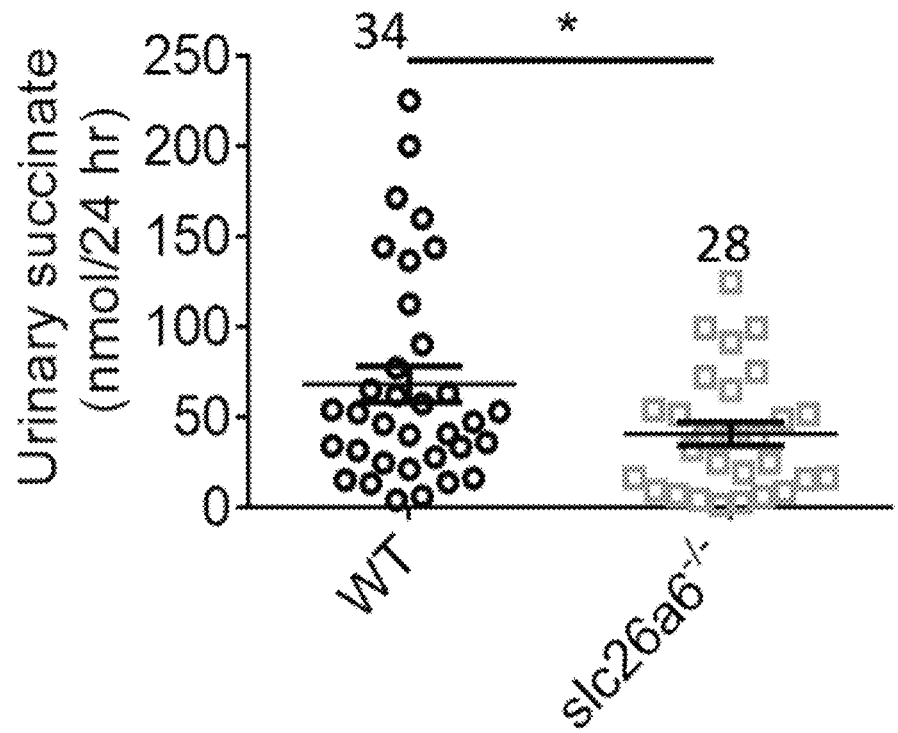
FIGS. 7A-M: Deletion of slc26a6 in mice reduces urinary succinate, elevates plasma renin and increases blood pressure. (7A-D) Dot plots showing (7A) urinary succinate concentration is significantly lower in Slc26a6 mutant mice, (7B) urinary creatinine levels are not significantly different, and (7C) serum succinate and (7D) plasma renin are higher in slc26a6$^{-/-}$ mice, as compared with their WT littermates. (Each data point is an average of 2-3 days of urine samples.) (7D) A line graph of blood pressure measured by telemetry showing higher pressure in slc26a6$^{-/-}$ mice during activity hours, as compared with their WT littermates. (7E) Photo of a western blot, and dot plot summary, of renal expression of SUCNR1 in 5 WT mice, 5 slc26a6−/− mice and 4 WT mice injected with 10 mg/Kg body weight of succinic acid. (7F-G) (7F) Representative blot and (7G) bar graph summary of IRBIT expression analysis in renal lysates from either WT mice, slc26a6 mice or WT injected with 10 mg/1 Kg body weight of succinic acid. The membranes which were exposed to anti-pNCC antibody in FIG. 7L were stripped and exposed to anti-IRBIT. Therefore, similar actin densitometry data was used for the statistical analysis. WB analysis of IRBIT expression in HEK293 cells transfected with either mCherry/Flag tagged IRBIT or untagged IRBIT using a similar anti-IRBIT antibody is provided to confirm detection of the correct protein. (7H) Bar chart showing urinary succinate levels in healthy and Ca2+-oxalate kidney stone forming humans. (7I) Line graph of blood pressure measured for 24 h by telemetry in slc26a6$^{-/-}$ mice and their WT littermates, showing that blood pressure is higher in slc26a6−/− mice during activity hours. There were 6 mice in each group, an average of 5 days is shown. (7J-K) Line graphs showing blood pressure measured for 24 h by telemetry in slc26a6$^{-/-}$ mice and their WT littermates that were fed with either (7J) high- or (7K) low-salt diets. (7L) A line graph of blood pressure monitored in slc26a6$^{-/-}$ mice and their WT littermates during mild physical stress; and a bar graph showing the average systolic blood pressure at the steady state. There were 4-5 mice in each group, and an average of 3 days is shown. (7M) A photograph of a western blot and a dot plot summarizing the expression analysis of phosphorylated NCC (pNCC) in renal lysates of either WT mice, slc26a6−/− mice or WT injected with 10 mg/Kg body weight of succinic acid.
Figure 7B:
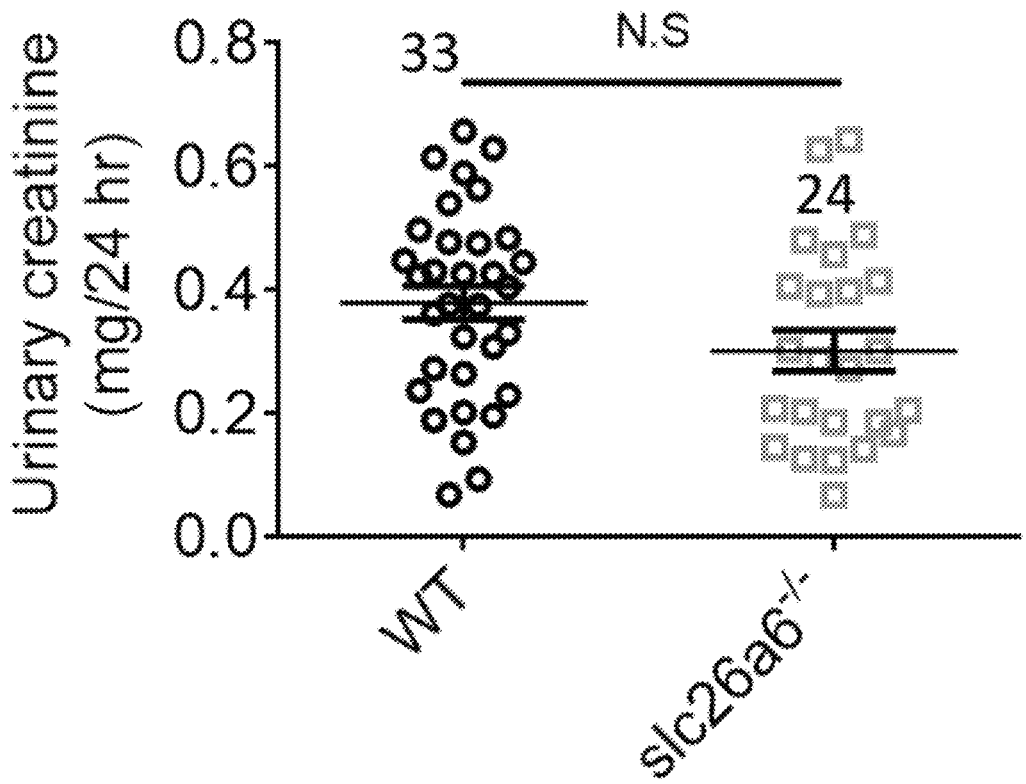
Figure 7C:
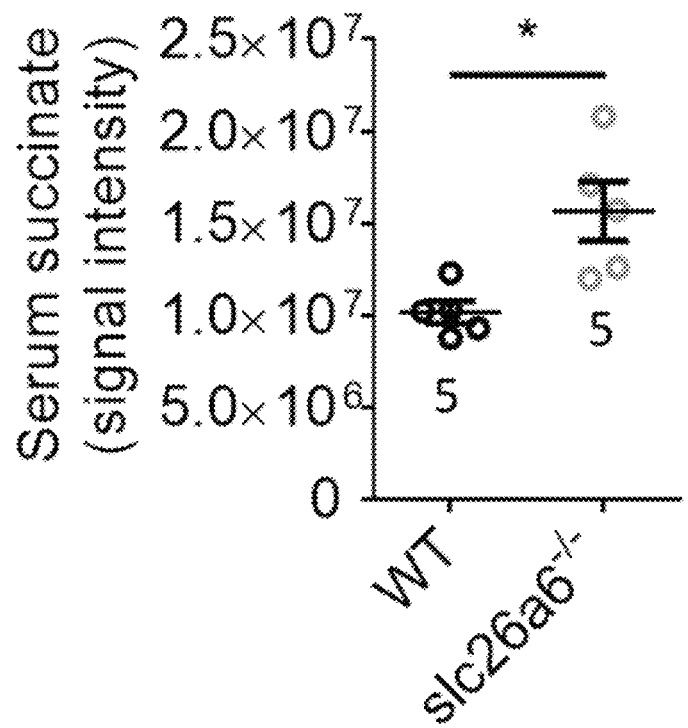
Figure 7D:
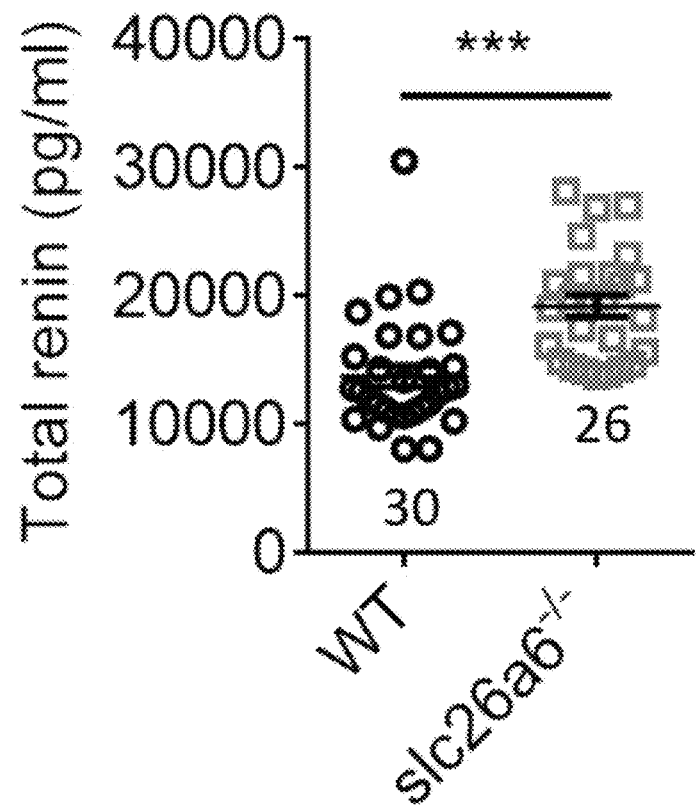
Figure 7E:
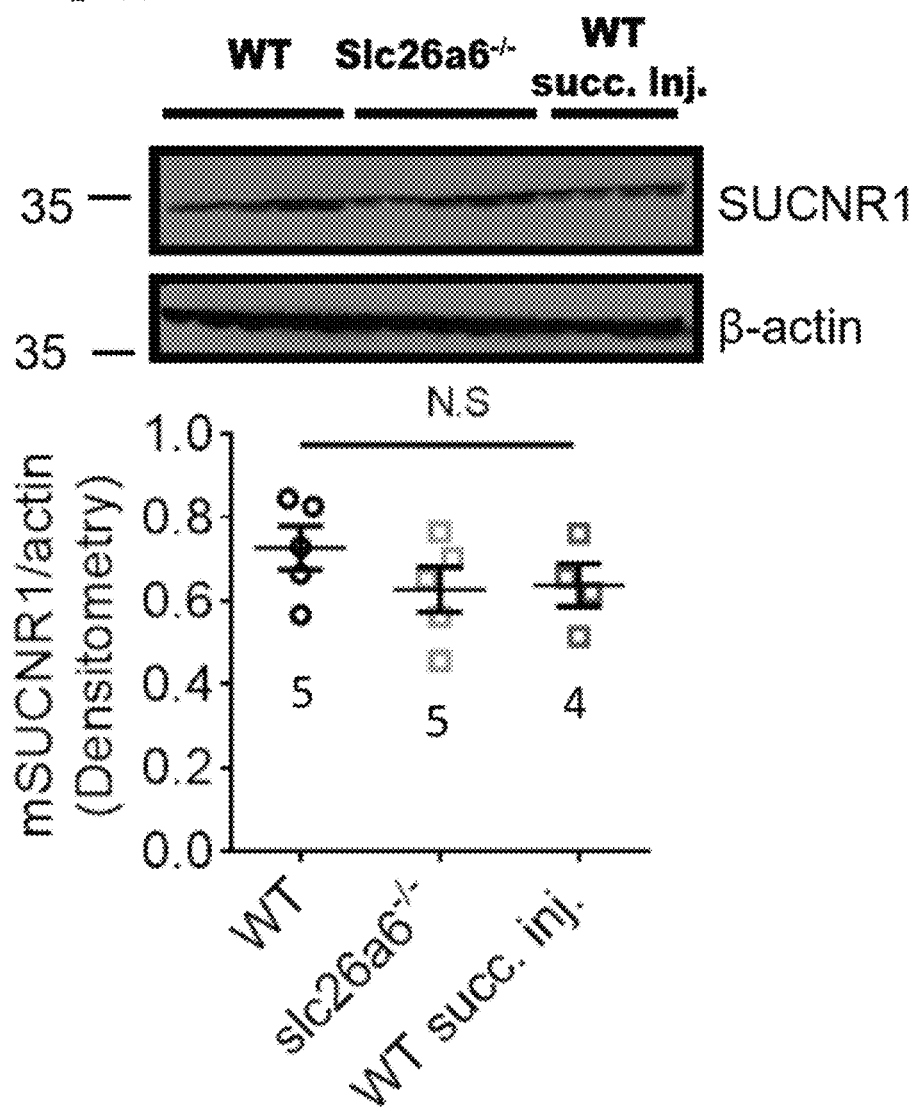
Figure 7F:
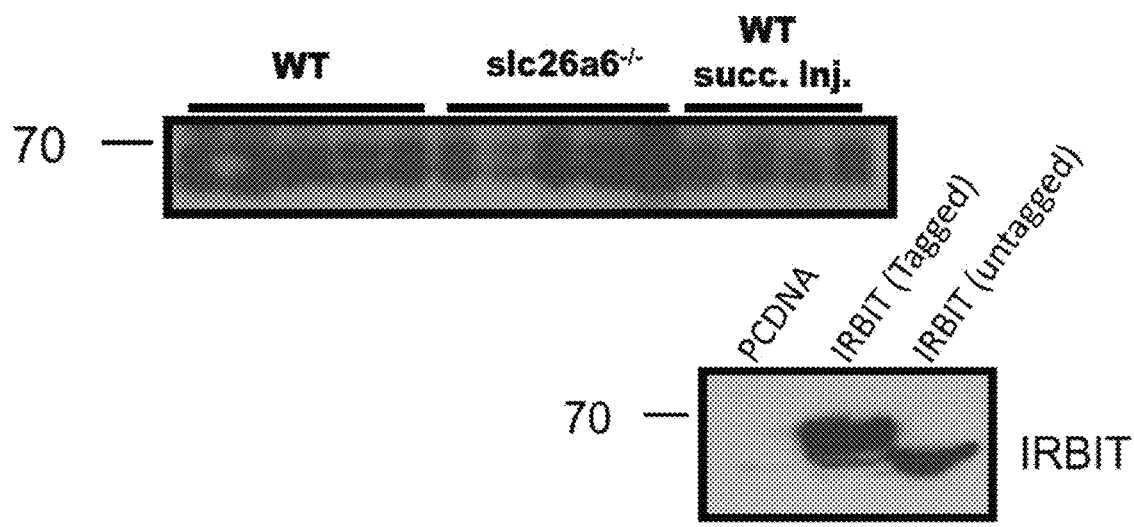
Figure 7G:
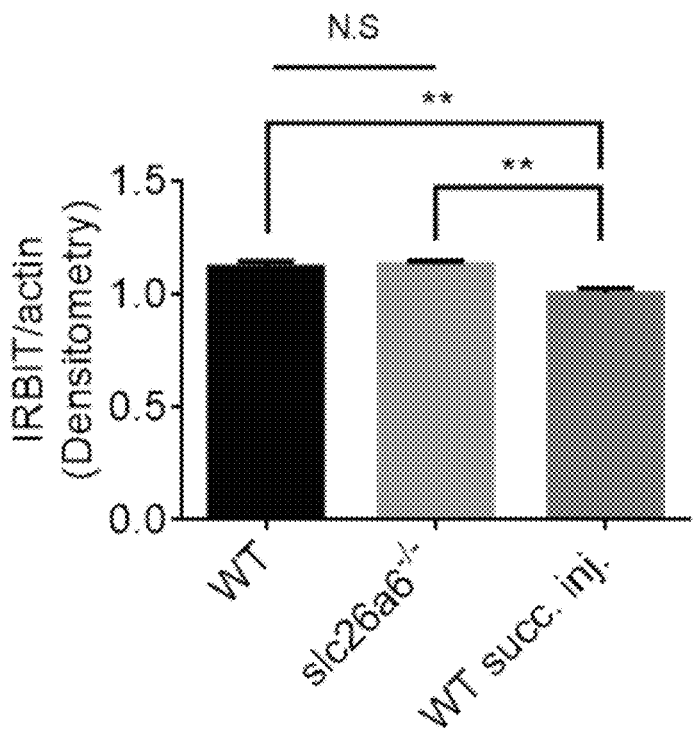
Figure 7H:
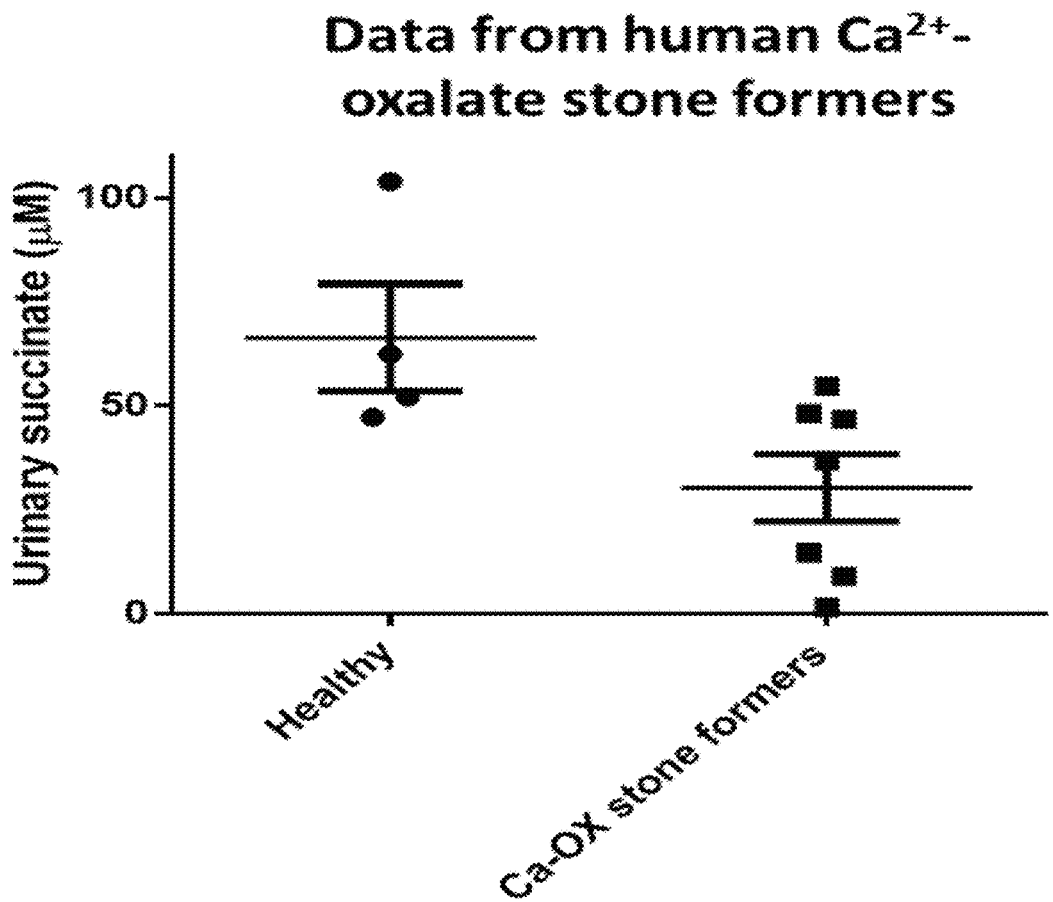

Example 6: Slc26a6 Regulates Renal Succinate Reabsorption, Renin Secretion and Blood Pressure The physical and functional interaction between NaDC-1 and slc26a6, in which slc26a6 inhibits NaDC-1, raised the possibility that slc26a6 affects not only vectorial citrate, but also vectorial succinate transport in the proximal tubule. To test this prediction, urine samples were collected for 24 h from WT and slc26a6$^{-/-}$ mice and the levels of succinate in the urine were measured. FIG. 7A shows reduced urinary succinate concentrations in slc26a6$^{-/-}$ mice, as compared with control mice, while urinary creatinine levels were not different between the two groups (FIG. 7B). The results presented in FIGS. 7A-E indicate that hypocitraturia is accompanied by "hyposuccinaturia". Notably, as indicated in FIG. 7C, serum succinate levels are ~35% higher in slc26a6$^{-/-}$ mice, suggesting elevated absorption of succinate from the urine. High succinate absorption to the serum can ultimately increase stimulation of the succinate receptor SUCNR1 in endothelial cells of the afferent arteriole, which, in turn, would lead to elevated renin secretion by granular cells at the juxtaglomerular apparatus. To test this scenario, plasma renin concentration was measured, and ~30% increase in plasma renin was found in slc26a6$^{-/-}$ mice (FIG. 7D). To test the effect of high serum succinate on renal SUCNR1-IRBIT signaling axis, SUCNR1 and IRBIT expression was monitored in kidney lysates which were obtained from WT, slc26a6$^{-/-}$ mice and WT mice injected (IV) with succinate (10 mg/Kg body weight). SUCNR1 expression was not significantly different between the groups (FIG. 7E). IRBIT expression in renal lysates of slc26a6$^{-/-}$ mice was similar to the expression in lysates of WT mice (FIG. 7F-G). Nevertheless, a small (~10%) but statistically significant decrease in the renal IRBIT expression of WT mice injected with succinate was observed. This may be a result of the acute increase in succinate which is compensated for during chronic succinate increase as occurs in slc26a6$^{-/-}$ mice. Interestingly, patients that form Ca2+-oxalate kidney stones also had significantly reduced urinary succinate levels as compared to healthy controls (FIG. 7H). Volunteers were recruited at the Soroka University Medical Center, Beer-Sheva, Israel for an ongoing pilot clinical study, which has been approved by the institutional Helsinki Committee. Importantly, 42% of the Ca2+-oxalate stone formers were also diagnosed with hypertension.

Figure 7I:
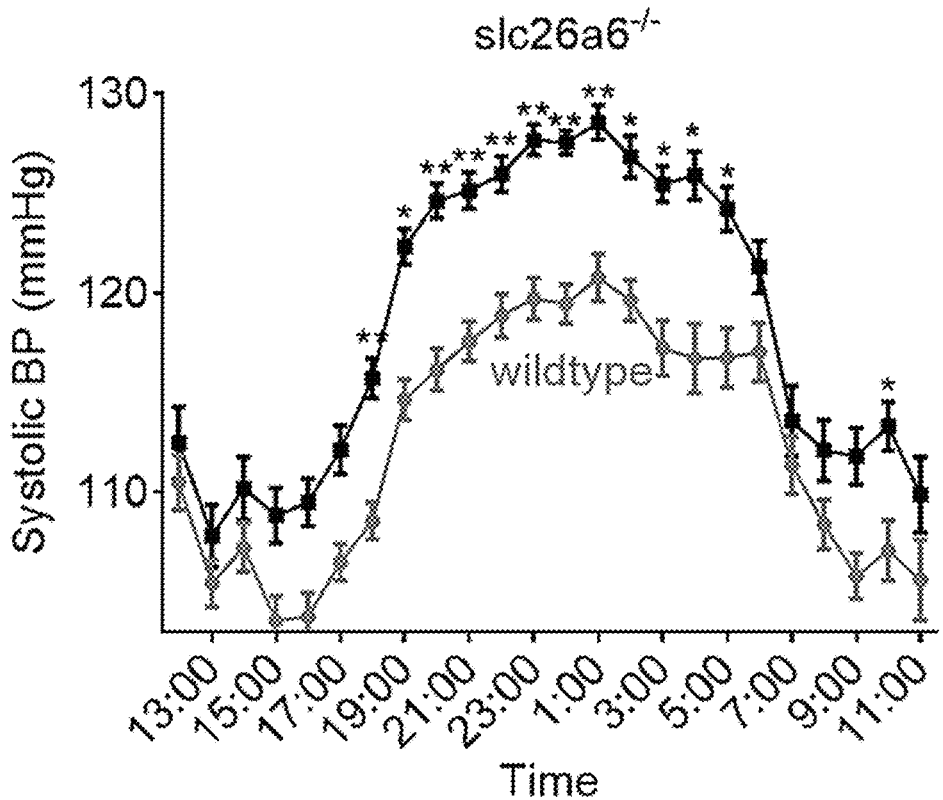

The increased serum succinate appeared to affect blood pressure. A 24 h telemetric blood pressure measurement indicated that slc26a6$^{-/-}$ mice are hypertensive, specifically during the nocturnal awake/active phase hours (FIG. 7I). Further analysis indicated that the slc26a6$^{-/-}$ mice hypertension is not additive with the effect of dietary salt intake.

Figure 7J:
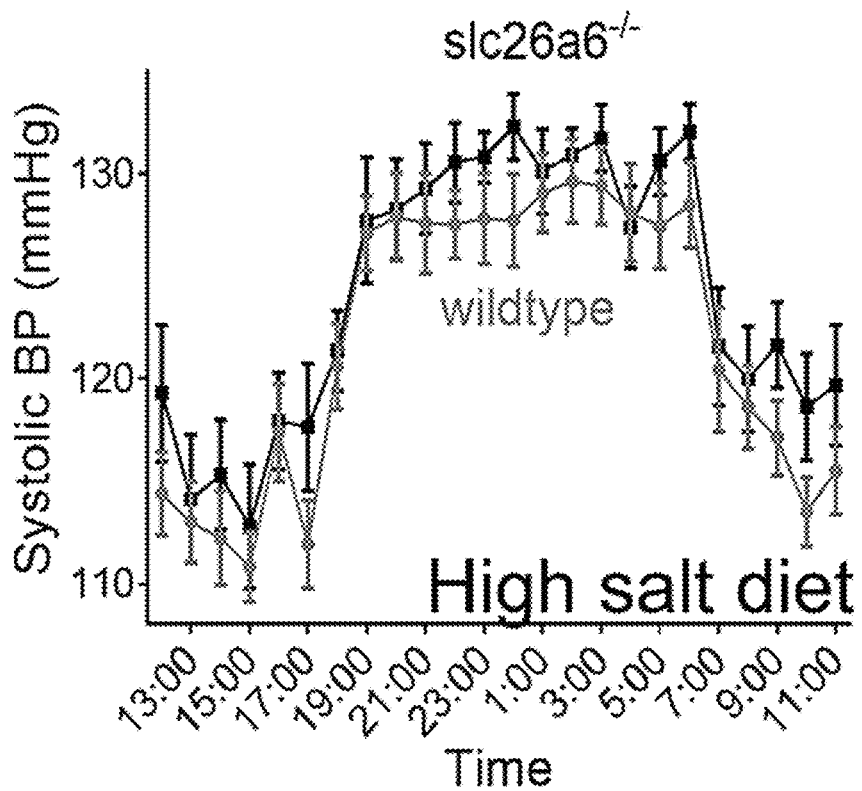
Figure 7K:
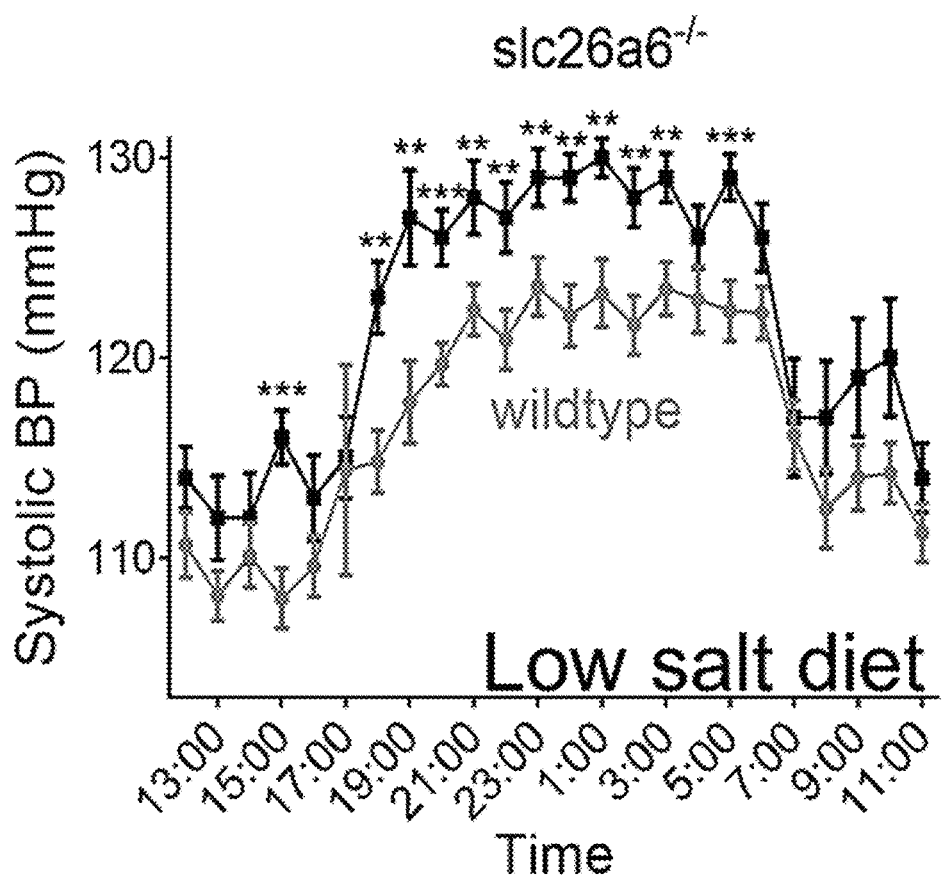
Figure 7L:
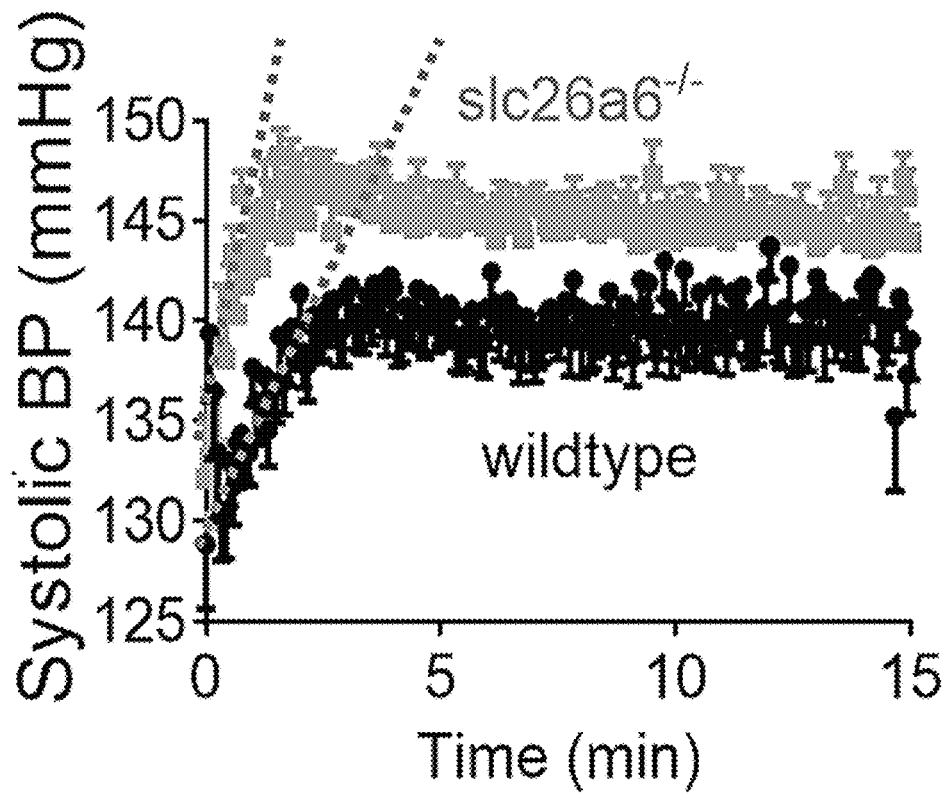
Figure 7L:
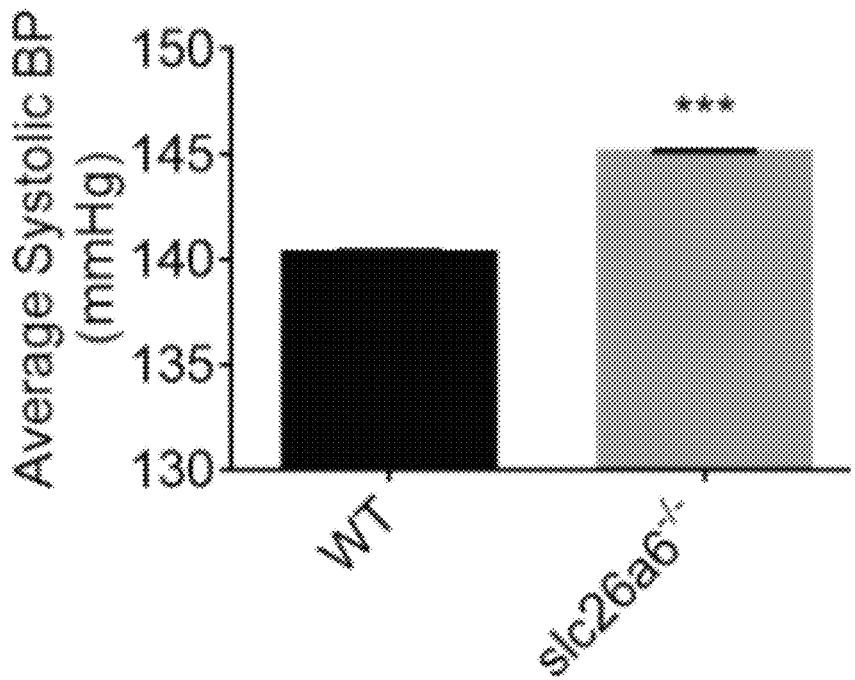
Figure 7M:
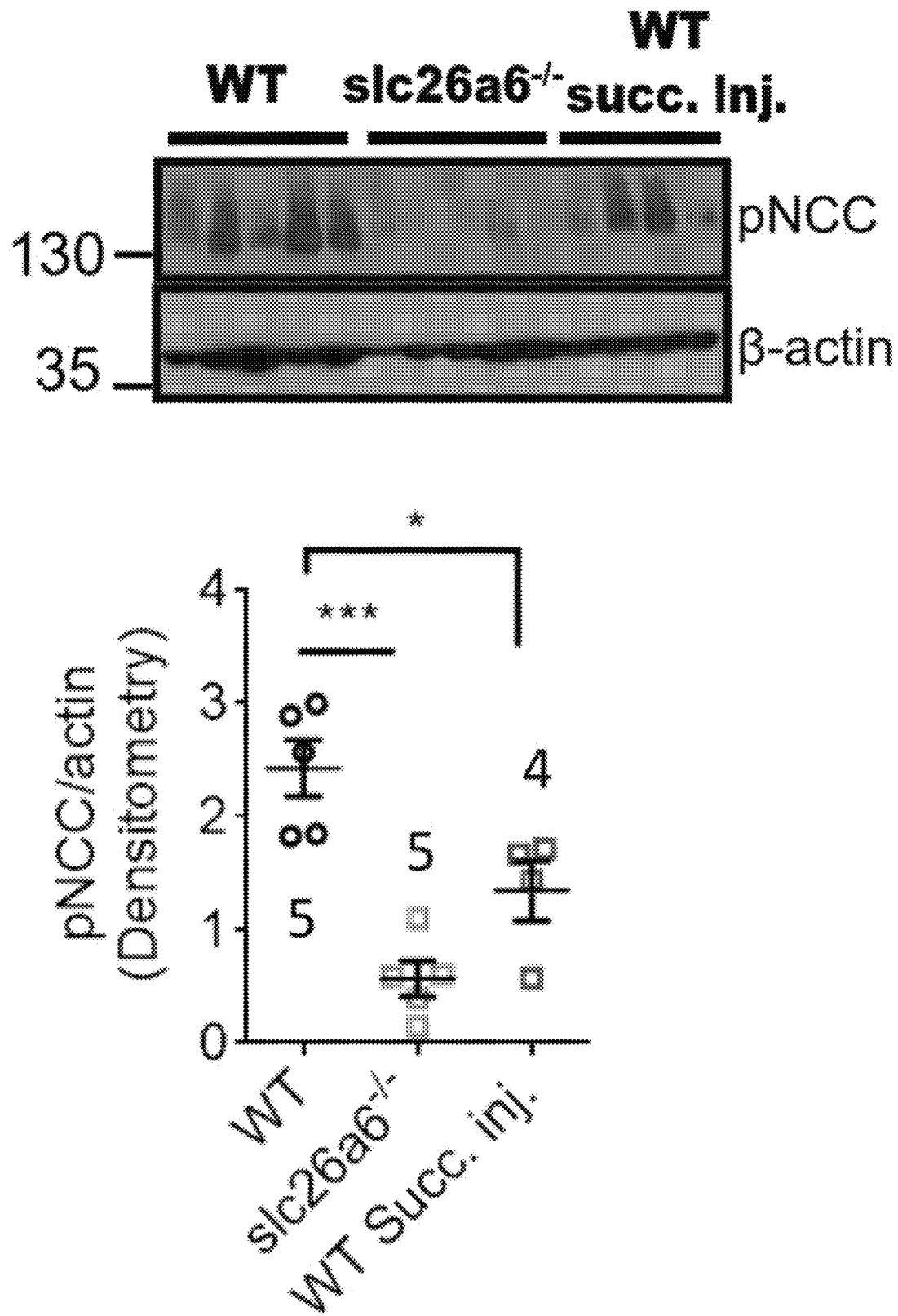

Thus, when mice were acclimated to high salt diet the difference in blood pressure between WT and slc26a6$^{-/-}$ mice disappeared (FIG. 7J) and the slc26a6$^{-/-}$ mice higher blood pressure was maintained when mice were fed low salt diet (FIG. 7K). To investigate the role of slc26a6 deletion and physical activity on blood pressure, the acute increase in blood pressure in response to exercise was assayed. Systolic blood pressure increased faster and to a higher level in the slc26a6$^{-/-}$ mice (FIG. 7L). Regulation of salt and water absorption by the Renin-angiotensin system is a major mechanism of blood pressure control. Specifically, the expression and function of Na$^+$:Cl$^-$ transporters NCC is modulated via phosphorylation. The effect of succinate-mediated hypertension on salt retention was investigated by monitoring the expression of Thr$^{53}$ phosphorylated NCC cotransporter (pNCC) and reporting the active form of the transporter. Interestingly, lower expression of pNCC is observed in both slc26a6$^{-/-}$ mice and WT mice injected (IV) with succinate 10 mg/kg body weight compared to WT controls (FIG. 7M). These findings may explain the salt independency of hypertension in the slc26a6$^{-/-}$ mice.

Example 7: Recombinant hSUCNR1

Figure 8A:
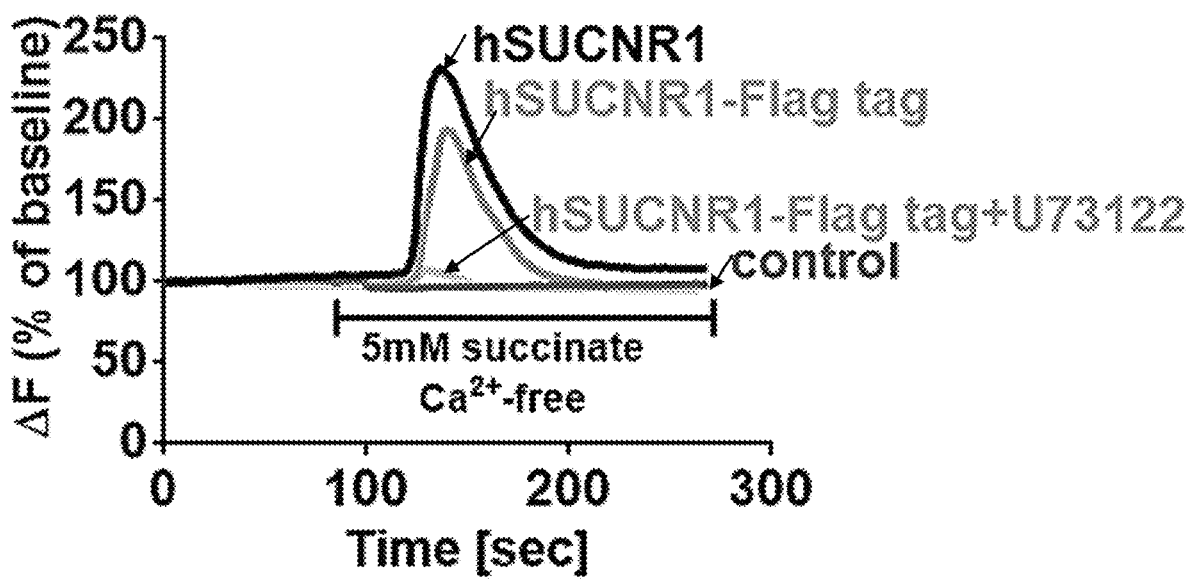
FIGS. 8A-C: (8A-B) Line graphs showing (8A) the amount of free calcium as a percentage of the baseline amount present in HEK293T culture immediately after addition of succinate and (8B) over 25 minutes after addition. (8C) Photograph of a western blot of FLAG-tag purified recombinant hSUCNR1.

Non-tagged human SUCNR1 (hSUCNR1, SEQ ID NO: 2) in the pcMV6-XL5 vector and C-terminal (K)DYK Flag-tagged human SUCNR1 in a pcDNA3.1+ expression vector were utilized. To test that the expression vectors, with and without Flag, produced functional SUCNR1, both vectors were transiently transfected into HEK293T cells in culture, along with empty vector as a control. As binding of succinate to its receptor and subsequent receptor stimulation are known to result in intracellular calcium (Ca2+) release from the endoplasmic reticulum, changes in intracellular Ca2+ were monitored 24 hours after transfection. The baseline calcium level was determined, and the cells were then perfused with a calcium free solution containing 5 mM succinate. In cells transfected with hSUCNR1 or hSUCNR1-Flag, the addition of succinate resulted in a large spike in free Ca2+, which was not seen in cells that received the empty vector (FIG. 8A). Further, when the phospholipase C (PLC) inhibitor U73122 was added to the perfusion solution, the calcium spike did not occur, indicating that the recombinant protein is functioning in a manner consistent with wild-type protein.

Figure 8B:
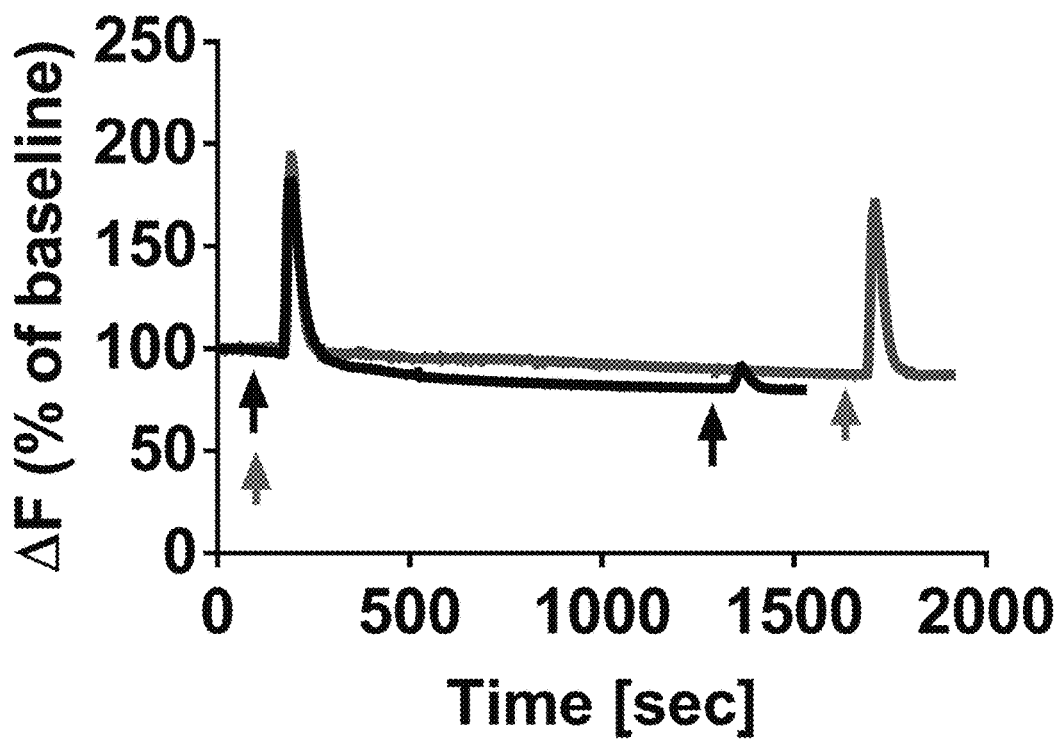
Figure 8C:
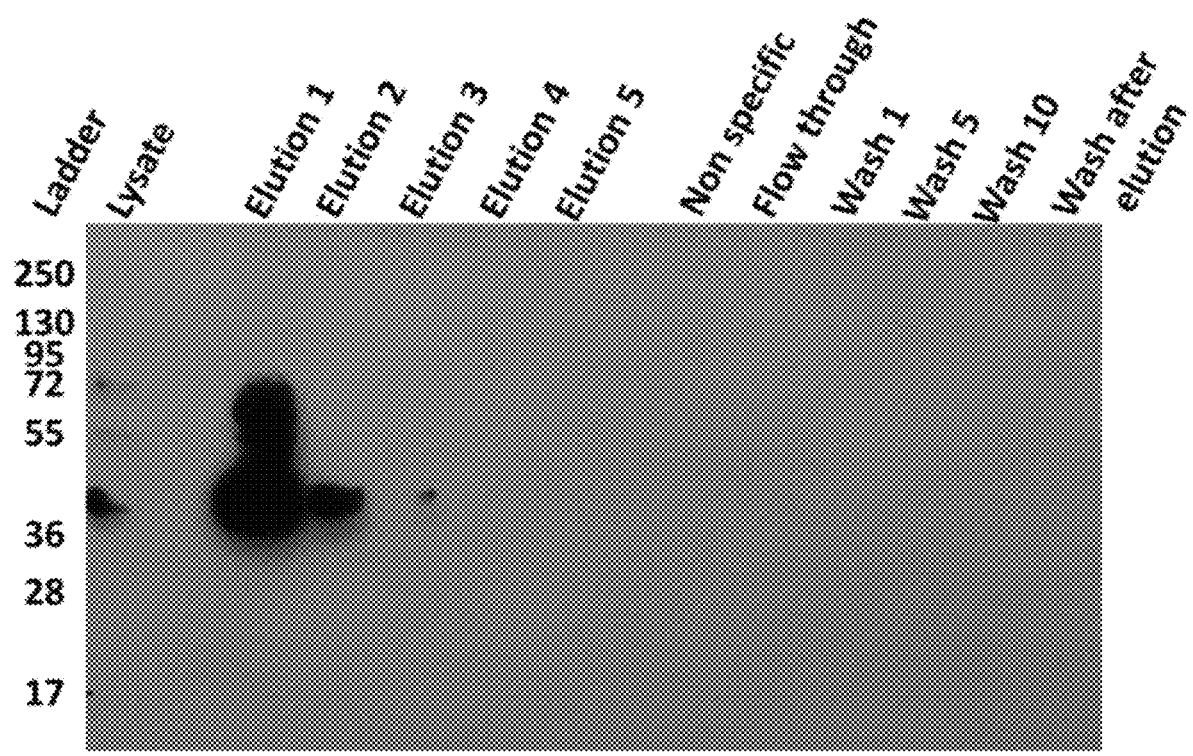

It was also found that the recombinant Flag-tagged hSUCNR1 was desensitized to further stimulation by exposure to succinate (FIG. 8B), just as wild-type receptor is. These data suggest that the cloned hSUCNR1 produces functional protein and the Flag tag interferes with neither succinate binding, downstream signaling nor receptor sensitization. As such a Flag-tag does not alter protein function and can be used for protein purification (FIG. 8C).

Example 8: Design of Super Succinate-Binding Proteins (Succilators)

Proteins capable of strongly binding free succinate are designed. The proteins also have enhanced stability in solution allowing them to be used as succinate chelators (succilators). The succinate-receptor complex may also be more stable. The human receptor hSUCNR1, which exclusively binds succinate, is modified to generate a protein that is more stable in the physiological milieu of the gut, has a higher affinity for succinate, and also is more stable in complex with succinate than wild-type hSUCNR1. In silico analysis of SUCNR1 is performed to map specific regions of the protein that determine protein and complex stability and succinate binding affinity.

The succinate binding pocket is examined for mutations that increase binding to succinate. Specifically, the essential positively charged amino acids arginine 99 (R99), arginine 281 (R281), arginine 252 (R252) and histidine 103 (H103) are examined for substitutions that increase either binding to succinate, stability of the protein, stability of the complex or a combination of these. Further, other amino acids that are known to have counterparts that effect stability of G-protein coupled receptors (GPCRs), such as leucine 191, threonine 192, glycine 195, isoleucine 110, phenylalanine 241, methionine 203, valine 238, tyrosine 207, arginine 120, phenylalanine 285, asparagine 287 and tyrosine 295 (L191, T192, G195, I110, F241, M203, V238, Y207, R120, R281, F285, N287, Y295) are investigated. Mutants are generated (targeted mutation of the DNA sequence encoding for the protein), purified by affinity chromatography, and screened for increased binding and stability. The best mutants are then tested in culture for chelation of free succinate.

Example 9: Treatment of IBD In Vitro

The hSUCNR1 mutants are tested in a tissue culture models of colitis. Human enteroid and macrophage co-cultures or colon epithelial cell cultures are used as a model system to test the effects of succilators in providing protection against epithelial damage and pro-inflammatory process. In vitro fecal mimicking or physiological solution environments are employed to test enhanced stability of the protein and/or complex.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

The invention claimed is:

1. A method of treating or preventing a succinate-associated disease or condition in a subject in need thereof, the method comprising administering to said subject a therapeutically effective amount of a first polypeptide which decreases serum succinate levels in said subject, wherein said succinate-associated disease or condition is selected from inflammatory bowel disease (IBD), urolithiasis, rheumatoid arthritis, cardiac hypertrophy, inflammation, kidney stones and hypertension, thereby treating or preventing a succinate-associated disease or condition.

2. The method of claim 1, wherein said IBD is selected from any one of: colitis, ulcerative colitis, Crohn's disease, and Bechet's disease.

3. The method of claim 1, wherein said first polypeptide is a succinate receptor 1 (SUCNR1) comprising the amino acid sequence set forth in SEQ ID NO: 7, or an analog thereof having at least 80% homology thereto, which binds succinate.

4. The method of claim 3, wherein said analog comprises a least one amino acid substitution in the amino acid sequence set forth in SEQ ID NO: 7, which increases binding of the polypeptide to succinate, increases the stability of the polypeptide in solution, increases stability of the receptor-succinate complex, or any combination thereof.

5. The method of claim 3, wherein said analog comprises at least one amino acid substitution at a position selected form the group consisting of: 99, 103, 252, and 281, of SEQ ID NO: 7.

6. The method of claim 1, further comprising administering to said subject a therapeutically effective amount of at least a second polypeptide comprising an amino acid sequence of:
 a. a Slc26a6 STAS domain comprising the amino acid sequence set forth in SEQ ID NO: 1 or 2, or an analog thereof having at least 80% homology thereto, which binds solute carrier family 13 member 2 (NaDC-1), and comprises glutamic acid 613 of SEQ ID NO: 1 or aspartic acid 637 of SEQ ID NO: 2; or
 b. IRBIT comprising the amino acid sequence set forth in SEQ ID NO: 3 or 4 or an analog thereof having at least 80% homology thereto, which binds NaDC-1,
thereby decreasing NaDC-1 transport of succinate.

7. The method of claim 6, wherein said NaDC-1 comprises the amino acid sequence provided in SEQ ID NO: 5 or SEQ ID NO: 6 and at least one mutation which increases binding to lysine 107, arginine 108, or both of SEQ ID NO: 5 or lysine 156, arginine 157, or both of SEQ ID NO: 6.

8. The method of claim 6, wherein said decreasing NaDC-1 transport of succinate comprises increasing binding of NaDC-1 to solute carrier family 26 member 6 (Slc26a6), IP3 receptor-binding protein released with IP3 (IRBIT), or both.

9. The method of claim 8, wherein said increasing binding to Slc26a6 comprises increasing electrostatic interaction between a STAS domain of Slc26a6 and a H4c domain of NaDC-1.

10. A method of increasing succinate reabsorption from urine in a subject in need thereof, the method comprising mutating at least one of amino acids: (a) E613 of SEQ ID NO: 1 and D637 of SEQ ID NO: 2 of Slc26a6, (b) K107 of SEQ ID NO: 5, R108 of SEQ ID NO: 5, K156 of SEQ ID NO: 6, and R157 of SEQ ID NO: 6 of NaDC-1, or both, in said subject,
thereby increasing succinate reabsorption in a subject in need thereof.

11. The method of claim 10, wherein said mutating: (a) E613 of SEQ ID NO: 1 and D637 of SEQ ID NO: 2 of Slc26a6 inhibits electrostatic interaction between the STAS domain of Slc26a6 and the H4c domain of NaDC-1 in said subject, (b) K107 of SEQ ID NO: 5, R108 of SEQ ID NO: 5, K156 of SEQ ID NO: 6, and R157 of SEQ ID NO: 6 of NaDC-1 inhibits interaction between NaDC-1 and IRBIT in said subject; or a combination of (a) and (b).

* * * * *

SEQUENCE LISTING

```
<160> NUMBER OF SEQ ID NOS: 23

<210> SEQ ID NO 1
<211> LENGTH: 735
<212> TYPE: PRT
<213> ORGANISM: Mus musculus

<400> SEQUENCE: 1

Met Glu Leu Gln Arg Arg Asp Tyr His Val Glu Arg Pro Leu Leu Asn
1               5                   10                  15
```

```
Gln Glu Gln Leu Glu Asp Leu Gly His Trp Gly Pro Ala Ala Lys Thr
         20                  25                  30

His Gln Trp Arg Thr Trp Phe Arg Cys Ser Arg Ala Arg Ala His Ser
         35                  40                  45

Leu Leu Leu Gln His Val Pro Val Leu Gly Trp Leu Pro Arg Tyr Pro
 50                  55                  60

Val Arg Glu Trp Leu Leu Gly Asp Leu Leu Ser Gly Leu Ser Val Ala
 65                  70                  75                  80

Ile Met Gln Leu Pro Gln Gly Leu Ala Tyr Ala Leu Leu Ala Gly Leu
                 85                  90                  95

Pro Pro Met Phe Gly Leu Tyr Ser Ser Phe Tyr Pro Val Phe Ile Tyr
                100                 105                 110

Phe Leu Phe Gly Thr Ser Arg His Ile Ser Val Gly Thr Phe Ala Val
             115                 120                 125

Met Ser Val Met Val Gly Ser Val Thr Glu Ser Leu Thr Ala Asp Lys
130                 135                 140

Ala Phe Val Gln Gly Leu Asn Ala Thr Ala Asp Asp Ala Arg Val Gln
145                 150                 155                 160

Val Ala Tyr Thr Leu Ser Phe Leu Val Gly Leu Phe Gln Val Gly Leu
                165                 170                 175

Gly Leu Val His Phe Gly Phe Val Val Thr Tyr Leu Ser Glu Pro Leu
                180                 185                 190

Val Arg Ser Tyr Thr Thr Ala Ala Ser Val Gln Val Leu Val Ser Gln
             195                 200                 205

Leu Lys Tyr Val Phe Gly Ile Lys Leu Ser Ser His Ser Gly Pro Leu
         210                 215                 220

Ser Val Ile Tyr Thr Val Leu Glu Val Cys Ala Gln Leu Pro Glu Thr
225                 230                 235                 240

Val Pro Gly Thr Val Val Thr Ala Ile Val Ala Gly Val Ala Leu Val
                245                 250                 255

Leu Val Lys Leu Leu Asn Glu Lys Leu His Arg Arg Leu Pro Leu Pro
             260                 265                 270

Ile Pro Gly Glu Leu Leu Thr Leu Ile Gly Ala Thr Gly Ile Ser Tyr
         275                 280                 285

Gly Val Lys Leu Asn Asp Arg Phe Lys Val Asp Val Val Gly Asn Ile
         290                 295                 300

Thr Thr Gly Leu Ile Pro Pro Val Ala Pro Lys Thr Glu Leu Phe Ala
305                 310                 315                 320

Thr Leu Val Gly Asn Ala Phe Ala Ile Ala Val Val Gly Phe Ala Ile
                325                 330                 335

Ala Ile Ser Leu Gly Lys Ile Phe Ala Leu Arg His Gly Tyr Arg Val
             340                 345                 350

Asp Ser Asn Gln Glu Leu Val Ala Leu Gly Leu Ser Asn Leu Ile Gly
         355                 360                 365

Gly Phe Phe Gln Cys Phe Pro Val Ser Cys Ser Met Ser Arg Ser Leu
         370                 375                 380

Val Gln Glu Ser Thr Gly Gly Asn Thr Gln Val Ala Gly Ala Val Ser
385                 390                 395                 400

Ser Leu Phe Ile Leu Leu Ile Ile Val Lys Leu Gly Glu Leu Phe Arg
                405                 410                 415

Asp Leu Pro Lys Ala Val Leu Ala Ala Val Ile Ile Val Asn Leu Lys
             420                 425                 430
```

```
Gly Met Met Lys Gln Phe Ser Asp Ile Cys Ser Leu Trp Lys Ala Asn
            435                 440                 445

Arg Val Asp Leu Leu Ile Trp Leu Val Thr Phe Val Ala Thr Ile Leu
450                 455                 460

Leu Asn Leu Asp Ile Gly Leu Ala Val Ser Ile Val Phe Ser Leu Leu
465                 470                 475                 480

Leu Val Val Val Arg Met Gln Leu Pro His Tyr Ser Val Leu Gly Gln
                485                 490                 495

Val Pro Asp Thr Asp Ile Tyr Arg Asp Val Ala Glu Tyr Ser Gly Ala
                500                 505                 510

Lys Glu Val Pro Gly Val Lys Val Phe Arg Ser Ser Ala Thr Leu Tyr
            515                 520                 525

Phe Ala Asn Ala Glu Leu Tyr Ser Asp Ser Leu Lys Glu Lys Cys Gly
            530                 535                 540

Val Asp Val Asp Arg Leu Ile Thr Gln Lys Lys Arg Ile Lys Lys
545                 550                 555                 560

Gln Glu Met Lys Leu Lys Arg Met Lys Lys Ala Lys Lys Ser Gln Lys
                565                 570                 575

Gln Asp Ala Ser Ser Lys Ile Ser Ser Val Ser Val Asn Val Asn Thr
            580                 585                 590

Asn Leu Glu Asp Val Lys Ser Asn Asp Val Glu Gly Ser Glu Ala Lys
            595                 600                 605

Val His Gln Gly Glu Glu Leu Gln Asp Val Val Ser Ser Asn Gln Glu
            610                 615                 620

Asp Ala Lys Ala Pro Thr Met Thr Ser Leu Lys Ser Leu Gly Leu Pro
625                 630                 635                 640

Gln Pro Gly Phe His Ser Leu Ile Leu Asp Leu Ser Thr Leu Ser Phe
                645                 650                 655

Val Asp Thr Val Cys Ile Lys Ser Leu Lys Asn Ile Phe Arg Asp Phe
                660                 665                 670

Arg Glu Ile Glu Val Glu Val Tyr Ile Ala Ala Cys Tyr Ser Pro Val
            675                 680                 685

Val Ala Gln Leu Glu Ala Gly His Phe Phe Asp Glu Ser Ile Thr Lys
            690                 695                 700

Gln His Val Phe Ala Ser Val His Asp Ala Val Thr Phe Ala Leu Ser
705                 710                 715                 720

His Arg Lys Ser Val Pro Lys Ser Pro Val Leu Ala Thr Lys Leu
                725                 730                 735

<210> SEQ ID NO 2
<211> LENGTH: 759
<212> TYPE: PRT
<213> ORGANISM: Homo sapiens

<400> SEQUENCE: 2

Met Gly Leu Ala Asp Ala Ser Gly Pro Arg Asp Thr Gln Ala Leu Leu
1               5                   10                  15

Ser Ala Thr Gln Ala Met Asp Leu Arg Arg Arg Asp Tyr His Met Glu
                20                  25                  30

Arg Pro Leu Leu Asn Gln Glu His Leu Glu Glu Leu Gly Arg Trp Gly
            35                  40                  45

Ser Ala Pro Arg Thr His Gln Trp Arg Thr Trp Leu Gln Cys Ser Arg
        50                  55                  60

Ala Arg Ala Tyr Ala Leu Leu Leu Gln His Leu Pro Val Leu Val Trp
65                  70                  75                  80
```

```
Leu Pro Arg Tyr Pro Val Arg Asp Trp Leu Gly Asp Leu Leu Ser
                85                  90                  95
Gly Leu Ser Val Ala Ile Met Gln Leu Pro Gln Gly Leu Ala Tyr Ala
            100                 105                 110
Leu Leu Ala Gly Leu Pro Pro Val Phe Gly Leu Tyr Ser Ser Phe Tyr
            115                 120                 125
Pro Val Phe Ile Tyr Phe Leu Phe Gly Thr Ser Arg His Ile Ser Val
130                 135                 140
Gly Thr Phe Ala Val Met Ser Val Met Val Gly Ser Val Thr Glu Ser
145                 150                 155                 160
Leu Ala Pro Gln Ala Leu Asn Asp Ser Met Ile Asn Glu Thr Ala Arg
                165                 170                 175
Asp Ala Ala Arg Val Gln Val Ala Ser Thr Leu Ser Val Leu Val Gly
                180                 185                 190
Leu Phe Gln Val Gly Leu Gly Leu Ile His Phe Gly Phe Val Val Thr
            195                 200                 205
Tyr Leu Ser Glu Pro Leu Val Arg Gly Tyr Thr Thr Ala Ala Ala Val
        210                 215                 220
Gln Val Phe Val Ser Gln Leu Lys Tyr Val Phe Gly Leu His Leu Ser
225                 230                 235                 240
Ser His Ser Gly Pro Leu Ser Leu Ile Tyr Thr Val Leu Glu Val Cys
                245                 250                 255
Trp Lys Leu Pro Gln Ser Lys Val Gly Thr Val Thr Ala Ala Val
                260                 265                 270
Ala Gly Val Val Leu Val Val Lys Leu Leu Asn Asp Lys Leu Gln
            275                 280                 285
Gln Gln Leu Pro Met Pro Ile Pro Gly Glu Leu Leu Thr Leu Ile Gly
        290                 295                 300
Ala Thr Gly Ile Ser Tyr Gly Met Gly Leu Lys His Arg Phe Glu Val
305                 310                 315                 320
Asp Val Val Gly Asn Ile Pro Ala Gly Leu Val Pro Pro Val Ala Pro
                325                 330                 335
Asn Thr Gln Leu Phe Ser Lys Leu Val Gly Ser Ala Phe Thr Ile Ala
            340                 345                 350
Val Val Gly Phe Ala Ile Ala Ile Ser Leu Gly Lys Ile Phe Ala Leu
            355                 360                 365
Arg His Gly Tyr Arg Val Asp Ser Asn Gln Glu Leu Val Ala Leu Gly
        370                 375                 380
Leu Ser Asn Leu Ile Gly Gly Ile Phe Gln Cys Phe Pro Val Ser Cys
385                 390                 395                 400
Ser Met Ser Arg Ser Leu Val Gln Glu Ser Thr Gly Gly Asn Ser Gln
                405                 410                 415
Val Ala Gly Ala Ile Ser Ser Leu Phe Ile Leu Leu Ile Ile Val Lys
            420                 425                 430
Leu Gly Glu Leu Phe His Asp Leu Pro Lys Ala Val Leu Ala Ala Ile
            435                 440                 445
Ile Ile Val Asn Leu Lys Gly Met Leu Arg Gln Leu Ser Asp Met Arg
450                 455                 460
Ser Leu Trp Lys Ala Asn Arg Ala Asp Leu Leu Ile Trp Leu Val Thr
465                 470                 475                 480
Phe Thr Ala Thr Ile Leu Leu Asn Leu Asp Leu Gly Leu Val Val Ala
                485                 490                 495
```

```
Val Ile Phe Ser Leu Leu Val Val Arg Thr Gln Met Pro His
            500                 505                 510

Tyr Ser Val Leu Gly Gln Val Pro Asp Thr Asp Ile Tyr Arg Asp Val
    515                 520                 525

Ala Glu Tyr Ser Glu Ala Lys Glu Val Arg Gly Val Lys Val Phe Arg
        530                 535                 540

Ser Ser Ala Thr Val Tyr Phe Ala Asn Ala Glu Phe Tyr Ser Asp Ala
545                 550                 555                 560

Leu Lys Gln Arg Cys Gly Val Asp Val Asp Phe Leu Ile Ser Gln Lys
                565                 570                 575

Lys Lys Leu Leu Lys Lys Gln Glu Gln Leu Lys Leu Lys Gln Leu Gln
            580                 585                 590

Lys Glu Glu Lys Leu Arg Lys Gln Ala Ala Ser Pro Lys Gly Ala Ser
        595                 600                 605

Val Ser Ile Asn Val Asn Thr Ser Leu Glu Asp Met Arg Ser Asn Asn
    610                 615                 620

Val Glu Asp Cys Lys Met Met Gln Val Ser Ser Gly Asp Lys Met Glu
625                 630                 635                 640

Asp Ala Thr Ala Asn Gly Gln Glu Asp Ser Lys Ala Pro Asp Gly Ser
                645                 650                 655

Thr Leu Lys Ala Leu Gly Leu Pro Gln Pro Asp Phe His Ser Leu Ile
            660                 665                 670

Leu Asp Leu Gly Ala Leu Ser Phe Val Asp Thr Val Cys Leu Lys Ser
        675                 680                 685

Leu Lys Asn Ile Phe His Asp Phe Arg Glu Ile Glu Val Glu Val Tyr
    690                 695                 700

Met Ala Ala Cys His Ser Pro Val Val Ser Gln Leu Glu Ala Gly His
705                 710                 715                 720

Phe Phe Asp Ala Ser Ile Thr Lys Lys His Leu Phe Ala Ser Val His
                725                 730                 735

Asp Ala Val Thr Phe Ala Leu Gln His Pro Arg Pro Val Pro Asp Ser
            740                 745                 750

Pro Val Ser Val Thr Arg Leu
            755

<210> SEQ ID NO 3
<211> LENGTH: 530
<212> TYPE: PRT
<213> ORGANISM: Mus musculus

<400> SEQUENCE: 3

Met Ser Met Pro Asp Ala Met Pro Leu Pro Gly Val Gly Glu Glu Leu
1               5                   10                  15

Lys Gln Ala Lys Glu Ile Glu Asp Ala Glu Lys Tyr Ser Phe Met Ala
            20                  25                  30

Thr Val Thr Lys Ala Pro Lys Lys Gln Ile Gln Phe Ala Asp Asp Met
        35                  40                  45

Gln Glu Phe Thr Lys Phe Pro Thr Lys Thr Gly Arg Arg Ser Leu Ser
    50                  55                  60

Arg Ser Ile Ser Gln Ser Ser Thr Asp Ser Tyr Ser Ser Ala Ala Ser
65                  70                  75                  80

Tyr Thr Asp Ser Ser Asp Asp Glu Val Ser Pro Arg Glu Lys Gln Gln
                85                  90                  95

Thr Asn Ser Lys Gly Ser Ser Asn Phe Cys Val Lys Asn Ile Lys Gln
            100                 105                 110
```

```
Ala Glu Phe Gly Arg Arg Glu Ile Glu Ile Ala Glu Gln Asp Met Ser
            115                 120                 125

Ala Leu Ile Ser Leu Arg Lys Arg Ala Gln Gly Glu Lys Pro Leu Ala
    130                 135                 140

Gly Ala Lys Ile Val Gly Cys Thr His Ile Thr Ala Gln Thr Ala Val
145                 150                 155                 160

Leu Ile Glu Thr Leu Cys Ala Leu Gly Ala Gln Cys Arg Trp Ser Ala
                165                 170                 175

Cys Asn Ile Tyr Ser Thr Gln Asn Glu Val Ala Ala Leu Ala Glu
            180                 185                 190

Ala Gly Val Ala Val Phe Ala Trp Lys Gly Glu Ser Glu Asp Asp Phe
        195                 200                 205

Trp Trp Cys Ile Asp Arg Cys Val Asn Met Asp Gly Trp Gln Ala Asn
    210                 215                 220

Met Ile Leu Asp Asp Gly Gly Asp Leu Thr His Trp Val Tyr Lys Lys
225                 230                 235                 240

Tyr Pro Asn Val Phe Lys Lys Ile Arg Gly Ile Val Glu Glu Ser Val
                245                 250                 255

Thr Gly Val His Arg Leu Tyr Gln Leu Ser Lys Ala Gly Lys Leu Cys
            260                 265                 270

Val Pro Ala Met Asn Val Asn Asp Ser Val Thr Lys Gln Lys Phe Asp
        275                 280                 285

Asn Leu Tyr Cys Cys Arg Glu Ser Ile Leu Asp Gly Leu Lys Arg Thr
    290                 295                 300

Thr Asp Val Met Phe Gly Gly Lys Gln Val Val Cys Gly Tyr Gly
305                 310                 315                 320

Glu Val Gly Lys Gly Cys Cys Ala Ala Leu Lys Ala Leu Gly Ala Ile
                325                 330                 335

Val Tyr Ile Thr Glu Ile Asp Pro Ile Cys Ala Leu Gln Ala Cys Met
            340                 345                 350

Asp Gly Phe Arg Val Val Lys Leu Asn Glu Val Ile Arg Gln Val Asp
        355                 360                 365

Val Val Ile Thr Cys Thr Gly Asn Lys Asn Val Val Thr Arg Glu His
    370                 375                 380

Leu Asp Arg Met Lys Asn Ser Cys Ile Val Cys Asn Met Gly His Ser
385                 390                 395                 400

Asn Thr Glu Ile Asp Val Thr Ser Leu Arg Thr Pro Glu Leu Thr Trp
                405                 410                 415

Glu Arg Val Arg Ser Gln Val Asp His Val Ile Trp Pro Asp Gly Lys
            420                 425                 430

Arg Val Val Leu Leu Ala Glu Gly Arg Leu Leu Asn Leu Ser Cys Ser
        435                 440                 445

Thr Val Pro Thr Phe Val Leu Ser Ile Thr Ala Thr Thr Gln Ala Leu
    450                 455                 460

Ala Leu Ile Glu Leu Tyr Asn Ala Pro Glu Gly Arg Tyr Lys Gln Asp
465                 470                 475                 480

Val Tyr Leu Leu Pro Lys Lys Met Asp Glu Tyr Val Ala Ser Leu His
                485                 490                 495

Leu Pro Ser Phe Asp Ala His Leu Thr Glu Leu Thr Asp Asp Gln Ala
            500                 505                 510

Lys Tyr Leu Gly Leu Asn Lys Asn Gly Pro Phe Lys Pro Asn Tyr Tyr
        515                 520                 525
```

Arg Tyr
    530

<210> SEQ ID NO 4
<211> LENGTH: 530
<212> TYPE: PRT
<213> ORGANISM: Homo sapiens

<400> SEQUENCE: 4

Met Ser Met Pro Asp Ala Met Pro Leu Pro Gly Val Gly Glu Leu
1               5                   10                  15

Lys Gln Ala Lys Glu Ile Glu Asp Ala Glu Lys Tyr Ser Phe Met Ala
                20                  25                  30

Thr Val Thr Lys Ala Pro Lys Lys Gln Ile Gln Phe Ala Asp Asp Met
            35                  40                  45

Gln Glu Phe Thr Lys Phe Pro Thr Lys Thr Gly Arg Arg Ser Leu Ser
    50                  55                  60

Arg Ser Ile Ser Gln Ser Ser Thr Asp Ser Tyr Ser Ser Ala Ala Ser
65                  70                  75                  80

Tyr Thr Asp Ser Ser Asp Asp Glu Val Ser Pro Arg Glu Lys Gln Gln
                85                  90                  95

Thr Asn Ser Lys Gly Ser Ser Asn Phe Cys Val Lys Asn Ile Lys Gln
            100                 105                 110

Ala Glu Phe Gly Arg Arg Glu Ile Glu Ile Ala Glu Gln Asp Met Ser
        115                 120                 125

Ala Leu Ile Ser Leu Arg Lys Arg Ala Gln Gly Glu Lys Pro Leu Ala
130                 135                 140

Gly Ala Lys Ile Val Gly Cys Thr His Ile Thr Ala Gln Thr Ala Val
145                 150                 155                 160

Leu Ile Glu Thr Leu Cys Ala Leu Gly Ala Gln Cys Arg Trp Ser Ala
                165                 170                 175

Cys Asn Ile Tyr Ser Thr Gln Asn Glu Val Ala Ala Ala Leu Ala Glu
            180                 185                 190

Ala Gly Val Ala Val Phe Ala Trp Lys Gly Glu Ser Glu Asp Asp Phe
        195                 200                 205

Trp Trp Cys Ile Asp Arg Cys Val Asn Met Asp Gly Trp Gln Ala Asn
210                 215                 220

Met Ile Leu Asp Asp Gly Gly Asp Leu Thr His Trp Val Tyr Lys Lys
225                 230                 235                 240

Tyr Pro Asn Val Phe Lys Lys Ile Arg Gly Ile Val Glu Glu Ser Val
                245                 250                 255

Thr Gly Val His Arg Leu Tyr Gln Leu Ser Lys Ala Gly Lys Leu Cys
            260                 265                 270

Val Pro Ala Met Asn Val Asn Asp Ser Val Thr Lys Gln Lys Phe Asp
        275                 280                 285

Asn Leu Tyr Cys Cys Arg Glu Ser Ile Leu Asp Gly Leu Lys Arg Thr
290                 295                 300

Thr Asp Val Met Phe Gly Gly Lys Gln Val Val Cys Gly Tyr Gly
305                 310                 315                 320

Glu Val Gly Lys Gly Cys Cys Ala Ala Leu Lys Ala Leu Gly Ala Ile
                325                 330                 335

Val Tyr Ile Thr Glu Ile Asp Pro Ile Cys Ala Leu Gln Ala Cys Met
            340                 345                 350

Asp Gly Phe Arg Val Val Lys Leu Asn Glu Val Ile Arg Gln Val Asp
        355                 360                 365

```
Val Val Ile Thr Cys Thr Gly Asn Lys Asn Val Thr Arg Glu His
    370                 375                 380

Leu Asp Arg Met Lys Asn Ser Cys Ile Val Cys Asn Met Gly His Ser
385                 390                 395                 400

Asn Thr Glu Ile Asp Val Thr Ser Leu Arg Thr Pro Glu Leu Thr Trp
                405                 410                 415

Glu Arg Val Arg Ser Gln Val Asp His Val Ile Trp Pro Asp Gly Lys
                420                 425                 430

Arg Val Val Leu Leu Ala Glu Gly Arg Leu Leu Asn Leu Ser Cys Ser
                435                 440                 445

Thr Val Pro Thr Phe Val Leu Ser Ile Thr Ala Thr Thr Gln Ala Leu
    450                 455                 460

Ala Leu Ile Glu Leu Tyr Asn Ala Pro Glu Gly Arg Tyr Lys Gln Asp
465                 470                 475                 480

Val Tyr Leu Leu Pro Lys Lys Met Asp Glu Tyr Val Ala Ser Leu His
                485                 490                 495

Leu Pro Ser Phe Asp Ala His Leu Thr Glu Leu Thr Asp Asp Gln Ala
                500                 505                 510

Lys Tyr Leu Gly Leu Asn Lys Asn Gly Pro Phe Lys Pro Asn Tyr Tyr
            515                 520                 525

Arg Tyr
    530

<210> SEQ ID NO 5
<211> LENGTH: 585
<212> TYPE: PRT
<213> ORGANISM: Mus musculus

<400> SEQUENCE: 5

Met Ala Thr Cys Trp Gln Ala Leu Trp Ala Tyr Arg Ser Tyr Leu Ile
1               5                   10                  15

Val Leu Cys Leu Pro Ile Phe Leu Leu Pro Leu Pro Leu Ile Val Gln
                20                  25                  30

Thr Lys Glu Ala Tyr Cys Ala Tyr Ser Ile Ile Leu Met Ala Leu Leu
            35                  40                  45

Trp Cys Thr Glu Ala Leu Pro Leu Ala Val Thr Ala Leu Phe Pro Ile
    50                  55                  60

Ile Leu Phe Pro Leu Met Gly Ile Met Glu Ala Ser Lys Val Cys Leu
65                  70                  75                  80

Glu Tyr Phe Lys Asp Thr Asn Ile Leu Phe Val Gly Gly Leu Met Val
                85                  90                  95

Ala Ile Ala Val Glu His Trp Asn Leu His Lys Arg Ile Ala Leu Gly
                100                 105                 110

Val Leu Leu Ile Ile Gly Val Arg Pro Ala Leu Leu Leu Gly Phe
            115                 120                 125

Met Leu Val Thr Ala Phe Leu Ser Met Trp Ile Ser Asn Thr Ala Thr
    130                 135                 140

Thr Ala Met Met Leu Pro Ile Gly Tyr Ala Val Leu Glu Gln Leu Gln
145                 150                 155                 160

Gly Ser Gln Lys Asp Val Glu Glu Gly Asn Ser Asn Pro Ser Phe Glu
                165                 170                 175

Leu Gln Glu Ala Ser Pro Gln Lys Glu Glu Thr Lys Leu Asp Asn Gly
                180                 185                 190

Gln Ala Val Ser Val Ser Ser Glu Pro Arg Ala Gln Lys Thr Lys Glu
```

-continued

```
                195                 200                 205
His His Arg Phe Ser Gln Gly Leu Ser Leu Cys Ile Cys Tyr Ser Ala
210                 215                 220

Ser Ile Gly Gly Ile Ala Thr Leu Thr Gly Thr Thr Pro Asn Leu Val
225                 230                 235                 240

Leu Gln Gly Gln Val Asn Ser Ile Phe Pro Glu Asn Ser Asn Val Val
                245                 250                 255

Asn Phe Ala Ser Trp Phe Gly Phe Ala Phe Pro Thr Met Val Ile Leu
            260                 265                 270

Leu Leu Leu Ala Trp Leu Trp Leu Gln Val Leu Phe Leu Gly Val Asn
        275                 280                 285

Phe Arg Lys Asn Phe Gly Phe Gly Glu Gly Glu Glu Arg Lys Gln
290                 295                 300

Ala Ala Phe Gln Val Ile Lys Thr Gln His Arg Leu Leu Gly Pro Met
305                 310                 315                 320

Ser Phe Ala Glu Lys Ala Val Thr Phe Leu Phe Val Leu Leu Val Val
                325                 330                 335

Leu Trp Phe Thr Arg Glu Pro Gly Phe Pro Gly Trp Gly Asp Thr
            340                 345                 350

Ala Phe Ala Asn Lys Gly Gln Ser Met Val Ser Asp Gly Thr Val Ala
        355                 360                 365

Ile Phe Ile Ser Leu Ile Met Phe Ile Ile Pro Ser Lys Ile Pro Gly
370                 375                 380

Leu Thr Glu Asp Pro Lys Lys Pro Gly Lys Leu Lys Ala Pro Pro Ala
385                 390                 395                 400

Ile Leu Thr Trp Lys Thr Val Asn Asp Lys Met Pro Trp Asn Ile Leu
                405                 410                 415

Ile Leu Leu Gly Gly Phe Ala Leu Ala Lys Gly Ser Glu Glu Ser
            420                 425                 430

Gly Leu Ser Lys Trp Leu Gly Asp Lys Leu Thr Pro Leu Gln His Val
        435                 440                 445

Pro Pro Ser Ala Thr Val Leu Ile Leu Ser Leu Leu Val Ala Ile Phe
450                 455                 460

Thr Glu Cys Thr Ser Asn Val Ala Thr Thr Thr Leu Phe Leu Pro Ile
465                 470                 475                 480

Leu Ala Ser Met Ala Gln Ala Ile Cys Leu His Pro Leu Tyr Val Met
                485                 490                 495

Leu Pro Cys Thr Leu Ala Ala Ser Leu Ala Phe Met Leu Pro Val Ala
            500                 505                 510

Thr Pro Pro Asn Ala Ile Val Phe Ser Phe Gly Gly Leu Lys Val Ser
        515                 520                 525

Asp Met Ala Arg Ala Gly Phe Leu Leu Asn Ile Ile Gly Val Leu Thr
530                 535                 540

Ile Thr Leu Ser Ile Asn Ser Trp Ser Ile Pro Ile Phe Lys Leu Asp
545                 550                 555                 560

Thr Phe Pro Thr Trp Ala Tyr Ser Asn Thr Ser Gln Cys Leu Leu Asn
                565                 570                 575

Pro Pro Asn Ser Thr Val Pro Gly His
            580                 585
```

<210> SEQ ID NO 6
<211> LENGTH: 641
<212> TYPE: PRT
<213> ORGANISM: Homo sapiens

<400> SEQUENCE: 6

```
Met Ala Thr Cys Trp Gln Ala Leu Trp Ala Tyr Arg Ser Tyr Leu Ile
1               5                   10                  15

Val Phe Val Pro Ile Leu Leu Pro Leu Pro Ile Leu Val Pro
            20                  25                  30

Ser Lys Glu Ala Tyr Cys Ala Tyr Ala Ile Ile Leu Met Ala Leu Phe
            35                  40                  45

Trp Cys Thr Glu Ala Leu Pro Leu Ala Val Thr Ala Leu Phe Pro Leu
50                  55                  60

Ile Leu Phe Pro Met Met Gly Ile Val Asp Ala Ser Glu Ile Ile Gln
65                  70                  75                  80

Arg Pro Phe Pro Ser Ser Phe Glu Ser Pro Gly Glu Cys Gln Ser Val
                85                  90                  95

Gly Met Ser Val Thr Ala Ser His Asn Leu Gly Gly Thr Val Gly Asp
            100                 105                 110

Ser Arg Val Phe Pro Pro Leu Ser His Val Ser Thr Cys Gln Val Ala
            115                 120                 125

Val Glu Tyr Leu Lys Asp Ser Asn Leu Leu Phe Phe Gly Gly Leu Leu
130                 135                 140

Val Ala Ile Ala Val Glu His Trp Asn Leu His Lys Arg Ile Ala Leu
145                 150                 155                 160

Arg Val Leu Leu Ile Val Gly Val Arg Pro Ala Pro Leu Ile Leu Gly
                165                 170                 175

Phe Met Leu Val Thr Ala Phe Leu Ser Met Trp Ile Ser Asn Thr Ala
            180                 185                 190

Thr Ser Ala Met Met Val Pro Ile Ala His Ala Val Leu Asp Gln Leu
            195                 200                 205

His Ser Ser Gln Ala Ser Ser Asn Val Glu Glu Gly Ser Asn Asn Pro
210                 215                 220

Thr Phe Glu Leu Gln Glu Pro Ser Pro Gln Lys Glu Val Thr Lys Leu
225                 230                 235                 240

Asp Asn Gly Gln Ala Leu Pro Val Thr Ser Ala Ser Ser Glu Gly Arg
                245                 250                 255

Ala His Leu Ser Gln Lys His Leu His Leu Thr Gln Cys Met Ser Leu
            260                 265                 270

Cys Val Cys Tyr Ser Ala Ser Ile Gly Gly Ile Ala Thr Leu Thr Gly
            275                 280                 285

Thr Ala Pro Asn Leu Val Leu Gln Gly Gln Ile Asn Ser Leu Phe Pro
290                 295                 300

Gln Asn Gly Asn Val Val Asn Phe Ala Ser Trp Phe Ser Phe Ala Phe
305                 310                 315                 320

Pro Thr Met Val Ile Leu Leu Leu Ala Trp Leu Trp Leu Gln Ile
                325                 330                 335

Leu Phe Leu Gly Phe Asn Phe Arg Lys Asn Phe Gly Ile Gly Glu Lys
            340                 345                 350

Met Gln Glu Gln Gln Gln Ala Ala Tyr Cys Val Ile Gln Thr Glu His
            355                 360                 365

Arg Leu Leu Gly Pro Met Thr Phe Ala Glu Lys Ala Ile Ser Ile Leu
            370                 375                 380

Phe Val Ile Leu Val Leu Leu Trp Phe Thr Arg Glu Pro Gly Phe Phe
385                 390                 395                 400

Leu Gly Trp Gly Asn Leu Ala Phe Pro Asn Ala Lys Gly Glu Ser Met
```

```
            405                 410                 415
Val Ser Asp Gly Thr Val Ala Ile Phe Ile Gly Ile Ile Met Phe Ile
            420                 425                 430

Ile Pro Ser Lys Phe Pro Gly Leu Thr Gln Asp Pro Glu Asn Pro Gly
            435                 440                 445

Lys Leu Lys Ala Pro Leu Gly Leu Leu Asp Trp Lys Thr Val Asn Gln
            450                 455                 460

Lys Met Pro Trp Asn Ile Val Leu Leu Gly Gly Tyr Ala Leu
465                 470                 475                 480

Ala Lys Gly Ser Glu Arg Ser Gly Leu Ser Glu Trp Leu Gly Asn Lys
                485                 490                 495

Leu Thr Pro Leu Gln Ser Val Pro Ala Pro Ala Ile Ala Ile Ile Leu
            500                 505                 510

Ser Leu Leu Val Ala Thr Phe Thr Glu Cys Thr Ser Asn Val Ala Thr
            515                 520                 525

Thr Thr Ile Phe Leu Pro Ile Leu Ala Ser Met Ala Gln Ala Ile Cys
            530                 535                 540

Leu His Pro Leu Tyr Val Met Leu Pro Cys Thr Leu Ala Thr Ser Leu
545                 550                 555                 560

Ala Phe Met Leu Pro Val Ala Thr Pro Pro Asn Ala Ile Val Phe Ser
                565                 570                 575

Phe Gly Asp Leu Lys Val Leu Asp Met Ala Arg Ala Gly Phe Leu Leu
            580                 585                 590

Asn Ile Ile Gly Val Leu Ile Ile Ala Leu Ala Ile Asn Ser Trp Gly
            595                 600                 605

Ile Pro Leu Phe Ser Leu His Ser Phe Pro Ser Trp Ala Gln Ser Asn
            610                 615                 620

Thr Thr Ala Gln Cys Leu Pro Ser Leu Ala Asn Thr Thr Thr Pro Ser
625                 630                 635                 640

Pro

<210> SEQ ID NO 7
<211> LENGTH: 334
<212> TYPE: PRT
<213> ORGANISM: Homo sapiens

<400> SEQUENCE: 7

Met Leu Gly Ile Met Ala Trp Asn Ala Thr Cys Lys Asn Trp Leu Ala
1               5                   10                  15

Ala Glu Ala Ala Leu Glu Lys Tyr Tyr Leu Ser Ile Phe Tyr Gly Ile
            20                  25                  30

Glu Phe Val Val Gly Val Leu Gly Asn Thr Ile Val Val Tyr Gly Tyr
            35                  40                  45

Ile Phe Ser Leu Lys Asn Trp Asn Ser Ser Asn Ile Tyr Leu Phe Asn
        50                  55                  60

Leu Ser Val Ser Asp Leu Ala Phe Leu Cys Thr Leu Pro Met Leu Ile
65                  70                  75                  80

Arg Ser Tyr Ala Asn Gly Asn Trp Ile Tyr Gly Asp Val Leu Cys Ile
                85                  90                  95

Ser Asn Arg Tyr Val Leu His Ala Asn Leu Tyr Thr Ser Ile Leu Phe
            100                 105                 110

Leu Thr Phe Ile Ser Ile Asp Arg Tyr Leu Ile Ile Lys Tyr Pro Phe
            115                 120                 125

Arg Glu His Leu Leu Gln Lys Lys Glu Phe Ala Ile Leu Ile Ser Leu
```

| | | 130 | | | 135 | | | | 140 | | |
|---|---|---|---|---|---|---|---|---|---|---|---|
| Ala | Ile | Trp | Val | Leu | Val | Thr | Leu | Glu | Leu | Leu | Pro | Ile | Leu | Pro | Leu |
| 145 | | | | 150 | | | | 155 | | | | 160 |

Ala Ile Trp Val Leu Val Thr Leu Glu Leu Leu Pro Ile Leu Pro Leu
145                 150                 155                 160

Ile Asn Pro Val Ile Thr Asp Asn Gly Thr Thr Cys Asn Asp Phe Ala
            165                 170                 175

Ser Ser Gly Asp Pro Asn Tyr Asn Leu Ile Tyr Ser Met Cys Leu Thr
            180                 185                 190

Leu Leu Gly Phe Leu Ile Pro Leu Phe Val Met Cys Phe Phe Tyr Tyr
            195                 200                 205

Lys Ile Ala Leu Phe Leu Lys Gln Arg Asn Arg Gln Val Ala Thr Ala
            210                 215                 220

Leu Pro Leu Glu Lys Pro Leu Asn Leu Val Ile Met Ala Val Val Ile
225                 230                 235                 240

Phe Ser Val Leu Phe Thr Pro Tyr His Val Met Arg Asn Val Arg Ile
            245                 250                 255

Ala Ser Arg Leu Gly Ser Trp Lys Gln Tyr Gln Cys Thr Gln Val Val
            260                 265                 270

Ile Asn Ser Phe Tyr Ile Val Thr Arg Pro Leu Ala Phe Leu Asn Ser
            275                 280                 285

Val Ile Asn Pro Val Phe Tyr Phe Leu Leu Gly Asp His Phe Arg Asp
            290                 295                 300

Met Leu Met Asn Gln Leu Arg His Asn Phe Lys Ser Leu Thr Ser Phe
305                 310                 315                 320

Ser Arg Trp Ala His Glu Leu Leu Ser Phe Arg Glu Lys
            325                 330

<210> SEQ ID NO 8
<211> LENGTH: 1005
<212> TYPE: DNA
<213> ORGANISM: Homo sapiens

<400> SEQUENCE: 8

```
atgctgggga tcatggcatg aatgcaact tgcaaaaact ggctggcagc agaggctgcc      60
ctggaaaagt actacctttc cattttttat gggattgagt tcgttgtggg agtccttgga    120
aataccattg ttgtttacgg ctacatcttc tctctgaaga actggaacag cagtaatatt    180
tatctctttta acctctctgt ctctgactta gcttttctgt gcaccctccc catgctgata    240
aggagttatg ccaatggaaa ctggatatat ggagacgtgc tctgcataag caaccgatat    300
gtgcttcatg ccaacctcta taccagcatt ctctttctca cttttatcag catagatcga    360
tacttgataa ttaagtatcc tttccgagaa caccttctgc aaaagaaaga gtttgctatt    420
taatctccct tggccatttg ggttttagta accttagagt tactacccat acttcccctt    480
ataaatcctg ttataactga caatggcacc acctgtaatg attttgcaag ttctggagac    540
cccaactaca acctcattta cagcatgtgt ctaacactgt tggggttcct tattcctctt    600
tttgtgatgt gttctttta ttacaagatt gctctcttcc taaagcagag gaataggcag    660
gttgctactg ctctgcccct tgaaaagcct ctcaacttgg tcatcatggc agtggtaatc    720
ttctctgtgc tttttacacc ctatcacgtc atgcggaatg tgaggatcgc ttcacgcctg    780
gggagttgga agcagtatca gtgcactcag gtcgtcatca actccttta cattgtgaca    840
cggcctttgg cctttctgaa cagtgtcatc aaccctgtct ctatttttct tttgggagat    900
cacttcaggg acatgctgat gaatcaactg agacacaact tcaaatccct tacatccttt    960
agcagatggg ctcatgaact cctactttca ttcagagaaa agtga              1005
```

<210> SEQ ID NO 9
<211> LENGTH: 60
<212> TYPE: PRT
<213> ORGANISM: Vibrio cholerae
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid

<400> SEQUENCE: 9

Ala Asn Ser Ile Ile Phe Leu Phe Leu Gly Gly Phe Ala Leu Ala Ala
1               5                   10                  15

Ala Xaa His His Gln Gly Leu Asp Lys Val Ile Ala Asp Lys Val Leu
                20                  25                  30

Ala Xaa Ala Gln Gly Lys Xaa Ser Val Ala Val Phe Xaa Leu Phe Gly
            35                  40                  45

Val Thr Ala Leu Leu Ser Xaa Trp Ile Ser Asn Thr
        50                  55                  60

<210> SEQ ID NO 10
<211> LENGTH: 60
<212> TYPE: PRT
<213> ORGANISM: Staphylococcus aureus

<400> SEQUENCE: 10

Gly Asn Asp Ile Ile Phe Leu Phe Leu Gly Gly Phe Ile Leu Ala Ile
1               5                   10                  15

Ala Met Glu Arg Trp Asn Leu His Thr Arg Val Ala Leu Thr Ile Ile
                20                  25                  30

Asn Leu Ile Gly Ala Ser Thr Ser Lys Ile Leu Leu Gly Phe Met Val
            35                  40                  45

Ala Thr Gly Phe Leu Ser Met Phe Val Ser Asn Thr
        50                  55                  60

<210> SEQ ID NO 11
<211> LENGTH: 60
<212> TYPE: PRT
<213> ORGANISM: Drosophila melanogaster

<400> SEQUENCE: 11

Phe Lys Asp Thr Leu Val Met Phe Met Gly Gly Ile Met Val Ala Leu
1               5                   10                  15

Ala Val Glu Tyr Cys Asn Leu His Lys Arg Leu Ala Leu Arg Val Ile
                20                  25                  30

Gln Ile Val Gly Cys Ser Pro Arg Arg Leu His Phe Gly Leu Ile Met
            35                  40                  45

Val Thr Met Phe Leu Ser Met Trp Ile Ser Asn Ala

```
                50                  55                  60
```

<210> SEQ ID NO 12
<211> LENGTH: 60
<212> TYPE: PRT
<213> ORGANISM: Homo sapiens

<400> SEQUENCE: 12

```
Leu Lys Asp Ser Asn Leu Leu Phe Phe Gly Gly Leu Val Ala Ile
1               5                   10                  15

Ala Val Glu His Trp Asn Leu His Lys Arg Ile Ala Leu Arg Val Leu
                20                  25                  30

Leu Ile Val Gly Val Arg Pro Ala Pro Leu Ile Leu Gly Phe Met Leu
            35                  40                  45

Val Thr Ala Phe Leu Ser Met Trp Ile Ser Asn Thr
        50                  55                  60
```

<210> SEQ ID NO 13
<211> LENGTH: 61
<212> TYPE: PRT
<213> ORGANISM: Mus musculus

<400> SEQUENCE: 13

```
Phe Lys Asp Thr Asn Ile Leu Phe Val Gly Gly Leu Met Val Ala Ile
1               5                   10                  15

Ala Val Glu His Trp Asn Leu His Lys Arg Ile Ala Leu Gly Val Ile
                20                  25                  30

Leu Leu Ile Ile Gly Val Arg Pro Ala Leu Leu Leu Gly Phe Met
            35                  40                  45

Leu Val Thr Ala Phe Leu Ser Met Trp Ile Ser Asn Thr
        50                  55                  60
```

<210> SEQ ID NO 14
<211> LENGTH: 60
<212> TYPE: PRT
<213> ORGANISM: Homo sapiens

<400> SEQUENCE: 14

```
Phe Leu Asp Thr Asn Phe Leu Phe Leu Ser Gly Leu Ile Met Ala Ser
1               5                   10                  15

Ala Ile Glu Glu Trp Asn Leu His Arg Arg Ile Ala Leu Lys Ile Leu
                20                  25                  30

Met Leu Val Gly Val Gln Pro Ala Arg Leu Ile Leu Gly Met Met Val
            35                  40                  45

Thr Thr Ser Phe Leu Ser Met Trp Leu Ser Asn Thr
        50                  55                  60
```

<210> SEQ ID NO 15
<211> LENGTH: 60
<212> TYPE: PRT
<213> ORGANISM: Mus musculus

<400> SEQUENCE: 15

```
Phe Leu Asp Thr Asn Phe Leu Phe Leu Ser Gly Leu Ile Met Ala Ser
1               5                   10                  15

Ala Ile Glu Glu Trp Asn Leu His Arg Arg Ile Ala Leu Lys Val Leu
                20                  25                  30

Met Leu Val Gly Val Gln Pro Ala Arg Leu Ile Leu Gly Met Met Val
            35                  40                  45
```

```
Thr Thr Ser Phe Leu Ser Met Trp Leu Ser Asn Thr
    50                  55                  60

<210> SEQ ID NO 16
<211> LENGTH: 60
<212> TYPE: PRT
<213> ORGANISM: Homo sapiens

<400> SEQUENCE: 16

Met Lys Asp Thr Asn Met Leu Phe Leu Gly Gly Leu Ile Val Ala Val
1               5                   10                  15

Ala Val Glu Arg Trp Asn Leu His Lys Arg Ile Ala Leu Arg Thr Leu
                20                  25                  30

Leu Trp Val Gly Ala Lys Pro Ala Arg Leu Met Leu Gly Phe Met Gly
            35                  40                  45

Val Thr Ala Leu Leu Ser Met Trp Ile Ser Asn Thr
    50                  55                  60

<210> SEQ ID NO 17
<211> LENGTH: 60
<212> TYPE: PRT
<213> ORGANISM: Mus musculus

<400> SEQUENCE: 17

Met Lys Asp Thr Asn Met Leu Phe Leu Gly Ser Leu Ile Val Ala Val
1               5                   10                  15

Ala Val Glu Arg Trp Lys Leu His Lys Arg Val Ala Leu Arg Met Leu
                20                  25                  30

Leu Phe Val Gly Thr Lys Pro Ser Arg Leu Met Leu Gly Phe Met Phe
            35                  40                  45

Val Thr Ala Phe Leu Ser Met Trp Ile Ser Asn Thr
    50                  55                  60

<210> SEQ ID NO 18
<211> LENGTH: 60
<212> TYPE: PRT
<213> ORGANISM: Homo sapiens

<400> SEQUENCE: 18

Phe Lys Asp Phe His Leu Leu Leu Ile Gly Val Ile Cys Leu Ala Thr
1               5                   10                  15

Ser Ile Glu Lys Trp Asn Leu His Lys Arg Ile Ala Leu Lys Met Val
                20                  25                  30

Met Met Val Gly Val Asn Pro Ala Trp Leu Thr Leu Gly Phe Met Ser
            35                  40                  45

Ser Thr Ala Phe Leu Ser Met Trp Leu Ser Asn Thr
    50                  55                  60

<210> SEQ ID NO 19
<211> LENGTH: 60
<212> TYPE: PRT
<213> ORGANISM: Mus musculus

<400> SEQUENCE: 19

Phe Lys Asp Phe His Leu Leu Leu Ile Val Gly Ile Cys Leu Ala Thr
1               5                   10                  15

Ser Ile Glu Lys Trp Asn Leu His Lys Arg Ile Ala Leu Arg Met Val
                20                  25                  30

Met Met Val Gly Val Asn Pro Ala Trp Leu Thr Leu Gly Phe Met Ser
            35                  40                  45
```

```
Ser Thr Ala Phe Leu Ser Met Trp Leu Ser Asn Thr
 50                  55                  60
```

<210> SEQ ID NO 20
<211> LENGTH: 60
<212> TYPE: PRT
<213> ORGANISM: Homo sapiens

<400> SEQUENCE: 20

```
Phe Lys Asn Thr Thr Leu Leu Leu Val Gly Val Ile Cys Val Ala Ala
1               5                   10                  15

Ala Val Glu Lys Trp Asn Leu His Lys Arg Ile Ala Leu Arg Met Val
             20                  25                  30

Leu Met Ala Gly Ala Lys Pro Gly Met Leu Leu Leu Cys Phe Met Cys
         35                  40                  45

Cys Thr Thr Leu Leu Ser Met Trp Leu Ser Asn Thr
 50                  55                  60
```

<210> SEQ ID NO 21
<211> LENGTH: 63
<212> TYPE: PRT
<213> ORGANISM: Homo sapiens

<400> SEQUENCE: 21

```
Glu Glu Lys Leu Arg Lys Gln Ala Ala Ser Pro Lys Gly Ala Ser Val
1               5                   10                  15

Ser Ile Asn Val Asn Thr Ser Leu Glu Asp Met Arg Ser Asn Asn Val
             20                  25                  30

Glu Asp Cys Lys Met Met Gln Val Ser Ser Gly Asp Lys Met Glu Asp
         35                  40                  45

Ala Thr Ala Asn Gly Gln Glu Asp Ser Lys Ala Pro Asp Gly Ser
 50                  55                  60
```

<210> SEQ ID NO 22
<211> LENGTH: 62
<212> TYPE: PRT
<213> ORGANISM: Mus musculus

<400> SEQUENCE: 22

```
Ala Lys Lys Ser Gln Lys Gln Asp Ala Ser Ser Lys Ile Ser Ser Val
1               5                   10                  15

Ser Val Asn Val Asn Thr Asn Leu Glu Asp Val Lys Ser Asn Asp Val
             20                  25                  30

Glu Gly Ser Glu Ala Lys Val His Gln Gly Glu Leu Gln Asp Val
         35                  40                  45

Val Ser Ser Asn Gln Glu Asp Ala Lys Ala Pro Thr Met Thr
 50                  55                  60
```

<210> SEQ ID NO 23
<211> LENGTH: 57
<212> TYPE: PRT
<213> ORGANISM: Sus scrofa

<400> SEQUENCE: 23

```
Gly Asn Lys Leu Val Lys Lys Asp Thr Ser Ile Ser Ile Asn Val Asn
1               5                   10                  15

Thr Gly Ile Thr Asn Ile Glu Ser Asn Asp Val Glu Gly Ser Asn Val
             20                  25                  30

Lys Val Ser Ala Glu Lys Glu Leu Glu Asp Ile Ala Ala Gly Asp Gln
```

```
            35                  40                  45
Glu Asp Ala Lys Ala Pro Ala Met Ser
    50                  55
```